United States Patent
Chun et al.

(10) Patent No.: US 12,338,495 B2
(45) Date of Patent: *Jun. 24, 2025

(54) METHODS OF DIAGNOSING AND TREATING ALZHEIMER'S DISEASE

(71) Applicant: Sanford Burnham Prebys Medical Discovery Institute, La Jolla, CA (US)

(72) Inventors: Jerold Chun, La Jolla, CA (US); Ming-Hsiang Lee, La Jolla, CA (US)

(73) Assignee: SANFORD BURNHAM PREBYS MEDICAL DISCOVERY INSTITUTE, La Jolla, CA (US)

(*) Notice: Subject to any disclaimer, the term of this patent is extended or adjusted under 35 U.S.C. 154(b) by 191 days.

This patent is subject to a terminal disclaimer.

(21) Appl. No.: 16/610,293

(22) PCT Filed: May 1, 2018

(86) PCT No.: PCT/US2018/030520
§ 371 (c)(1),
(2) Date: Nov. 1, 2019

(87) PCT Pub. No.: WO2018/204408
PCT Pub. Date: Nov. 8, 2018

(65) Prior Publication Data
US 2020/0080154 A1    Mar. 12, 2020

Related U.S. Application Data

(60) Provisional application No. 62/500,270, filed on May 2, 2017.

(51) Int. Cl.
*C12Q 1/6883* (2018.01)
*C07K 14/47* (2006.01)
*C12N 15/113* (2010.01)

(52) U.S. Cl.
CPC ........ *C12Q 1/6883* (2013.01); *C07K 14/4703* (2013.01); *C07K 14/4711* (2013.01); *C12N 15/113* (2013.01); *C12N 2310/122* (2013.01); *C12N 2310/14* (2013.01); *C12Q 2600/156* (2013.01)

(58) Field of Classification Search
CPC ....... G01N 33/6896; G01N 2333/4709; G01N 2800/2821; C12Q 2521/301; C12Q 1/37; C12Q 1/6883; C12Q 2600/156; C12Q 1/6869; C12Q 1/6827; C12Q 1/6837; C12Q 1/701

See application file for complete search history.

(56) References Cited

U.S. PATENT DOCUMENTS

| 6,455,757 B1 * | 9/2002 | Mucke | A01K 67/0278 |
| | | | 800/12 |
| 2004/0167161 A1 * | 8/2004 | Nozaki | A61P 31/04 |
| | | | 514/573 |
| 2006/0228728 A1 | 10/2006 | Cox et al. | |
| 2006/0270841 A1 * | 11/2006 | Espeseth | C07K 14/4711 |
| | | | 435/325 |
| 2011/0166197 A1 | 7/2011 | Darling et al. | |
| 2013/0331286 A1 | 12/2013 | Sappenfield et al. | |
| 2014/0206675 A1 | 7/2014 | Scott et al. | |
| 2014/0235473 A1 * | 8/2014 | Otto | G01N 33/6893 |
| | | | 435/7.1 |
| 2015/0272962 A1 | 10/2015 | Zhu et al. | |

FOREIGN PATENT DOCUMENTS

| WO | WO-2005003387 A2 * | 1/2005 | ........... C12Q 1/6886 |
| WO | WO-2018204408 A1 | 11/2018 | |

OTHER PUBLICATIONS

Schreiner et al., Targeted combinatorial alternative splicing generates brain region-specific repertoires of neurexins, Neuron, vol. 84, pp. 386-398. (Year: 2014).*
Bushman et al., Genomic mosaicism with increased amyloid precursor protein (APP) gene copy number in single neurons from sporadic Alzheimer's disease brains, eLife, vol. 4:e05116, pp. 1-26. (Year: 2015).*
Johnson et al., Genome-wide survey of human alternative pre-mRNA splicing with exon junction microarrays, Science, vol. 302, pp. 2141-2144. (Year: 2003).*
Forsell et al., Amyloid precursor protein mutation at codon 713 (Ala→Val) does not cause schizophrenia: non-pathogenic variant found at codon 705 (silent), Neuroscience Letters, vol. 184, pp. 90-93. (Year: 1995).*
Tilgner et al., Comprehensive transcriptome analysis using synthetic long-read sequencing reveals molecular co-association of distant splicing events, Nature Biotechnology, vol. 33, pp. 736-742. (Year: 2015).*
Ghidoni et al., Novel T719P AbPP mutation unbalances the relative proportion of Amyloid-b peptides, Journal of Alzheimer's Disease, vol. 18, pp. 295-303. (Year: 2009).*
Di Fede et al., A recessive mutation in the APP gene with dominant-negative effect on amyloidogenesis, Science, vol. 323, pp. 1473-1477. (Year: 2009).*
Nicolas et al., Screening of dementia genes by whole-exome sequencing in early-onset Alzheimer disease: input and lessons, European Journal of Human Genetics, vol. 24, pp. 710-716. (Year: 2016).*
Parcerisas et al., Somatic signature of brain-specific single nucleotide variations in sporadic Alzheimer's disease, Journal of Alzheimer's Disease, vol. 42, pp. 1357-1382. (Year: 2014).*
Tang et al., Identification of a novel alternative splicing isoforms of human amyloid precursor protein, APP639, European Journal of Neuroscience, vol. 18, pp. 102-108. (Year: 2003).*

(Continued)

*Primary Examiner* — Dana H Shin
(74) *Attorney, Agent, or Firm* — WILSON SONSINI GOODRICH & ROSATI

(57) ABSTRACT

Described herein are methods for identifying and measuring one or more non-classical variant(s) of amyloid precursor protein (APP) gene. Provided herein are methods for diagnosing and treating an individual having or suspected of having Alzheimer's disease following identification of an expression profile or an activity profile of the one or more non-classical variant(s).

1 Claim, 51 Drawing Sheets

Specification includes a Sequence Listing.

(56) References Cited

OTHER PUBLICATIONS

Shi et al., Long-read sequencing and de novo assembly of a Chinese genome, Nature Communications, vol. 7:12065, pp. 1-10. (Year: 2015).*
Lee et al., Mosaic APP gene recombination in Alzheimer's disease—What's next? Journal of Experimental Neuroscience, vol. 13, pp. 1-4. (Year: 2019).*
Kaj Blennow, A review of fluid biomarkers for Alzheimer's disease: moving from CSF to blood, Neurology and Therapy, vol. 6, supplement 1, pp. S15-S24. (Year: 2017).*
König et al., Identification and differential expression of a novel alternative splice isoform of the betaA4 amyloid precursor protein (APP) mRNA in leukocytes and brain microglial cells, The Journal of Biological Chemistry, vol. 267, pp. 10804-10809. (Year: 1992).*
Kim et al., APP gene copy number changes reflect exogenous contamination, Nature, vol. 584, pp. E20-E33. (Year: 2020).*
Lee et al., Somatic APP gene recombination in Alzheimer's disease and normal neurons, Nature, vol. 563, pp. 639-645. (Year: 2018).*
Anand et al., A review on cholinesterase inhibitors for Alzheimer's disease, Archives of Pharmacal Research, vol. 36, pp. 375-399. (Year: 2013).*
GenBank accession No. HM005315 "*Homo sapiens* clone HTL-T-2 testicular tissue protein Li 2 mRNA, complete cds", Mar. 31, 2016 [online]. [Retrieved on Sep. 12, 2018]. Retrieved from the Internet< url:<a=""href="https://www.ncbi.nlm.nih.gov/nuccore/HM005315.1?report=genbank&to=2340">https://www.ncbi.nlm.nih.gov/nuccore/HM005315.1?report=genbank&to=2340</url:>.
Kang et al. The precursor of Alzheimer's disease amyloid A4 protein resembles a cell-surface receptor. Nature 325:733-736 (1987).
PCT/US2018/030520 International Search Report and Written Opinion dated Sep. 28, 2018.
PCT/US2018/030520 Invitation to Pay Additional Fees dated Aug. 2, 2018.
Sandbrink et al. Beta A4-amyloid protein precursor mRNA isoforms without exon 15 are ubiquitously expressed in rat tissues including brain, but not in neurons. J Biol Chem 269(2):1510-1517 (1994).
Kaneko et al. Novel plasma biomarker surrogating cerebral amyloid deposition. Proc Jpn Acad Ser B Phys Biol Sci 90(9):353-64 (2014).
Lee et al. Reply to: APP gene copy number changes reflect exogenous contamination. Nature 584:E29-E33 (2020).
Lee et al. Somatic APP gene recombination in Alzheimer's disease and normal neurons. Nature 563(7733):639-645 (2018) (With Extended Data).
Mitsunaga et al. Detection of APP gene recombinant in human blood plasma. Available at https://assets.researchsquare.com/files/rs-3007766/v1/91a4ded1-1c72-41f9-9c41-e5ebb79992c4.pdf?c=1686325437 (Posted Jun. 9, 2023).
Mitsunaga et al. Detection of APP gene recombinant in human blood plasma. Sci Rep 13(1):21703 (2023).
Sheinerman, Kira S. et al. Circulating cell-free microRNA as biomarkers for screening, diagnosis, and monitoring of neurodegenerative diseases and other neurologic pathologies. Front Cell Neurosci 7:150 (2013).

* cited by examiner

| NAME | STRUCTURE | RT-PCR | DNA PCR |
|---|---|---|---|
| APP-R3/16 |  1  249 2008    2313 | ✓ | ✓ |
| APP-R2/18 |  1  210 2266 2313 | ✓ | ✓ |
| APP-R6/18 |  1        735 2233 2313 | ✓ | |
| APP-R3/14 |  1  267  1897    2313 | ✓ | ✓ |
| APP-R3/17 |  1  312  2127  2313 | ✓ | ✓ |
| APP-R1/11 |  1 24 1439      2313 | ✓ | ✓ |
| APP-R1/11-2 |  1 42 1458      2313 | ✓ | |
| APP-R1/14 |  1 41 1814    2313 | ✓ | ✓ |
| APP-R2/16 |  1 216  2014   2313 | ✓ | |
| APP-R2/17 |  1 63 2102 2313 | ✓ | ✓ |
| APP-R6/17 |  1       672 2098 2313 | ✓ | |
| APP-R2/14 |  1  198 1755     2313 | ✓ | |
| APP-D2/18-2 |  1 120 2286 2313 | | ✓ |

RE Digestion of IEJ 13/16

Genomic variants
- APP 751, Δ8
- D1/12
- D5/16
- D3/14
- D3/16
- D3/17
- D1/17
- D2/18

FIG. 20B

SEQUENCE LISTING

```
<160> NUMBER OF SEQ ID NOS: 42

<210> SEQ ID NO 1
<211> LENGTH: 555
<212> TYPE: DNA
<213> ORGANISM: Homo sapiens

<400> SEQUENCE: 1
atgctgcccg gtttggcact gctcctgctg gccgcctgga cggctcgggc gctggaggta      60
cccactgatg gtaatgctgg cctgctggct gaacccagga ttgccatgtt ctgtggcaga     120
ctgaacatgc acatgaatgt ccagaatggg aagtgggatt cagatccatc agggaccaaa     180
acctgcattg ataccaagga aggcatcctg cagtattgcc aagaagtcta ccctgaactg     240
cagatcacca agatggatgc agaattccga catgactcag gatatgaagt tcatcatcaa     300
aaattggtgt tctttgcaga agatgtgggt tcaaacaaag gtgcaatcat tggactcatg     360
gtgggcggtg ttgtcatagc gacagtgatc gtcatcacct tggtgatgct gaagaagaaa     420
cagtacacat ccattcatca tggtgtggtg gaggttgacg ccgctgtcac cccagaggag     480
cgccacctgt ccaagatgca gcagaacggc tacgaaaatc caacctacaa gttctttgag     540
cagatgcaga actag                                                      555

<210> SEQ ID NO 2
<211> LENGTH: 555
<212> TYPE: DNA
<213> ORGANISM: Homo sapiens

<400> SEQUENCE: 2
atgctgcccg gtttggcact gctcctgctg gccgcctgga cggctcgggc gctggaggta      60
cccactgatg gtaatgctgg cctgctggct gaacccagga ttgccatgtt ctgtggcaga     120
ctgaacatgc acatgaatgt ccagaatggg aagtgggatt cagatccatc agggaccaaa     180
acctgcattg ataccaagga aggcatcctg cagtattgcc aagaagtcta ccctgaactg     240
cagatcacca agatggatgc agaattccga catgactcag gatatgaagt tcatcatcaa     300
aaattggtgt tctttgcaga agatgtgggt tcaaacaaag gtgcaatcat tggactcata     360
gtgggcggtg ttgtcatagc gacagtgatc gtcatcacct tggtgatgct gaagaagaaa     420
cagtacacat ccattcatca tggtgtggtg gaggttgacg ccgctgtcac cccagaggag     480
cgccacctgt ccaagatgca gcagaacggc tacgaaaatc caacctacaa gttctttgag     540
cagatgcaga actag                                                      555

<210> SEQ ID NO 3
<211> LENGTH: 258
<212> TYPE: DNA
<213> ORGANISM: Homo sapiens
```

<400> SEQUENCE: 3

```
atgctgcccg ttttggcact gctcctgctg gccgcctgga cggctcgggc gctggaggta        60
cccactgatg gtaatgctgg cctgctggct gaaccccaga ttgccatgtt ctgtggcaga       120
ctgaacatgc acatgaatgt ccagaatggg aagtgggatt cagatccatc agggaccaaa       180
acctgcattg ataccaagga aggcatcctg cgctacgaaa atccaaccta caagttcttt       240
gagcagatgc agaactag                                                     258
```

<210> SEQ ID NO 4
<211> LENGTH: 816
<212> TYPE: DNA
<213> ORGANISM: Homo sapiens

<400> SEQUENCE: 4

```
atgctgcccg ttttggcact gctcctgctg gccgcctgga cggctcgggc gctggaggta        60
cccactgatg gtaatgctgg cctgctggct gaaccccaga ttgccatgtt ctgtggcaga       120
ctgaacatgc acatgaatgt ccagaatggg aagtgggatt cagatccatc agggaccaaa       180
acctgcattg ataccaagga aggcatcctg cagtattgcc aagaagtcta ccctgaactg       240
cagatcacca atgtggtaga agccaaccaa ccagtgacca tccagaactg gtgcaagcgg       300
ggccgcaagc agtgcaagac ccatccccac tttgtgattc cctaccgctg cttagttggt       360
gagtttgtaa gtgatgccct tctcgttcct gacaagtgca aattcttaca ccaggagagg       420
atggatgttt gcgaaactca tcttcactgg cacaccgtcg ccaaagagac atgcagtgag       480
aagagtacca acttgcatga ctacggcatg ttgctgccct gcggaattga caagttccga       540
ggggtagagt ttgtgtgttg cccactggct gaagaaagtg acaatgtgga ttctgctgat       600
gcggaggagg atgactcgga tgtctggtgg ggcggagcag acacagacta tgcagatggg       660
agtgaagaca agtagtaga agtagcagag gaggaagaag tggctgaggt ggaagaagaa       720
gaagccgatg atgacgagga cgccacctg tccaagatgc agcagagcgg ctacgaaaat       780
ccaacctaca gttctttga gcagatgcag aactag                                  816
```

<210> SEQ ID NO 5
<211> LENGTH: 684
<212> TYPE: DNA
<213> ORGANISM: Homo sapiens

<400> SEQUENCE: 5

```
atgctgcccg ttttggcact gctcctgctg gccgcctgga cggctcgggc gctggaggta        60
cccactgatg gtaatgctgg cctgctggct gaaccccaga ttgccatgtt ctgtggcaga       120
ctgaacatgc acatgaatgt ccagaatggg aagtgggatt cagatccatc agggaccaaa       180
acctgcattg ataccaagga aggcatcctg cagtattgcc aagaagtcta ccctgaactg       240
cagatcacca atgtggtaga agccaacaca gaaaacgaag ttgagcctgt tgatgcccgc       300
cctgctgccg accgaggact gaccactcga ccaggttctg ggttgacaaa tatcaagacg       360
gaggagatct ctgaagtgaa gatggatgca gaattccgac atgactcagg atatgaagtt       420
catcatcaaa aattggtgtt ctttacagaa gatgtgggtt caaacaaagg tgcaatcatt       480
ggactcatgg tgggcggtgt tgtcatagcg acagtgatcg tcatcacctt ggtgatgctg       540
aagaagaaac agtacacatc cattcatcat ggtgtggtgg aggttgacgc cgctgtcacc       600
```

```
ccagaggagc gccacctgtc caagatgcag cagaacggct acgaaaatcc aacctacaag    660
ttctttgagc agatgcagaa ctag                                          684

<210> SEQ ID NO 6
<211> LENGTH: 499
<212> TYPE: DNA
<213> ORGANISM: Homo sapiens

<400> SEQUENCE: 6
atgctgcccg ttttggcact gctcctgctg gccgcctgga cggctcgggc gctggagata     60
cccactgatg gtaatgctgg cctgctggct gaaccccaga ttgccatgtt ctgtggcaga    120
ctgaacatgc acatgaatgt ccagaatggg aagtgggact cagatccatc agggaccaaa    180
acctgcatta taccaaggaa aggcatcctg cagtattgcc aagaagtcta ccctgaactg    240
cagatcacca atgtggtaga agccaaccaa ccagtgacca tccagaactg gtgcaagcgg    300
ggccgcaagc agtgttgtca tagcgacagt gatcgtcatc accttggtga tgctgaagaa    360
gaaacagtac acatccattc atcatggtgt ggtggaggtt gacgccgctg tcaccccaga    420
ggagcgccac ctgtccaaga tgcagcagaa cggctacgaa aatccaacct acaagttctt    480
tgagcagatg cagaactag                                                499

<210> SEQ ID NO 7
<211> LENGTH: 898
<212> TYPE: DNA
<213> ORGANISM: Homo sapiens

<400> SEQUENCE: 7
atgctgcccg ttttggcact gctcctgctg gccgcctgga cggcctcgtc acgtgttcaa     60
tatgctaaag aagtatgtcc gcgcagaaca gaaggacaga cagcacaccc taaagcattt    120
cgagcatgtg cgcatggtgg atcccaagaa agccgctcag atccggtccc aggttatgac    180
acacctccgt gtgatttatg agcgcatgaa tcagtctctc tccctgctct acaacgtgcc    240
tgcagtggcc gaggagattc aggatgaagt tgatgagctg cttcagaaag agcaaaacta    300
ttcagatgac gtcttggcca acatgattag tgaaccaagg atcagttacg gaaacgatgc    360
tctcatgcca tctttgaccg aaacgaaaac caccgtggag ctccttcccg tgaatggaga    420
gttcagcctg gacgatctcc agccgtggca ttctttttggg gctgactctg tgccagccaa    480
cacagaaaac gaagttgagc ctgttgatgc ccgccctgct gccgaccgag gactgaccac    540
tcgaccaggt tctggggttga caaatatcaa gacggaggag atctctgaag tgaagatgga    600
tgcagaattc cgacatgact caggatatga agttcatcat caaaaattgg tgttctttgc    660
agaagatgtg ggttcaaaca aggtgcaatc attggactca tggtgggtg tgttgtcat    720 agcgacagta tcgtcatca ccttggtgat gctgaagaag aaacagtaca catccattca    780
tcatggtgtg gtggaggttg acgccgctgt caccccagag gagcgccacc tgtccaagat    840
gcagcagaac ggctacgaaa atccaaccta caagttcttt gagcagatgc agaactag      898

<210> SEQ ID NO 8
<211> LENGTH: 680
<212> TYPE: DNA
<213> ORGANISM: Homo sapiens
```

<400> SEQUENCE: 8

```
atgctgcccg gtttggcact gctcctgcag tgggaggaga ttcaggatga agttgatgaa    60
ctgcttcaga aagagcaaaa ctattcagat gacgtcttgg ccaacatgat tagtgaacca   120
aggatcagtt acgaaacga tgctctcatg ccatctttga ccgaaacgaa aaccaccgtg   180
gagctccttc ccgtgaatgg agagttcagc ctggacgatc tccagccgtg gcattctttt   240
ggggctgact ctgtgccagc caacacagaa aacgaagttg agcctgttga tcccgccct    300
gctgccgacc gaggactgac cactcgacca ggttctgggt tgacaaatat caagacggag   360
gagatctctg aagtgaagat ggatgcagaa ttccgacatg actcaggata tgaagttcat   420
catcaaaaat tggtgttctt tgcagaagat gtgggttcaa acaaaggtgc aatcattgga   480
ctcatggtgg cggtgttgtc atagcgacag tgatcgtcat caccttggtg atgctgaaga   540
agaaacagta cacatccatt catcatggtg tggtggaggt tgacgccgct gtcacccag    600
aggagcgcca cctgtccaag atgtggcaga acggctacga aaatccaacc tacaagttct   660
tgagcagat gcagaactag                                                680
```

<210> SEQ ID NO 9
<211> LENGTH: 899
<212> TYPE: DNA
<213> ORGANISM: Homo sapiens

<400> SEQUENCE: 9

```
atgctgcccg gtttggcact gctcctgcagg ctgttcctcc tcggcctcgt cacgtgttca    60
atatgctaaa gaagtatgtc cgcgcagaac agaaggacag acagcacacc ctaaagcatt   120
tcgagcatgt gcgcatggtg gatcccaaga agccgctca gatccggtcc caggttatga    180
cacacctccg tgtgatttat gagcgcatga atcagtctct ctccctgctc tacaacgtgc   240
ctgcagtggc cgaggagatt caggatgaag ttgatgagct gcttcagaaa gagcaaaact   300
attcagatga cgtcttggcc aacatgatta gtgaaccaag gatcagttac ggaaacgatg   360
ctctcatgcc atctttgacc gaaacgaaaa ccaccgtgga gctccttccc gtgaatggag   420
agttcagcct ggacgatctc cagccgtggc attcttttgg ggctgactct gtgccagcca   480
acacagaaaa cgaagttgag cctgttgatg cccgccctgc tgccgaccga ggactgacca   540
ctcgaccagg ttctgggttg acaaatatca agacggagga gatctctgaa gtgaagatgg   600
atgcagaatt ccgacatgac tcaggatatg aagttcatca tcaaaaattg gtgttctttg   660
cagaagatgt gggttcaaac aaaggtgcaa tcattggact catggtgggc ggtgttgtca   720
tagcgacagt gatcgtcatc accttggtga tgctgaagaa gaaacagtac acatccattc   780
atcatggtgt ggtggaggtt gacgccgctg tcacccagg ggagcgccac ctgtccaaga    840
tgcagcagaa cggctacgaa aatccaacct acaagttctt gagcagatg cagaactag     899
```

<210> SEQ ID NO 10
<211> LENGTH: 541
<212> TYPE: DNA
<213> ORGANISM: Homo sapiens

<400> SEQUENCE: 10

```
atgctgcccg gtttggcact gctcctgctg ccgcctgga cagctccttc ccgtgaatgg    60
agagttcagc ctggacgatc tccagccgtg gcattcttttt ggggctgact ctgtgccagc   120
caacacagaa aacgaagttg agcctgttga tcccgccct gctgccgacc gaggactgac    180
```

```
cactcgacca ggttctgggt tgacaaatat caagacggag gagatctctg aagtgaagat      240
ggatgcagaa ttccgacatg actcaggata tgaagttcat catcaaaaat tggtgttctt      300
tgcagaagat gtgggttcaa acaaaggtgc aatcattgga ctcatggtgg cggtgttgt       360 catagcgaca gtgatcgtca tcaccttggt gatgctgaag aagaaacagt acacatccat      420
tcatcatggt gtggtggagg ttgacgccgc tgtcaccca gaggagcgcc acctgtccaa       480
gatgcagcag aacggctacg aaaatccaac ctacaagttc tttgagcaga tgcagaacta      540
g                                                                     541

<210> SEQ ID NO 11
<211> LENGTH: 274
<212> TYPE: DNA
<213> ORGANISM: Homo sapiens

<400> SEQUENCE: 11
atgctgcccg gtttggcact gctcctgctg gccgcctgga cggctcgggc gctggaggta       60
cccaatcatt ggactcatgg tgggcggtgt tgtcatagcg acagtgatcg tcatcacctt      120
ggtgatgctg aagaagaaac agtacacatc cattcatcat ggtgtggtgg aggttgacgc      180
cgctgtcacc ccagaggagc gccacctgtc caagatgcag cagaacggct acgaaaatcc      240
aacctacaag ttctttgagc agatgcagaa ctag                                 274

<210> SEQ ID NO 12
<211> LENGTH: 515
<212> TYPE: DNA
<213> ORGANISM: Homo sapiens

<400> SEQUENCE: 12
atgctgcccg gtttggcact gctcctgctg gccgcctgga cggctcgggc gctggaggta       60
cccactgatg gtaatgctgg cctgctggct gaaccccaga ttgccatgtt ctgtggcaga      120
ctgaacatgc acatgaatgt ccagaatggg aagtgggatt cagatccatc agggaccaaa     180
acctgcattg ataccaagga aggcatcctg cagtatatgc agaattccga catgactcag      240
gatatgaagt tcatcatcaa aaattggtgt ctttgcagaa gatgtgggt tcaaacaaag      300 gtgcaatcat tggactcatg gtgggcggtg ttgtcatagc gacagtgatc gtcatcacct      360
tggtgatgct gaagaagaaa cagtacacat ccattcatca tggtgtggtg gaggttgacg      420
ccgctgtcac cccagaggag cgccacctgt ccaagatgca gcagaacggc tacgaaaatc      480
caacctacaa gttctttgag cagatgcaga actag                                515

<210> SEQ ID NO 13
<211> LENGTH: 888
<212> TYPE: DNA
<213> ORGANISM: Homo sapiens

<400> SEQUENCE: 13
atgctgcccg gtttggcact gctcctgctg gccgcctgga cggctcgggc gctggaggta       60
cccactgatg gtaatgctgg cctgctggct gaaccccaga ttgccatgtt ctgtggcaga      120
ctgaacatgc acatgaatgt ccagaatggg aagtgggatt cagatccatc agggaccaaa     180
acctgcattg ataccaagga aggcatcctg cagtattgcc aagaagtcta ccctgaactg      240
cagatcacca atgtggtaga agccaaccaa ccagtgacca tccagaactg gtgcaagcgg      300
ggccgcaagc agtgcaagac ccatcccac tttgtgattc cctaccgctg cttagttggt       360
gagtttgtaa gtgatgccct tctcgttcct gacaagtgca aattcttaca ccaggagagg      420
```

```
atggatgttt gcgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtcggtgg ggcggagcag acacagacta tgcagatggg     660
agtgaagaca aaggtgcaat cattggactc atggtgggcg gtgttgtcat agcgacagtg    720
atcgtcatca ccttggtgat gctgaagaag aaacagtaca catccattca tcatggtgtg    780
gtggaggttg acgccgctgt caccccagag gagcgccacc tgtccaagat gcagcagaac    840
ggctacgaaa atccaaccta caagttcttt gagcagatgc agaactag                888
```

<210> SEQ ID NO 14
<211> LENGTH: 757
<212> TYPE: DNA
<213> ORGANISM: Homo sapiens

<400> SEQUENCE: 14

```
atgctgcccg gtttggcact gctcctgctg gccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga tcagttacgg aaacgatgct ctcatgccat ctttgaccga    240
aacgaaaacc accgtggagc tccttcccgt gaatggagag ttcagcctgg acgatctcca    300
gccgtggcat tcttttgggg ctgactctgt gccagccaac acagaaaacg aagttgagcc    360
tgttgatgcc cgccctgctg ccgaccgagg actgaccact cgaccaggtt ctgggttgac    420
aaatatcaag acggaggaga tctctgaagt gaagatggat gcagaattcc gacatgactc    480
aggatatgaa gttcatcatc aaaaattggt gttctttgca gaagatgtgg gttcaaacaa    540
aggtgcaatc attggactca tggtgggcgg tgttgtcata gcgacagtga tcgtcatcac    600
cttggtgatg ctgaagaaga aacagtacac atccattcat catggtgtgg tggaggttga    660
cgccgctgtc accccagagg agcgccacct gtccaagatg cagcagaacg gctacgaaaa    720
tccaacctac aagttctttg agcagatgca gaactag                            757
```

<210> SEQ ID NO 15
<211> LENGTH: 1879
<212> TYPE: DNA
<213> ORGANISM: Homo sapiens

<400> SEQUENCE: 15

```
atgctgcccg gtttggcact gctcctgctg gccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagcgg    300
ggccgcaagc agtgcaagac ccatccccac tttgtgattc cctaccgctg cttagttggt    360
gagtttgtaa gtgatgccct ctcgttcct gacaagtgca aattcttaca ccaggagagg    420
atggatgttt gcgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
```

-continued

```
gcggaggagg atgactcgga tgtctggtgg ggcggagcag acacagacta tgcagatggg    660
agtgaagaca aagtagtaga agtagcagag gaggaagaag tggctgaggt ggaagaagaa    720
gaagccgatg atgacgagga cgatgaggat ggtgatgagg tagaggaaga ggctgaggaa    780
ccctacgaag aagccacaga gagaaccacc agcattgcca ccaccaccac caccaccaca    840
gagtctgtgg aagaggtggt tcgagaggtg tgctctgaac aagccgagac ggggccgtgc    900
cgagcaatga tctcccgctg gtactttgat gtgactgaag ggaagtgtgc cccattcttt    960
tacggcggat gtggcggcaa ccggaacaac tttgacacag aagagtactg catggccgtg   1020
tgtggcagcg ccattcctac aacagcagcc agtaccctg atgccgttga caagtatctc   1080
gagacacctg gggatgagaa tgaacatgcc catttccaga aagccaaaga gaggcttgag   1140
gccaagcacc gagagagaat gtcccaggtc atgagagaat gggaagaggc agaacgtcaa   1200
gcaaagaact tgcctaaagc tgataagaag gcagttatcc agcatttcca ggagaaagtg   1260
gaatctttgg aacaggaagc agccaacgag agacagcagc tggtggagac acacatggcc   1320
agagtggaag ccatgctcaa tgaccgccgc cgcctggccc tggagaacta catcaccgct   1380
ctgcaggctg ttcctcctcg gcctcgtcac gtgttcaata tgctaaagaa gtatgtacgc   1440
gcagaacaga aggacagaca gcacaccta aagcatttcg agcatgtgcg catggtggat   1500
cccaagaaag ccgctcagat ccggtcccag gttatgacac tcctccgtgt gatttatgag   1560
cgcatgaatc agtctctctc cctgctctac aacgtgcctg cagtggccga ggagattcag   1620
gatgaagttg gtgttctttg cagaagatgt gggttcaaac aaaggtgcaa tcattggact   1680
catggtgggc ggtgttgtca tagcgacagt gatcgtcatc accttggtga tgctgaagaa   1740
gaaacagtac acatccattc atcatggtgt ggtggaggtt gacgccgctg tcaccccaga   1800
ggagcgccac ctgtccaaga tgcagcagaa cggctacgaa aatccaacct acaagttctt   1860
tgagcagatg cagaactag                                                 1879
```

<210> SEQ ID NO 16
<211> LENGTH: 144
<212> TYPE: DNA
<213> ORGANISM: Homo sapiens
<400> SEQUENCE: 16

```
atgctgcccg gtttggcact gctcctgctg gccgcctgga cggctcgggc gctggaggta    60
cccactgatg gtaatgctgg cctgctggct gaaccccaga ttgccatgtt ctgtggcaga   120
aagttctttg agcagatgca gaac                                          144
```

<210> SEQ ID NO 17
<211> LENGTH: 770
<212> TYPE: PRT
<213> ORGANISM: Homo sapiens
<400> SEQUENCE: 17

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60
```

```
Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
                115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
                180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
                260                 265                 270

Ala Thr Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
                340                 345                 350

Thr Gln Glu Pro Leu Ala Arg Asp Pro Val Lys Leu Pro Thr Thr Ala
            355                 360                 365

Ala Ser Thr Pro Asp Ala Val Asp Lys Tyr Leu Glu Thr Pro Gly Asp
            370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
            435                 440                 445

Glu Arg Gln Gln Leu Val Glu Thr His Met Ala Arg Val Glu Ala Met
            450                 455                 460

Leu Asn Asp Arg Arg Arg Leu Ala Leu Glu Asn Tyr Ile Thr Ala Leu
465                 470                 475                 480
```

```
Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctagttctgc atctgctcaa agaacttg                                        28

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 19
atgctgcccg gtttggca                                                     18

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctagttctgc atctgctcaa agaacttg                                           28

<210> SEQ ID NO 21
<211> LENGTH: 310
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
actgctcctg ctggccgcct ggacggctcg ggcgctggag gtacccactg atggtaatgc        60
tggcctgctg gctgaacccc agattgccat gttctgtggc agactgaaca tgcacatgaa       120
tgtccagaat gggaagtggg attcagatcc atcagggacc aaaacctgca ttgataccaa       180
ggaaggcatc ctgcagtatt gccaagaagt ctaccctgaa ctgcagatca ccaatgtggt       240
agaagccaac caaccagtga ccatccagaa ctggtgcaag cggggccgca agcagtgcaa       300
gacccatccc                                                             310

<210> SEQ ID NO 22
<211> LENGTH: 126
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gatgcagaat ccgacatga ctcaggatat gaagttcatc atcaaaaatt ggtgttcttt         60
gcagaagatg tgggttcaaa caaaggtgca atcattggac tcatggtggg cggtgttgtc      120
atagcg                                                                 126

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgctgcccg gtttggca                                                     18

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 24
ctagttctgc atctgctcaa agaacttg                                          28

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgctgcccg gtttggca                                                     18

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctagttctgc atctgctcaa agaacttg                                          28

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgacagagt tacctgcacc                                                   20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctagatataa aattgatgga a                                                 21

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
acatgactca ggatatgaag ttcatcatca aaaattggtg t                           41

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 30
tgccaagaag tctaccctga actgcagatc accaagatgg atgc                    44

<210> SEQ ID NO 31
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gatccacatg actcaggata tgaagttcat catcaaaaat tggtgttctt tgcaa        55

<210> SEQ ID NO 32
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gatcttgcaa agaacaccaa tttttgatga tgaacttcat atcctgagtc atgtg        55

<210> SEQ ID NO 33
<211> LENGTH: 12
<212> TYPE: DNA
<213> ORGANISM: Homo sapiens

<400> SEQUENCE: 33
gacagtcagt ct                                                       12

<210> SEQ ID NO 34
<211> LENGTH: 10
<212> TYPE: DNA
<213> ORGANISM: Homo sapiens

<400> SEQUENCE: 34
ggcactgctc                                                          10

<210> SEQ ID NO 35
<211> LENGTH: 10
<212> TYPE: DNA
<213> ORGANISM: Homo sapiens

<400> SEQUENCE: 35
caccgctctg                                                          10

<210> SEQ ID NO 36
<211> LENGTH: 10
<212> TYPE: DNA
<213> ORGANISM: Homo sapiens

<400> SEQUENCE: 36
ataccaagga                                                          10

<210> SEQ ID NO 37
<211> LENGTH: 10
<212> TYPE: DNA
<213> ORGANISM: Homo sapiens

<400> SEQUENCE: 37
accaaggatc                                                                10

<210> SEQ ID NO 38
<211> LENGTH: 11
<212> TYPE: DNA
<213> ORGANISM: Homo sapiens

<400> SEQUENCE: 38
cctgcagtat t                                                              11

<210> SEQ ID NO 39
<211> LENGTH: 11
<212> TYPE: DNA
<213> ORGANISM: Homo sapiens

<400> SEQUENCE: 39
tgcagaattc c                                                              11

<210> SEQ ID NO 40
<211> LENGTH: 22
<212> TYPE: DNA
<213> ORGANISM: Homo sapiens

<400> SEQUENCE: 40
gcagatggga gtgaagacaa ag                                                  22

<210> SEQ ID NO 41
<211> LENGTH: 20
<212> TYPE: DNA
<213> ORGANISM: Homo sapiens

<400> SEQUENCE: 41
agatgggagt gaagacaaag                                                     20

<210> SEQ ID NO 42
<211> LENGTH: 22
<212> TYPE: DNA
<213> ORGANISM: Homo sapiens

<400> SEQUENCE: 42
agatgtgggt tcaaacaaag gt                                                  22

METHODS OF DIAGNOSING AND TREATING ALZHEIMER'S DISEASE

CROSS-REFERENCE

This application is the U.S. National Stage application of International Application No. PCT/US2018/030520, filed on May 1, 2018, and claims benefit of U.S. Provisional Patent Application No. 62/500,270 filed on May 2, 2017, which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 1, 2018, is named 42256-722_601_SL.txt and is 28,069 bytes in size.

BRIEF SUMMARY

Provided herein, in some embodiments, are methods for evaluating an individual for risk of developing a disease or disorder characterized by unwanted accumulation of amyloid beta protein comprising:
  (a) measuring an expression profile or an activity profile of one or more non-classical variant(s) of an amyloid beta precursor protein (APP) gene from a biological sample from the individual;
  (b) comparing the expression profile or the activity profile of the one or more non-classical variant(s) to a reference expression profile or activity profile of the one or more non-classical variant(s) derived from a cohort of control individuals; and
  (c) identifying the individual as having or not having a risk factor for developing the disease or disorder characterized by unwanted accumulation of amyloid beta protein based on a comparison of the expression profile or the activity profile measured in step (a) to the reference expression profile or activity profile of the cohort of control individuals.

In some embodiments, the expression profile is expression level of the one or more non-classical variant(s). In some embodiments, the activity profile is activity level of the one or more non-classical variant(s). In some embodiments, the expression profile is expression of a set of different non-classical variants. In some embodiments, the activity profile is activity of a set of different non-classical variants. In some embodiments, methods further comprise measuring the expression profile by a method comprising long-read sequencing of the biological sample from the individual. In some embodiments, the long-read sequencing is RNA sequencing (RNA-seq). In some embodiments, the long-read sequencing is DNA sequencing. In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, generation of the one or more non-classical variant(s) involves transcription. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, Alzheimer's disease is familial Alzheimer's disease (FAD) or sporadic Alzheimer's disease. In some embodiments, the biological sample is collected from blood or cerebrospinal fluid. In some embodiments, the biological sample comprises RNA, DNA, or protein. In some embodiments, the DNA is genomic DNA, extrachromosomal DNA, or circular DNA. In some embodiments, the DNA is genomic DNA. In some embodiments, methods further comprise isolating and purifying RNA or DNA from the biological sample prior to the long-read sequencing. In some embodiments, methods further comprise reverse transcribing RNA to cDNA prior to the long-read sequencing. In some embodiments, an average read length for the long-read sequencing is at least 5000 bases. In some embodiments, measuring the expression profile comprises quantifying the expression level of the one or more non-classical variant(s) by a method comprising counting a number of reads that map to a sequence of the one or more non-classical variant(s). In some embodiments, measuring the expression profile comprises a method comprising binding of one or more probe(s) to the one or more non-classical variant(s). In some embodiments, the expression profile comprises quantifying the expression level by a method comprising quantitative polymerase chain reaction (qPCR). In some embodiments, the one or more probe(s) are selected from polynucleotides or polypeptides. In some embodiments, the one or more probe(s) hybridize to RNA or DNA within the biological sample. In some embodiments, the one or more probe(s) hybridize to a range of about 35 to about 50 nucleotides in the RNA or DNA. In some embodiments, methods further comprise capturing the one or more non-classical variant(s) from the biological sample on a solid support prior to contacting the one or more non-classical variant(s) with the one or more probe(s). In some embodiments, the one or more non-classical variant(s) is detected by in situ hybridization or immunological hybridization. In some embodiments, the in situ hybridization is chromogenic in situ hybridization or fluorescence in situ hybridization. In some embodiments, measuring binding of the one or more probe(s) to the one or more non-classical variant(s) further comprises a pull-down assay. In some embodiments, the one or more probe(s) for the pull-down assay are designed to hybridize to a portion or all of exon 1, 2, 3, 4, 5, 6, 7, 8, 9, 10, 11, 12, 13, 14, 15, 16, 17, 18, or combinations thereof. In some embodiments, a probe of the one or more probe(s) is labeled using an affinity tag. In some embodiments, the affinity tag is biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione. In some embodiments, the one or more probe(s) bind to one or more protein(s) encoded by the one or more non-classical variant(s). In some embodiments, the one or more probe(s) comprise an antibody or fragment thereof. In some embodiments, a probe of the one or more probe(s) is labeled using a fluorochrome or a radioactive isotope. In some embodiments, the unwanted accumulation of amyloid beta protein is plaque depositions comprising a portion of or all amyloid beta protein, or accumulation of soluble amyloid beta protein.

Provided herein, in some embodiments, are methods of treating a disease or disorder characterized by unwanted accumulation of amyloid beta protein in an individual in need thereof, comprising: administering to the individual an agent that inhibits activity of one or more non-classical variant(s) of an APP gene. In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, generation of the one or more non-classical variant(s) involves transcription. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, Alzheimer's disease is familial Alzheimer's disease (FAD) or sporadic Alzheimer's disease. In some embodiments, the agent that inhibits the activity of APP is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. In some embodiments, the antibody binds to a protein encoded by the one or more non-classical variant(s). In some embodiments, the antisense oligonucleotide targets RNA or DNA of APP. In some embodiments, the RNA is mRNA. In some embodiments, the DNA is genomic DNA. In some embodiments, the protein is encoded by the one or more non-classical variant(s) comprising a sequence as set forth in SEQ ID NO: 1, 2, 3, 4, 5, 6, 7, 8, 9, 10, 11, 12, 13, 14, 15, or 16. In some embodiments, the agent does not inhibit activity of a wild-type amyloid beta precursor protein gene or protein thereof. In some embodiments, the unwanted accumulation of amyloid beta protein is plaque depositions comprising a portion of or all amyloid beta protein, or accumulation of soluble amyloid beta protein. In some embodiments, the unwanted accumulation of amyloid beta protein results from increased APP associated with the one or more non-classical variant(s) of APP gene.

Provided herein, in some embodiments, are methods of diagnosing and treating a disease or disorder characterized by unwanted accumulation of amyloid beta protein in an individual in need thereof, comprising:
  (a) identifying the individual as having the disease or disorder characterized by unwanted accumulation of amyloid beta protein if binding of one or more probe(s) to one or more non-classical variant(s) of an APP gene is measured; and
  (b) administering to the individual having an expression profile or an activity profile of the one or more non-classical variant(s) an agent that inhibits activity of the one or more non-classical variant(s).

In some embodiments, methods further comprise contacting a biological sample from the individual with the one or more probe(s) that hybridize to the one or more non-classical variant(s). In some embodiments, methods further comprise measuring binding of the one or more probe(s) to the one or more non-classical variant(s). In some embodiments, the expression profile is expression level of the one or more non-classical variant(s). In some embodiments, the activity profile is activity level of the one or more non-classical variant(s). In some embodiments, methods further comprise quantifying the expression level of the one or more non-classical variant(s) by a method comprising quantitative polymerase chain reaction (qPCR). In some embodiments, the expression profile is expression of a set of different non-classical variants. In some embodiments, the activity profile is activity of a set of different non-classical variants. In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, generation of the one or more non-classical variant(s) involves transcription. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, Alzheimer's disease is familial Alzheimer's disease (FAD) or sporadic Alzheimer's disease. In some embodiments, the biological sample is collected from blood or cerebrospinal fluid. In some embodiments, the biological sample comprises RNA, DNA, or protein. In some embodiments, the DNA is genomic DNA, extrachromosomal DNA, or circular DNA. In some embodiments, the DNA is genomic DNA. In some embodiments, the one or more probe(s) are selected from polynucleotides or polypeptides. In some embodiments, the one or more probe(s) hybridize to RNA or DNA within the biological sample. In some embodiments, the one or more probe(s) hybridize to a range of about 35 to about 50 nucleotides of the RNA or DNA. In some embodiments, methods further comprise capturing the one or more non-classical variant(s) from the biological sample prior to contacting the one or more non-classical variant(s) with the one or more probe(s). In some embodiments, the one or more non-classical variant(s) is detected by in situ hybridization or immunological hybridization. In some embodiments, the in situ hybridization is chromogenic in situ hybridization or fluorescence in situ hybridization. In some embodiments, methods further comprise measuring binding of the one or more probe(s) to the one or more non-classical variant(s) further comprises a pull-down assay. In some embodiments, the one or more probe(s) for the pull-down assay are designed to hybridize to a portion or all of exon 1, 2, 3, 4, 5, 6, 7, 8, 9, 10, 11, 12, 13, 14, 15, 16, 17, 18, or combinations thereof. In some embodiments, a probe in the one or more probe(s) is labeled using an affinity tag. In some embodiments, the affinity tag is biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione. In some embodiments, the one or more probe(s) bind to one or more protein(s) encoded by the one or more non-classical variant(s). In some embodiments, the one or more probe(s) comprise an antibody or fragment thereof. In some embodiments, a probe of the one or more probe(s) is labeled using a fluorochrome or a radioactive isotope. In some embodiments, the agent that inhibits the activity of APP is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. In some embodiments, the antisense oligonucleotide targets RNA or DNA of APP. In some embodiments, the RNA is mRNA. In some embodiments, the DNA is genomic DNA.

Provided herein, in some embodiments, are methods of diagnosing and treating a disease or disorder characterized by unwanted accumulation of amyloid beta protein in an individual in need thereof, comprising:
 (a) identifying the individual as having the disease or disorder characterized by unwanted accumulation of amyloid beta protein if an expression profile of one or more non-classical variant(s) of an APP gene is measured by a method comprising long-read sequencing of a biological sample from the individual; and
 (b) administering to the individual having the expression profile of the one or more non-classical variant(s) an agent that inhibits activity of the one or more non-classical variant(s).

In some embodiments, the expression profile is expression level of the one or more non-classical variant(s). In some embodiments, the long-read sequencing is RNA sequencing (RNA-seq). In some embodiments, the long-read sequencing is DNA sequencing. In some embodiments, methods further comprise quantifying the expression level of the one or more non-classical variant(s) by a method comprising counting a number of reads that map to a sequence of the one or more non-classical variant(s). In some embodiments, the expression profile is expression of a set of different non-classical variants. In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, generation of the one or more non-classical variant(s) involves transcription. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, Alzheimer's disease is familial Alzheimer's disease (FAD) or sporadic Alzheimer's disease. In some embodiments, the biological sample is collected from blood or cerebrospinal fluid. In some embodiments, the biological sample comprises RNA or DNA. In some embodiments, the DNA is genomic DNA, extrachromosomal DNA, or circular DNA. In some embodiments, the DNA is genomic DNA. In some embodiments, methods further comprise isolating and purifying RNA or DNA from the biological sample prior to the long-read sequencing. In some embodiments, methods further comprise reverse transcribing RNA to cDNA prior to the long-read sequencing. In some embodiments, an average read length for the long-read sequencing is at least 5000 bases. In some embodiments, the agent that inhibits the activity of APP is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. In some embodiments, the unwanted accumulation of amyloid beta protein is plaque depositions comprising a portion of or all amyloid beta protein, or accumulation soluble amyloid beta protein. In some embodiments, the antisense oligonucleotide targets RNA or DNA of APP. In some embodiments, the RNA is mRNA. In some embodiments, the DNA is genomic DNA.

Provided herein, in some embodiments, are methods of detecting one or more non-classical variant(s) of an APP gene in an individual in need thereof, comprising: detecting an expression profile of the one or more non-classical variant(s) of the APP gene in a biological sample from the individual by a method comprising long-read sequencing of the biological sample. In some embodiments, the expression profile is expression level of the one or more non-classical variant(s). In some embodiments, the expression profile is expression of a set of different non-classical variants. In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, generation of the one or more non-classical variant(s) involves transcription. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the expression profile of the one or more non-classical variant(s) is associated with a disease or disorder characterized by unwanted accumulation of amyloid beta protein. In some embodiments, the unwanted accumulation of amyloid beta protein is plaque depositions comprising a portion of or all amyloid beta protein, or accumulation of soluble amyloid beta protein. In some embodiments, the expression profile of the one or more non-classical variant(s) is associated with unwanted accumulation of amyloid beta protein, and wherein the individual does not have a disease or disorder. In some embodiments, the disease or disorder is Alzheimer's disease. In some embodiments, the biological sample is collected from blood or cerebrospinal fluid. In some embodiments, the biological sample comprises RNA or DNA. In some embodiments, the DNA is genomic DNA, extrachromosomal DNA, or circular DNA. In some embodiments, the DNA is genomic DNA. In some embodiments, methods further comprise isolating and purifying RNA or DNA from the biological sample prior to the long-read sequencing. In some embodiments, methods further comprise reverse transcribing RNA to cDNA prior to the long-read sequencing. In some embodiments, an average read length for the long-read sequencing is at least 5000 bases. In some embodiments, the long-read sequencing is RNA sequencing (RNA-seq). In some embodiments, the long-read sequencing is DNA sequencing. In some embodiments, detecting the expression profile comprises quantifying the expression level of the one or more non-classical variant(s) by a method comprising counting a number of reads that map to a sequence of the one or more non-classical variant(s). In some embodiments, the individual is suspected of having or being predisposed to Alzheimer's disease.

Provided herein, in some embodiments, are methods of detecting one or more non-classical variant(s) of an APP gene in an individual in need thereof, comprising: detecting an expression profile or an activity profile of the one or more non-classical variant of the APP gene in a biological sample from the individual by a method comprising binding of one or more probe(s) to the one or more non-classical variant(s). In some embodiments, the expression profile is expression level of the one or more non-classical variant(s). In some embodiments, the activity profile is activity level of the one or more non-classical variant(s). In some embodiments, the expression profile is expression of a set of different non-classical variants. In some embodiments, the activity profile is activity of a set of different non-classical variants. In some embodiments, detecting the expression profile comprises quantifying expression level by a method comprising quantitative polymerase chain reaction (qPCR). In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, generation of the one or more non-classical variant(s) involves transcription. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the expression profile or the activity level of the one or more non-classical variant(s) is associated with a disease or disorder characterized by unwanted accumulation of amyloid beta protein. In some embodiments, the unwanted accumulation of amyloid beta protein is plaque depositions comprising a portion of or all amyloid beta protein, or accumulation of soluble amyloid beta protein. In some embodiments, the expression profile or the activity profile of the one or more non-classical variant(s) is associated with unwanted accumulation of amyloid beta protein, and wherein the individual does not have a disease or disorder. In some embodiments, the disease or disorder is Alzheimer's disease. In some embodiments, the biological sample is collected from blood or cerebrospinal fluid. In some embodiments, the biological sample comprises RNA, DNA, or protein. In some embodiments, the DNA is genomic DNA, extrachromosomal DNA, or circular DNA. In some embodiments, the DNA is genomic DNA. In some embodiments, the one or more probe(s) are selected from polynucleotides or polypeptides. In some embodiments, the one or more probe(s) hybridize to RNA or DNA within the biological sample. In some embodiments, the one or more probe(s) hybridize to a range of about 35 to about 50 nucleotides of the RNA or DNA. In some embodiments, methods further comprise capturing the one or more non-classical variant(s) from the biological sample on a solid support prior to contacting the one or more non-classical variant with the one or more probe(s). In some embodiments, the one or more non-classical variant(s) is detected by in situ hybridization or immunological hybridization. In some embodiments, the in situ hybridization is chromogenic in situ hybridization or fluorescence in situ hybridization. In some embodiments, detecting binding of the one or more probe(s) to the one or more non-classical variant(s) further comprises a pull-down assay. In some embodiments, the one or more probe(s) for the pull-down assay are designed to hybridize to a portion or all of exon 1, 2, 3, 4, 5, 6, 7, 8, 9, 10, 11, 12, 13, 14, 15, 16, 17, 18, or combinations thereof. In some embodiments, a probe in the one or more probe(s) is labeled using an affinity tag. In some embodiments, the affinity tag is biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione. In some embodiments, the one or more probe(s) bind to one or more protein(s) encoded by the one or more non-classical variant(s). In some embodiments, the one or more probe(s) comprise an antibody or fragment thereof. In some embodiments, a probe in the one or more probe(s) is labeled using a fluorochrome or a radioactive isotope.

Provided herein, in some embodiments, are methods of diagnosing a disease or disorder in an individual characterized by unwanted accumulation of amyloid beta protein, comprising: identifying the individual as having the disease or disorder characterized by unwanted accumulation of amyloid beta protein by comparing an expression profile of one or more non-classical variant(s) of an APP gene to a reference expression profile of the one or more non-classical variant(s) derived from a cohort of control individuals, wherein the expression profile of the one or more non-classical variant(s) is measured by a method comprising long-read sequencing of a biological sample from the individual; and wherein the expression profile of the one or more non-classical variant(s) is associated with the disease or disorder. In some embodiments, the expression profile is expression level of the one or more non-classical variant(s). In some embodiments, the expression profile is expression of a set of different non-classical variants. In some embodiments, the long-read sequencing is RNA sequencing (RNA-seq). In some embodiments, the long-read sequencing is DNA sequencing. In some embodiments, methods further comprise quantifying the expression level of the one or more non-classical variant(s) by a method comprising counting a number of reads that map to a sequence of the one or more non-classical variant(s). In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, generation of the one or more non-classical variant(s) involves transcription. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, Alzheimer's disease is familial Alzheimer's disease (FAD) or sporadic Alzheimer's disease. In some embodiments, the individual is suspected of having or being predisposed to Alzheimer's disease. In some embodiments, the biological sample is collected from blood or cerebrospinal fluid. In some embodiments, methods further comprise isolating and purifying RNA or DNA from the biological sample prior to the long-read sequencing. In some embodiments, methods further comprise reverse transcribing RNA to cDNA prior to the long-read sequencing. In some embodiments, an average read length for the long-read sequencing is at least 5000 bases. In some embodiments, the unwanted accumulation of amyloid beta protein is plaque depositions comprising a portion of or all amyloid beta protein, or accumulation of soluble amyloid beta protein.

Provided herein, in some embodiments, are methods of diagnosing a disease or disorder in an individual characterized by unwanted accumulation of amyloid beta protein, comprising: identifying the individual as having the disease or disorder characterized by unwanted accumulation of amyloid beta protein by comparing an expression profile or an activity profile of one or more non-classical variant(s) of an APP gene to a reference expression profile of the one or more non-classical variant(s) derived from a cohort of control individuals, wherein the expression profile or the activity profile of the one or more non-classical variant(s) is measured by a method comprising binding of one or more probe(s) to a biological sample from the individual; and wherein the expression profile or the activity profile of the one or more non-classical variant(s) is associated with the disease or disorder. In some embodiments, the expression profile is expression level of the one or more non-classical variant(s). In some embodiments, the activity profile is activity level of the one or more non-classical variant(s). In some embodiments, the expression profile is expression of a set of different non-classical variants. In some embodiments, the activity profile is activity of a set of different non-classical variants. In some embodiments, methods further comprise quantifying the expression level by a method comprising quantitative polymerase chain reaction (qPCR). In some embodiments, methods further comprise capturing the one or more non-classical variant(s) from the biological sample on a solid support prior to contacting the one or more non-classical variant(s) with the one or more probe(s). In some embodiments, the one or more non-classical variant(s) is detected by in situ hybridization or immunological hybridization. In some embodiments, the in situ hybridization is chromogenic in situ hybridization or fluorescence in situ hybridization. In some embodiments, binding of the one or more probe(s) to the one or more non-classical variant(s) further comprises a pull-down assay. In some embodiments, the one or more probe(s) for the pull-down assay are designed to hybridize to a portion or all of exon 1, 2, 3, 4, 5, 6, 7, 8, 9, 10, 11, 12, 13, 14, 15, 16, 17, 18, or combinations thereof. In some embodiments, a probe in the one or more probe(s) is labeled using an affinity tag. In some embodiments, the affinity tag is biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione. In some embodiments, the one or more probe(s) are selected from polynucleotides or polypeptides. In some embodiments, the one or more probe(s) hybridize to RNA or DNA within the biological sample. In some embodiments, the one or more probe(s) hybridize to a range of about 35 to about 50 nucleotides of the RNA or DNA. In some embodiments, the one or more probe(s) bind to one or more protein(s) encoded by the one or more non-classical variant(s). In some embodiments, the one or more probe(s) comprise an antibody or fragment thereof. In some embodiments, a probe in the one or more probe(s) is labeled using a fluorochrome or a radioactive isotope. In some embodiments, the unwanted accumulation of amyloid beta protein is plaque depositions comprising amyloid beta protein, or accumulation of soluble amyloid beta protein.

Provided herein, in some embodiments, are kits for detecting one or more non-classical variant(s) of an APP gene in a biological sample of an individual, the kit comprising:
(a) one or more probe(s) that hybridize to the one or more non-classical variant(s) of the APP gene or protein thereof; and
(b) a detecting reagent for examining binding of the one or more probe(s) with the one or more non-classical variant(s) of the APP gene or protein thereof.

In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, generation of the one or more non-classical variant(s) involves transcription. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the one or more probe(s) are selected from polynucleotides or polypeptides. In some embodiments, the one or more probe(s) hybridize to RNA or DNA within the biological sample. In some embodiments, the one or more probe(s) bind to one or more protein(s) encoded by the one or more non-classical variant(s). In some embodiments, the one or more probe(s) comprise an antibody or fragment thereof. In some embodiments, a probe in the one or more probe(s) is labeled using a fluorochrome or a radioactive isotope. In some embodiments, a probe in the one or more probe(s) is labeled using an affinity tag. In some embodiments, the affinity tag is biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione. In some embodiments, the detecting reagent binds to the one or more probe(s). In some embodiments, the detecting reagent comprises a fluorescent or a radioactive label. In some embodiments, the individual is suspected of having or being predisposed to Alzheimer's disease.

Provided herein, in some embodiments, are in vitro methods of screening for a therapeutic agent for treating a disease or disorder characterized by unwanted accumulation of amyloid beta protein, comprising:
(a) contacting a cell that expresses a non-classical variant of an APP gene with a test agent;
(b) detecting inhibition of expression of the non-classical variant of the APP gene compared to a control; and
(c) identifying the test agent as a therapeutic agent if the test agent inhibits expression of the non-classical variant of the APP gene compared to the control.

In some embodiments, expression of the non-classical variant of the APP gene is measured by qPCR or gel electrophoresis. In some embodiments, detecting inhibition of expression comprises measuring protein expression of a protein encoded by the non-classical variant of the APP gene. In some embodiments, the protein expression is measured by Western blot, enzyme-linked immunosorbent assays (ELISA), or chromatography.

Provided herein, in some embodiments, are in vitro methods of screening for a therapeutic agent for treating a disease or disorder characterized by unwanted accumulation of amyloid beta protein, comprising:
  (a) contacting a cell that expresses a non-classical variant of an APP gene with a test agent;
  (b) detecting inhibition of activity of the non-classical variant of the APP gene as compared to a control; and
  (c) identifying the test agent as the therapeutic agent if the test agent inhibits the activity of the non-classical variant of the APP gene as compared to the control.

In some embodiments, the activity of the non-classical variant comprises accumulation of amyloid beta protein. In some embodiments, the accumulation of amyloid beta protein is measured by a method comprising Western blot, enzyme-linked immunosorbent assays (ELISA), or chromatography. In some embodiments, the activity of the non-classical variant is measured by a method comprising a fluorescence assay, a luciferase assay, or an enzymatic assay.

Provided herein, in some embodiments, are in vitro methods of screening for a therapeutic agent for treating a disease or disorder characterized by unwanted accumulation of amyloid beta protein, comprising:
  (a) contacting a cell that expresses a non-classical variant of an APP gene with a test agent;
  (b) detecting binding of the test agent to the non-classical variant of the APP gene; and
  (c) identifying the test agent as the therapeutic agent if the test agents binds to the non-classical variant of the APP gene.

In some embodiments, methods further comprise detecting binding by a method comprising a radioactive binding assay, a fluorescence binding assay, an enzyme-linked immunosorbent assay (ELISA), a kinetic exclusion assay, or a crystallography assay. In some embodiments, the non-classical variant comprises a portion or all of exon 1, 2, 3, 4, 5, 6, 7, 8, 9, 10, 11, 12, 13, 14, 15, 16, 17, 18, or combinations thereof. In some embodiments, the non-classical variant does not comprise exon 8. In some embodiments, one or more exon(s) in the non-classical variant is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, the non-classical variant comprises a sequence as set forth in SEQ ID NO: 1, 2, 3, 4, 5, 6, 7, 8, 9, 10, 11, 12, 13, 14, 15, or 16. In some embodiments, the therapeutic agent is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. In some embodiments, the antisense oligonucleotide targets RNA or DNA of APP. In some embodiments, the RNA is mRNA. In some embodiments, the DNA is genomic DNA.

Provided herein, in some embodiments, are methods of identifying one or more non-classical variant(s) of an APP gene, comprising:
  (a) isolating RNA from a cell from an individual with Alzheimer's disease;
  (b) reverse transcribing the RNA into cDNA;
  (c) hybridizing the cDNA with a probe to detect APP; and
  (d) sequencing the cDNA that was detected by step (c).

In some embodiments, the probe comprises a sequence as set forth in SEQ ID NO: 21. In some embodiments, the cell is a neuron. In some embodiments, methods further comprise comparing cDNA isolated from RNA of an individual without Alzheimer's disease.

Provided herein, in some embodiments, are therapeutic agents identified by any of the methods described herein.

Provided herein, in some embodiments, are methods of treating a disease or disorder characterized by unwanted accumulation of amyloid beta protein in an individual in need thereof, comprising: administering to the individual an agent that inhibits generation of one or more non-classical variant(s) of an APP gene. In some embodiments, the generation of the one or more non-classical variant(s) involves transcription. In some embodiments, the agent edits RNA. In some embodiments, the agent edits DNA. In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, Alzheimer's disease is familial Alzheimer's disease (FAD) or sporadic Alzheimer's disease. In some embodiments, the unwanted accumulation of amyloid beta protein is plaque depositions comprising a portion of or all amyloid beta protein, or accumulation of soluble amyloid beta protein. In some embodiments, the unwanted accumulation of amyloid beta protein results from increased APP associated with the one or more non-classical variant(s) of APP gene.

Provided herein, in some embodiments, are methods of treating a disease or disorder characterized by unwanted accumulation of amyloid beta protein in an individual in need thereof, comprising: administering to the individual a therapeutically-effective amount of a composition comprising: (a) a nuclease; and (b) a guide nucleic acid comprising a region that is complementary to a target nucleic acid, wherein the target nucleic acid is a non-classical variant of APP. In some embodiments, the nuclease is a CRISPR-associated protein (Cas). In some embodiments, the Cas protein is Cas9. In some embodiments, the Cas protein is Cas13. In some embodiments, the target nucleic acid is RNA of the non-classical variant of APP. In some embodiments, the target nucleic acid is DNA of the non-classical variant of APP. In some embodiments, the non-classical variant comprises a portion or all of exon 1, 2, 3, 4, 5, 6, 7, 8, 9, 10, 11, 12, 13, 14, 15, 16, 17, 18, or combinations thereof. In some embodiments, the non-classical variant comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, the non-classical variant does not comprise exon 8. In some embodiments, one or more exon(s) in the non-classical variant is rearranged as compared to a control. In some embodiments, the non-classical variant comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, Alzheimer's disease is familial Alzheimer's disease (FAD) or sporadic Alzheimer's disease. In some embodiments, the unwanted accumulation of amyloid beta protein is plaque depositions comprising a portion of or all amyloid beta protein, or accumulation of soluble amyloid beta protein. In some embodiments, unwanted accumulation of amyloid beta protein results from increased APP associated with the non-classical variant of APP gene.

Provided herein, in some embodiments, are methods method of detecting one or more non-classical variant(s) of an APP gene in an individual in need thereof, comprising: detecting an expression profile of the one or more non-classical variant(s) of the APP gene in a biological sample from the individual by (a) long-read sequencing of RNA or DNA encoding for the one or more non-classical variant(s), or (b) binding of one or more probe(s) to the one or more non-classical variant(s). In some embodiments, the expression profile is expression level of the one or more non-classical variant(s) or expression of a set of different non-classical variants. In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the expression profile of the one or more non-classical variant(s) is associated with a disease or disorder characterized by unwanted accumulation of amyloid beta protein. In some embodiments, the unwanted accumulation of amyloid beta protein is plaque depositions comprising a portion of or all amyloid beta protein, or accumulation of soluble amyloid beta protein. In some embodiments, the expression profile of the one or more non-classical variant(s) is associated with unwanted accumulation of amyloid beta protein, and wherein the individual does not have a disease or disorder. In some embodiments, the biological sample is blood or cerebrospinal fluid. In some embodiments, the DNA is genomic DNA, extrachromosomal DNA, or circular DNA. In some embodiments, detecting the expression profile comprises quantifying the expression level of the one or more non-classical variant(s) by a method comprising counting a number of reads that map to a sequence of the one or more non-classical variant(s). In some embodiments, the individual is suspected of having or being predisposed to Alzheimer's disease. In some embodiments, the one or more probe(s) hybridize to RNA or DNA encoding for the one or more non-classical variant(s) within the biological sample. In some embodiments, the one or more probe(s) hybridize to an intraexonic junction between exon 1 and exon 11, exon 1 and exon 14, exon 2 and exon 17, exon 2 and exon 14, exon 2 and exon 18, exon 2 and exon 16, exon 3 and exon 16, exon 3 and exon 14, exon 3 and exon 17, exon 6 and exon 17, exon 6 and exon 18, exon 3 and exon 9, exon 2 and exon 9, exon 9 and exon 16 and exon 18, exon 6 and exon 12, exon 5 and exon 16, or exon 16 and exon 17. In some embodiments, the one or more non-classical variant(s) is detected by in situ hybridization or immunological hybridization. In some embodiments, detecting binding of the one or more probe(s) to the one or more non-classical variant(s) further comprises a pull-down assay. In some embodiments, the one or more probe(s) for the pull-down assay are designed to hybridize to a portion or all of exon 1, 2, 3, 4, 5, 6, 7, 8, 9, 10, 11, 12, 13, 14, 15, 16, 17, 18, or combinations thereof. In some embodiments, a probe in the one or more probe(s) is labeled using an affinity tag. In some embodiments, the one or more probe(s) bind to one or more protein(s) encoded by the one or more non-classical variant(s). In some embodiments, the one or more probe(s) comprise an antibody or fragment thereof. In some embodiments, a probe in the one or more probe(s) is labeled using a fluorochrome or a radioactive isotope. In some embodiments, methods further comprise administering an agent that inhibits activity of the one or more non-classical variant(s). In some embodiments, the agent that inhibits the activity of APP is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. In some embodiments, the antisense oligonucleotide targets RNA or DNA of APP. In some embodiments, methods further comprise administering a cholinesterase inhibitor, N-methyl-D-aspartate (NMDA) receptor antagonist, or an anti-amyloid beta antibody. In some embodiments, the cholinesterase inhibitor is selected from the group consisting of Donepezil, Galantamine, and Rivastigmine. In some embodiments, the NMDA receptor antagonist is memantine. In some embodiments, the anti-amyloid beta antibody is selected from the group consisting of Bapineuzumab, Solanezumab, Gantenerumab, Crenezumab, BAN2401, Ponezumab, and Aducanumab.

Provided herein, in some embodiments, are methods for evaluating an individual for risk of developing a disease or disorder characterized by unwanted accumulation of amyloid beta protein comprising:
  (a) measuring an expression profile or an activity profile of one or more non-classical variant(s) of an amyloid beta precursor protein (APP) gene from a biological sample from the individual;
  (b) comparing the expression profile or the activity profile of the one or more non-classical variant(s) to a reference expression profile or activity profile of the one or more non-classical variant(s) derived from a cohort of control individuals; and
  (c) identifying the individual as having or not having a risk factor for developing the disease or disorder characterized by unwanted accumulation of amyloid beta protein based on a comparison of the expression profile or the activity profile measured in step (a) to the reference expression profile or activity profile of the cohort of control individuals.

Provided herein, in some embodiments, are methods of diagnosing a disease or disorder characterized by unwanted accumulation of amyloid beta protein in an individual in need thereof, comprising:
  (a) measuring an expression profile or an activity profile of one or more non-classical variant(s) of an amyloid beta precursor protein (APP) gene from a biological sample from the individual by (i) long-read sequencing of RNA or DNA encoding for the one or more non-classical variant(s), or (ii) binding of one or more probe(s) to the one or more non-classical variant(s); and (b) identifying the individual as having the disease or disorder characterized by unwanted accumulation of amyloid beta protein by comparing the expression profile or the activity profile of one or more non-classical variant(s) of an APP gene to a reference expression profile or an activity profile of the one or more non-classical variant(s) derived from a cohort of control individuals, wherein the expression profile or the activity profile of the one or more non-classical variant(s) is associated with the disease or disorder.

In some embodiments, the expression profile is expression level of the one or more non-classical variant(s), and wherein the activity profile is activity level of the one or more non-classical variant(s). In some embodiments, the expression profile is expression of a set of different non-classical variants, and wherein the activity profile is activity of a set of different non-classical variants. In some embodiments, methods further comprise measuring the expression profile by a method comprising long-read sequencing of RNA or DNA from the biological sample from the individual, wherein the RNA or DNA encodes the one or more non-classical variant(s). In some embodiments, measuring the expression profile comprises quantifying the expression level of the one or more non-classical variant(s) by a method comprising counting a number of reads that map to a sequence of the one or more non-classical variant(s). In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, the Alzheimer's disease is familial Alzheimer's disease (FAD) or sporadic Alzheimer's disease. In some embodiments, the biological sample is blood or cerebrospinal fluid. In some embodiments, the biological sample comprises RNA, DNA, or protein encoding for the one or more non-classical variant(s). In some embodiments, the DNA is genomic DNA, extrachromosomal DNA, or circular DNA. In some embodiments, measuring the expression profile comprises a method comprising binding of one or more probe(s) to the one or more non-classical variant(s). In some embodiments, the one or more probe(s) hybridize to an intraexonic junction between exon 1 and exon 11, exon 1 and exon 14, exon 2 and exon 17, exon 2 and exon 14, exon 2 and exon 18, exon 2 and exon 16, exon 3 and exon 16, exon 3 and exon 14, exon 3 and exon 17, exon 6 and exon 17, exon 6 and exon 18, exon 3 and exon 9, exon 2 and exon 9, exon 16 and exon 18, exon 6 and exon 12, exon 5 and exon 16, or exon 16 and exon 17. In some embodiments, measuring the expression profile comprises quantifying the expression level by a method comprising quantitative polymerase chain reaction (qPCR). In some embodiments, the one or more probe(s) hybridize to RNA or DNA encoding for the one or more non-classical variant(s) within the biological sample. In some embodiments, the one or more non-classical variant(s) is detected by in situ hybridization or immunological hybridization. In some embodiments, measuring binding of the one or more probe(s) to the one or more non-classical variant(s) further comprises a pull-down assay. In some embodiments, the one or more probe(s) for the pull-down assay are designed to hybridize to a portion or all of exon 1, 2, 3, 4, 5, 6, 7, 8, 9, 10, 11, 12, 13, 14, 15, 16, 17, 18, or combinations thereof. In some embodiments, a probe of the one or more probe(s) is labeled using an affinity tag. In some embodiments, the one or more probe(s) bind to one or more protein(s) encoded by the one or more non-classical variant(s). In some embodiments, the one or more probe(s) comprise an antibody or fragment thereof. In some embodiments, a probe of the one or more probe(s) is labeled using a fluorochrome or a radioactive isotope. In some embodiments, the unwanted accumulation of amyloid beta protein is plaque depositions comprising a portion of or all amyloid beta protein, or accumulation of soluble amyloid beta protein. In some embodiments, methods further comprise administering an agent that inhibits activity of the one or more non-classical variant(s). In some embodiments, the agent that inhibits the activity of APP is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. In some embodiments, the antisense oligonucleotide targets RNA or DNA of APP. In some embodiments, methods further comprise administering a cholinesterase inhibitor, N-methyl-D-aspartate (NMDA) receptor antagonist, or an anti-amyloid beta antibody. In some embodiments, the cholinesterase inhibitor is selected from the group consisting of Donepezil, Galantamine, and Rivastigmine. In some embodiments, the NMDA receptor antagonist is memantine. In some embodiments, the anti-amyloid beta antibody is selected from the group consisting of Bapineuzumab, Solanezumab, Gantenerumab, Crenezumab, BAN2401, Ponezumab, and Aducanumab.

Provided herein, in some embodiments, are methods of treating a disease or disorder characterized by unwanted accumulation of amyloid beta protein in an individual in need thereof, comprising:

(a) performing (i) long-read sequencing of RNA or DNA encoding one or more non-classical variant(s) of an APP gene in a biological sample or (ii) a binding assay using one or more probe(s) to the one or more non-classical variant(s);

(b) selecting the individual as having the disease or disorder characterized by unwanted accumulation of amyloid beta protein who has an elevated expression profile or an elevated activity profile of the one or more non-classical variant(s) of an APP gene compared to a reference expression profile or reference activity profile of the one or more non-classical variant(s) derived from a cohort of control individuals; and (c) administering to the individual having the elevated expression profile or the elevated activity profile of the one or more non-classical variant(s) an agent that inhibits activity of the one or more non-classical variant (s).

Provided herein, in some embodiments, are methods of treating Alzheimer's disease in an individual, comprising:

(a) obtaining an expression profile or an activity profile of the one or more non-classical variant(s) of an APP gene from a biological sample from the individual, wherein the expression profile or the activity profile is determined by (i) long-read sequencing of RNA or DNA encoding for the one or more non-classical variant(s), or (ii) binding of one or more probe(s) to the one or more non-classical variant(s);
- (b) determining the individual has or is predisposed to Alzheimer's disease based on the expression profile or the activity profile from (a), wherein a likelihood of having or being predisposed to Alzheimer's disease is increased when the expression profile or the activity profile is elevated compared to a reference expression profile or reference activity profile of the one or more non-classical variant(s) derived from a cohort of control individuals; and
- (c) treating the individual for Alzheimer's disease following (b).

Provided herein, in some embodiments, are methods for identifying a presence of one or more non-classical variant(s) of an amyloid beta precursor protein (APP) gene from a biological sample from an individual, comprising:
- (a) detecting an expression profile or an activity profile of the one or more non-classical variant(s) of the APP gene in the biological sample from the individual by (i) long-read sequencing of RNA or DNA encoding for the one or more non-classical variant(s), or (ii) binding of one or more probe(s) to the one or more non-classical variant(s); and
- (b) identifying the presence of the one or more non-classical variant(s) when an elevated expression profile or elevated activity profile of the one or more non-classical variant(s) of an APP gene compared to a reference expression profile or reference activity profile of the one or more non-classical variant(s) derived from a cohort of control individuals is detected from step (a).

Provided herein, in some embodiments, are methods of notifying an individual of a presence of one or more non-classical variant(s) of an APP gene, comprising:
- (a) obtaining an expression profile or an activity profile of the one or more non-classical variant(s) of the APP gene, wherein the expression profile or the activity profile is determined by (i) long-read sequencing of RNA or DNA encoding for the one or more non-classical variant(s), or (ii) binding of one or more probe(s) to the one or more non-classical variant(s); and
- (b) notifying an individual of the expression profile or the activity profile.

In some embodiments, the expression profile is expression level of the one or more non-classical variant(s), and wherein the activity profile is activity level of the one or more non-classical variant(s). In some embodiments, the expression profile is expression of a set of different non-classical variants, and wherein the activity profile is activity of a set of different non-classical variants. In some embodiments, the methods further comprise quantifying the expression level of the one or more non-classical variant(s) by a method comprising quantitative polymerase chain reaction (qPCR). In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, Alzheimer's disease is familial Alzheimer's disease (FAD) or sporadic Alzheimer's disease. In some embodiments, the biological sample is blood or cerebrospinal fluid. In some embodiments, the biological sample comprises RNA, DNA, or protein encoding for the one or more non-classical variant(s). In some embodiments, the DNA is genomic DNA, extrachromosomal DNA, or circular DNA. In some embodiments, the one or more probe(s) are selected from polynucleotides or polypeptides. In some embodiments, the one or more probe(s) hybridize to RNA or DNA encoding for the one or more non-classical variant(s) within the biological sample. In some embodiments, the one or more probe(s) hybridize to a range of about 35 to about 50 nucleotides of the RNA or DNA. In some embodiments, the one or more probe(s) hybridize to an intraexonic junction between exon 1 and exon 11, exon 1 and exon 14, exon 2 and exon 17, exon 2 and exon 14, exon 2 and exon 18, exon 2 and exon 16, exon 3 and exon 16, exon 3 and exon 14, exon 3 and exon 17, exon 6 and exon 17, exon 6 and exon 18, exon 3 and exon 9, exon 2 and exon 9, exon 16 and exon 18, exon 6 and exon 12, exon 5 and exon 16, or exon 16 and exon 17. In some embodiments, methods further comprise capturing the one or more non-classical variant(s) from the biological sample prior to contacting the one or more non-classical variant(s) with the one or more probe(s). In some embodiments, the one or more non-classical variant(s) is detected by in situ hybridization or immunological hybridization. In some embodiments, the in situ hybridization is chromogenic in situ hybridization or fluorescence in situ hybridization. In some embodiments, binding of the one or more probe(s) to the one or more non-classical variant(s) further comprises a pull-down assay. In some embodiments, the one or more probe(s) for the pull-down assay are designed to hybridize to a portion or all of exon 1, 2, 3, 4, 5, 6, 7, 8, 9, 10, 11, 12, 13, 14, 15, 16, 17, 18, or combinations thereof. In some embodiments, a probe in the one or more probe(s) is labeled using an affinity tag. In some embodiments, the one or more probe(s) bind to one or more protein(s) encoded by the one or more non-classical variant(s). In some embodiments, the one or more probe(s) comprise an antibody or fragment thereof. In some embodiments, a probe of the one or more probe(s) is labeled using a fluorochrome or a radioactive isotope. In some embodiments, methods further comprise isolating and purifying RNA or DNA from the biological sample prior to the long-read sequencing. In some embodiments, methods further comprise reverse transcribing RNA to cDNA prior to the long-read sequencing. In some embodiments, an average read length for the long-read sequencing is at least 5000 bases. In some embodiments, measuring the expression profile by the long-read sequencing comprises quantifying the expression level of the one or more non-classical variant(s) by a method comprising counting a number of reads that map to a sequence of the one or more non-classical variant(s). In some embodiments, the agent that inhibits the activity of APP is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. In some embodiments, the antisense oligonucleotide targets RNA or DNA of APP. In some embodiments, methods further comprise presenting the expression profile or activity profile as a report with graphical elements representing the expression profile or activity profile as detected in (a). In some embodiments, the report further comprises the reference expression profile or reference activity profile. In some embodiments, methods further comprise notifying the individual if the individual is suspected of having or being predisposed to Alzheimer's disease based on the expression profile or the activity profile. In some embodiments, the likelihood of having or being predisposed to Alzheimer's disease is increased by at least 50% based on the expression profile or the activity profile of the one or more non-classical variant(s) of the APP gene. In some embodiments, methods further comprise administering an agent that inhibits activity of the one or more non-classical variant(s). In some embodiments, the agent that inhibits the activity of APP is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. In some embodiments, the antisense oligonucleotide targets RNA or DNA of APP. In some embodiments, methods further comprise administering a cholinesterase inhibitor, N-methyl-D-aspartate (NMDA) receptor antagonist, or an anti-amyloid beta antibody. In some embodiments, the cholinesterase inhibitor is selected from the group consisting of Donepezil, Galantamine, and Rivastigmine. In some embodiments, the NMDA receptor antagonist is memantine. In some embodiments, the anti-amyloid beta antibody is selected from the group consisting of Bapineuzumab, Solanezumab, Gantenerumab, Crenezumab, BAN2401, Ponezumab, and Aducanumab.

Provided herein, in some embodiments, are kits for detecting one or more non-classical variant(s) of an APP gene in a biological sample of an individual, the kit comprising:
 (a) one or more probe(s) that hybridize to the one or more non-classical variant(s) of the APP gene or protein thereof; and
 (b) a detecting reagent for examining binding of the one or more probe(s) with the one or more non-classical variant(s) of the APP gene or protein thereof.

In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, one or more exon(s) in the one or more non-classical variant(s) is rearranged as compared to a control. In some embodiments, the one or more non-classical variant(s) comprises a single nucleotide variation (SNV) in APP. In some embodiments, the SNV in APP translates to amino acid positions in APP selected from a group consisting of A673V, A713T, T714I, V715M, V715A, I716M, V717I, V717F, T719P, and L723P. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. In some embodiments, the one or more probe(s) are selected from polynucleotides or polypeptides. In some embodiments, the one or more probe(s) hybridize to an intraexonic junction between exon 1 and exon 11, exon 1 and exon 14, exon 2 and exon 17, exon 2 and exon 14, exon 2 and exon 18, exon 2 and exon 16, exon 3 and exon 16, exon 3 and exon 14, exon 3 and exon 17, exon 6 and exon 17, exon 6 and exon 18, exon 3 and exon 9, exon 2 and exon 9, exon 16 and exon 18, exon 6 and exon 12, exon 5 and exon 16, or exon 16 and exon 17. In some embodiments, the one or more probe(s) bind to one or more protein(s) encoded by the one or more non-classical variant(s). In some embodiments, the one or more probe(s) comprise an antibody or fragment thereof. In some embodiments, a probe in the one or more probe(s) is labeled using a fluorochrome or a radioactive isotope. In some embodiments, a probe in the one or more probe(s) is labeled using an affinity tag. In some embodiments, the affinity tag is biotin, desthiobiotin, histidine, polyhistidine, myc, hemagglutinin (HA), FLAG, glutathione S transferase (GST), or derivatives thereof. In some embodiments, the detecting reagent binds to the one or more probe(s). In some embodiments, the detecting reagent comprises a fluorescent or a radioactive label. In some embodiments, the individual is suspected of having or being predisposed to Alzheimer's disease.

BRIEF DESCRIPTION OF THE DRAWINGS

FIG. 19C shows Ex 16/17 sense and anti-sense probes for RNA-in situ hybridization on human prefrontal cortex tissue sections. FIG. 19D shows IEJ 3/16 sense and anti-sense probes for RNA-in situ hybridization on human prefrontal cortex tissue sections. Scale bars are 10 μm.

FIG. 19E and FIG. 19H illustrate jgISH nuclei. FIG. 19F and FIG. 19I illustrate graphs of quantification of average foci per nucleus; statistical significance was determined using the unpaired, two-tailed Mann-Whitney test. FIG. 19G and FIG. 19J illustrate cumulative frequency distributions represented as the number of foci per nucleus compared using the unpaired, two-tailed nonparametric Kolmogorov-Smirnov test. ****$p<0.0001$. n.s., not-significant. Error bars are ±SEM. Scale bars are 10 μm.

FIG. 20B illustrates intraexonic junctions (IEJs).

FIG. 22B illustrates a cumulative frequency distribution illustrating the foci per nucleus. FIG. 22C illustrates a graph of an average number of foci per nucleus. ****p<0.0001. n.s., not-significant.

FIG. 22D illustrates a graph of foci per nucleus (x-axis) as relative percent of nuclei (y-axis) from J20+, WT+, J20−, and WT− from a first mouse experiment. FIG. 22E illustrates a graph of average foci per nucleus (y-axis) from J20+, WT+, J20−, and WT− mice from a first mouse experiment. FIG. 22F illustrates a graph of foci per nucleus (x-axis) as relative percent of nuclei (y-axis) from J20+, WT+, J20−, and WT− from a second mouse experiment. FIG. 22G illustrates a graph of average foci per nucleus (y-axis) from J20+, WT+, J20−, and WT− mice from a second mouse experiment.

FIG. 23E illustrates a graph of cumulative percentage of foci (y-axis) as compared to relative foci area (x-axis). FIG. 23F illustrates average foci area (x-axis) from x0, x1, x2 of FIG. 23D. ****p<0.0001. n.s., not-significant. Error bars are ±SEM.

DETAILED DESCRIPTION

Definitions

Figure 1:
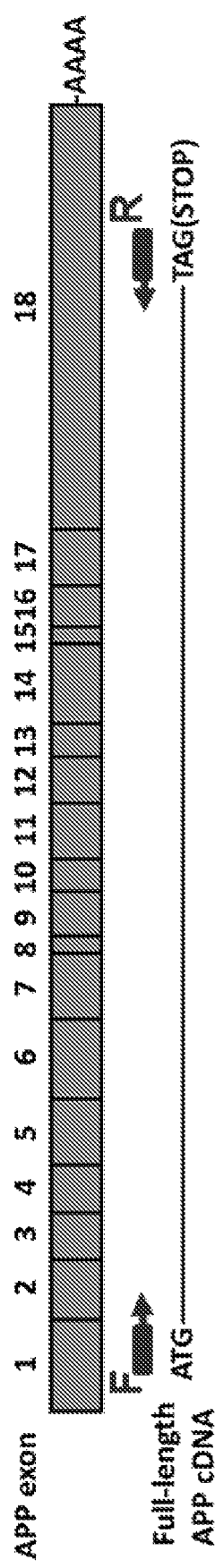
FIG. 1 illustrates a schema of amyloid precursor protein (APP) mRNA and cDNA.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

The term "non-classical variant" as used herein refers to RNA or DNA molecules comprising intraexonic junctions between exons and/or conventional spliced exon-exon junctions, and RNA or DNA molecules lacking introns between exons.

The term "genomic cDNA" or "gencDNA" as used herein refers to a genomic variant lacking introns. In some embodiments, the gencDNA comprises intraexonic junctions between exons. In some embodiments, the gencDNA comprises inverted exons. In some embodiments, the gencDNA is generated by reverse transcription of a non-classical RNA variant. In some embodiments, the gencDNA is incorporated into genomic DNA.

The term "expression" as used herein refers to a transcriptional or translational product of a gene.

The term "activity" as used herein refers to protein biological or chemical function.

The term "RNA" as used herein refers to a molecule comprising at least one ribonucleotide residue. By "ribonucleotide" is meant a nucleotide with a hydroxyl group at the 2' position of a beta-D-ribo-furanose moiety. The term RNA includes, but not limited to, mRNA, ribosomal RNA, tRNA, non-protein-coding RNA (npcRNA), non-messenger RNA, functional RNA (fRNA), long non-coding RNA (lncRNA), pre-mRNAs, and primary miRNAs (pri-miRNAs). The term RNA includes, for example, double-stranded (ds) RNAs; single-stranded RNAs; and isolated RNAs such as partially purified RNA, essentially pure RNA, synthetic RNA, recombinantly produced RNA, as well as altered RNA that differ from naturally-occurring RNA by the addition, deletion, substitution and/or alteration of one or more nucleotides. Such alterations can include addition of non-nucleotide material, such as to the end(s) of the siRNA or internally, for example at one or more nucleotides of the RNA. Nucleotides in the RNA molecules described herein can also comprise non-standard nucleotides, such as non-naturally occurring nucleotides or chemically synthesized nucleotides or deoxynucleotides. These altered RNAs can be referred to as analogs or analogs of naturally-occurring RNA.

The term "RNAi" as used herein refers to an RNA molecule that induces RNA interference (RNAi). In some embodiments, the RNAi molecule is a dsRNA molecule that will generate a siRNA molecule or miRNA molecule following contact with Dicer (i.e., an RNAi molecule precursor). In some embodiments, the RNAi molecule is a siRNA duplex, a siRNA sense molecule, a siRNA anti-sense molecule, a miRNA duplex, a miRNA sense molecule, a miRNA anti-sense molecule, and analogues thereof.

The terms "binding fragment," "antibody fragment," or "antigen binding fragment" are used herein, for purposes of the specification and claims, to mean a portion or fragment of an intact antibody molecule, preferably wherein the fragment retains antigen-binding function. Examples of antibody fragments include Fab, Fab', F(ab')$_2$, Fd, Fd' and Fv fragments, diabodies, linear antibodies, single-chain antibody molecules, single-chain binding polypeptides, scFv, bivalent scFv, tetravalent scFv, and bispecific or multispecific antibodies formed from antibody fragments.

"Fab" fragments are typically produced by papain digestion of antibodies resulting in the production of two identical antigen-binding fragments, each with a single antigen-binding site and a residual "Fc" fragment. Pepsin treatment yields a F(ab')2 fragment that has two antigen-combining sites capable of cross-linking antigen. An "Fv" is the minimum antibody fragment that contains a complete antigen recognition and binding site. In a two-chain Fv species, this region consists of a dimer of one heavy- and one light-chain variable domain in tight, non-covalent association. In a single-chain Fv (scFv) species, one heavy- and one light-chain variable domain are covalently linked by a flexible peptide linker such that the light and heavy chains associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although usually at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also suitable.

The term "monoclonal antibody" refers to an antibody obtained from a population of substantially homogeneous antibodies, i.e., the individual antibodies comprising the population are identical except for possible naturally occurring mutations that are present in minor amounts. In some embodiments, monoclonal antibodies are made, for example, by the hybridoma method. In some embodiments, monoclonal antibodies are isolated from phage antibody libraries.

The antibodies herein include monoclonal, polyclonal, recombinant, chimeric, humanized, bi-specific, grafted, human, and fragments thereof including antibodies altered by any means to be less immunogenic in humans. Thus, for example, the monoclonal antibodies and fragments herein include "chimeric" antibodies and "humanized" antibodies. In general, chimeric antibodies include a portion of the heavy and/or light chain that is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, so long as they exhibit the desired biological activity. For example in some embodiments, a chimeric antibody contains variable regions derived from a mouse and constant regions derived from human in which the constant region contains sequences homologous to both human IgG2 and human IgG4. Numerous methods for preparing "chimeric" antibodies are known in the art. "Humanized" forms of non-human (e.g., murine) antibodies or fragments are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include, grafted antibodies or CDR grafted antibodies wherein part or all of the amino acid sequence of one or more complementarity determining regions (CDRs) derived from a non-human animal antibody is grafted to an appropriate position of a human antibody while maintaining the desired binding specificity and/or affinity of the original non-human antibody. In some embodiments, corresponding non-human residues replace Fv framework residues of the human immunoglobulin. In some embodiments, humanized antibodies comprise residues that are found neither in the recipient antibody nor in the imported CDR or framework sequences. These modifications are made to further refine and optimize antibody performance. In some embodiments, the humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. Numerous methods for "humanizing" antibodies are known in the art.

Alzheimer's Disease

Alzheimer's disease (AD) is a chronic neurodegenerative disease resulting in deterioration of cognitive function. AD is a common form of dementia and estimated to cause 60-70% of the ~48 million people worldwide with dementia. AD can be classified as familial Alzheimer's disease (FAD), which comprises a genetic component, and sporadic AD (SAD) that can arise from several factors including genetic factors.

AD neuropathology is characterized by accumulation of amyloid beta protein and neurofibrillary tangles comprising Tau in the Central Nervous System, synaptic loss, and neuronal death. Specifically, accumulation of amyloid beta as amyloid beta protein plaques or soluble amyloid beta oligomers has been implicated in AD progression.

Amyloid beta protein results from cleavage of amyloid beta precursor protein (APP) by $\alpha$-, $\gamma$-, and $\beta$-secretases. In some instances, cleavage of APP is amyloidogenic and results in unwanted accumulation of amyloid beta protein.

Antibody therapies for treating Alzheimer's disease are primarily aimed at targeting unwanted accumulation of amyloid beta protein. As a result, unwanted amyloid beta protein is cleared from the brain. These treatments, however, result in only partial success. Thus, successful treatments for Alzheimer's disease need to account for the genetic complexity of the disease.

Amyloid precursor protein (APP) gene copy number has been implicated in AD pathogenesis. For example, Down Syndrome (DS) where there are three copies of APP results in neuropathology similar to AD. In addition, increased APP gene copy number has been observed in AD brains. In some instances, the increased gene copy number is a result of genomic rearrangements such as intraexonic rearrangements that generate non-classical variants of APP.

Described herein are non-classical variants of APP gene. Non-classical variants as described herein comprise, in some embodiments, intraexonic rearrangements. In some embodiments, the non-classical variants lack introns. In some embodiments, the non-classical variants comprise a portion of a first exon of APP and a portion of a second exon of APP. In some embodiments, the non-classical variants comprise intraexonic junctions and lack introns. In some embodiments, the non-classical variants comprise inverted exons. In some embodiments, the non-classical variants are genomic cDNAs (gencDNAs). In some embodiments, the non-classical variants comprise a single nucleotide variant (SNV). In some embodiments, non-classical variants comprise deletion of exons. In some embodiments, non-classical variants comprise insertions. In some embodiments, non-classical variants comprise copy number variation (CNV), L1 repeat elements, SNVs, deletions, insertions, intraexonic junctions, or combinations thereof. In some embodiments, the SNVs are somatic SNVs. In some embodiments, the SNVs are germline SNVs.

Various mechanisms for generation of non-classical variants of APP are contemplated herein. In some embodiments, the non-classical variants of APP are generated by DNA damages induced DNA repair. In some embodiments, the non-classical variants of APP are generated by a homologous recombination event. In some embodiments, the non-classical variants of APP are generated by a non-homologous recombination event. In some embodiments, a reverse transcriptase is involved in generating the non-classical variants of APP. In some embodiments, a non-classical variant of APP is generated by activity of a DNA polymerase. In some embodiments, generation of the non-classical variants of APP comprises a RNA splicing event. Generation of a non-classical variant of APP, in certain embodiments, involves transcription. In some embodiments, generation of the one or more non-classical variant(s) involves reverse transcription. In some embodiments, the transcription is cell-type specific. For example, the non-classical variants are generated by neuron-specific RNA transcription.

In some embodiments, a non-classical a variant of APP is generated by incorporation of RNA intermediates into genomic DNA. In some embodiments, the RNA intermediates are non-classical RNA variants of APP. In some embodiments, the RNA intermediates are reversed transcribed and introduced into the genomic DNA. In some embodiments, the RNA intermediates that are reversed transcribed are gencDNAs. In some embodiments, incorporation of RNA intermediates into the genomic DNA involves a break in the DNA. In some embodiments, the break is a single-stranded break. In some embodiments, the break is a double-stranded break. In some embodiments, the break is introduced by an enzyme, a chemical, or radiation.

In some embodiments, generation of a non-classical variant of APP involves alteration in a DNA repair pathway. Exemplary DNA repair pathways include, but are not limited to, non-homologous end joining (NHEJ), microhomology-mediated end joining (MMEJ), homologous recombination, mismatch repair, nucleotide excision repair, or DNA strand cross-link repair.

In some embodiments, generation of a non-classical variant of APP involves RNA processing. In some embodiments, generation of the non-classical variants of APP comprises a RNA splicing event. In some embodiments, generation of the non-classical variants of APP comprises a RNA alternative splicing event. Exemplary alternative splicing events include, but are not limited, intron retention, exon skipping, alternative 5' splice site, alternative 3' splice site, and mutually exclusive exons.

In some embodiments, the non-classical variants are coding. In some embodiments, the non-classical variants are non-coding. In some embodiments, the non-classical variants comprise RNA or DNA. In some embodiments, the non-classical variants comprise genomic cDNA (gencDNA).

In some embodiments, the non-classical variants comprise a portion or all of an exon of APP. In some embodiments, the non-classical variants comprise a portion or all of exon 1, 2, 3, 4, 5, 6, 7, 8, 9, 10, 11, 12, 13, 14, 15, 16, 17, 18, or combinations thereof of APP. In some embodiments, the non-classical variants comprise a portion or all of exon 1, 2, 3, 4, 5, 6, 7, 9, 10, 11, 12, 13, 14, 15, 16, 17, 18, or combinations thereof of APP. In some embodiments, the non-classical variants do not comprise exon 8. In some embodiments, the non-classical variants do not comprise exon 7. In some embodiments, the non-classical variants do not comprise exon 8 and exon 7. In some embodiments, the non-classical variants of APP comprise a portion or all of exon 1, 2, 3, 4, 5, 6, 7, 8, 9, 10, 11, 12, 13, 14, 15, 16, 17, or 18 of APP, wherein the portion or all of the exon 1, 2, 3, 4, 5, 6, 7, 8, 9, 10, 11, 12, 13, 14, 15, 16, 17, or 18 of APP is inverted.

For example, the non-classical variants comprise nucleotides 1-24 of exon 3 of APP and nucleotides 45-101 of exon 16 of APP. In some embodiments, the non-classical variants comprise nucleotides from more than one exon of APP. In some embodiments, the non-classical variants comprise nucleotides from at least 2, 3, 4, 5, 6, 7, 8, 9, 10, 11, 12, 13, 14, 15, 16, or 17 exons of APP. In some embodiments, the non-classical variants comprise a portion of at most 2, 3, 4, 5, 6, 7, 8, 9, 10, 11, 12, 13, 14, 15, 16, or 17 of APP.

In some embodiments, non-classical variants of APP comprise a portion of exon 1 and a portion of exon 2, 3, 4, 5, 6, 7, 8, 9, 10, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 1 and at least or about 10 nt, 15 nt, 20 nt, 25 nt, 30 nt, 40 nt, 50 nt, 75 nt, 100 nt, 150 nt, 200 nt, or more than 200 nt of exon 2, 3, 4, 5, 6, 7, 8, 9, 10, 11, 12, 13, 14, 15, 16, 17, 18, or combinations thereof.

In some embodiments, non-classical variants of APP comprise a portion of exon 2 and a portion of exon 1, 3, 4, 5, 6, 7, 8, 9, 10, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 2 and at least or about 10 nt, 15 nt, 20 nt, 25 nt, 30 nt, 40 nt, 50 nt, 75 nt, 100 nt, 150 nt, 200 nt, or more than 200 nt of exon 1, 3, 4, 5, 6, 7, 8, 9, 10, 11, 12, 13, 14, 15, 16, 17, 18, or combinations thereof.

In some embodiments, non-classical variants of APP comprise a portion of exon 3 and a portion of exon 1, 2, 4, 5, 6, 7, 8, 9, 10, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 3 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 4, 5, 6, 7, 8, 9, 10, 11, 12, 13, 14, 15, 16, 17, 18, or combinations thereof.

In some embodiments, non-classical variants of APP comprise a portion of exon 4 and a portion of exon 1, 2, 3, 5, 6, 7, 8, 9, 10, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 4 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 5, 6, 7, 8, 9, 10, 11, 12, 13, 14, 15, 16, 17, 18, or combinations thereof.

In some embodiments, non-classical variants of APP comprise a portion of exon 5 and a portion of exon 1, 2, 3, 4, 6, 7, 8, 9, 10, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 5 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 6, 7, 8, 9, 10, 11, 12, 13, 14, 15, 16, 17, 18, or combinations thereof.

In some embodiments, non-classical variants of APP comprise a portion of exon 6 and a portion of exon 1, 2, 3, 4, 5, 7, 8, 9, 10, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 6 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 7, 8, 9, 10, 11, 12, 13, 14, 15, 16, 17, 18, or combinations thereof.

In some embodiments, non-classical variants of APP comprise a portion of exon 7 and a portion of exon 1, 2, 3, 4, 5, 6, 8, 9, 10, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 7 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 8, 9, 10, 11, 12, 13, 14, 15, 16, 17, 18, or combinations thereof.

In some embodiments, non-classical variants of APP comprise a portion of exon 8 and a portion of exon 1, 2, 3, 4, 5, 6, 7, 9, 10, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 8 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 9, 10, 11, 12, 13, 14, 15, 16, 17, 18, or combinations thereof.

In some embodiments, non-classical variants of APP comprise a portion of exon 9 and a portion of exon 1, 2, 3, 4, 5, 6, 7, 8, 10, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 9 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 10, 11, 12, 13, 14, 15, 16, 17, 18, or combinations thereof.

In some embodiments, non-classical variants of APP comprise a portion of exon 10 and a portion of exon 1, 2, 3, 4, 5, 6, 7, 8, 9, 11, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 10 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 11, 12, 13, 14, 15, 16, 17, 18, or combinations thereof.

In some embodiments, non-classical variants of APP comprise a portion of exon 11 and a portion of exon 1, 2, 3, 4, 5, 6, 7, 8, 9, 10, 12, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 11 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 10, 12, 13, 14, 15, 16, 17, 18, or combinations thereof.

In some embodiments, non-classical variants of APP comprise a portion of exon 12 and a portion of exon 1, 2, 3, 4, 5, 6, 7, 8, 9, 10, 11, 13, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 12 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 10, 11, 13, 14, 15, 16, 17, 18, or combinations thereof.

In some embodiments, non-classical variants of APP comprise a portion of exon 13 and a portion of exon 1, 2, 3, 4, 5, 6, 7, 8, 9, 10, 11, 12, 14, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 13 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 10, 11, 12, 14, 15, 16, 17, 18, or combinations thereof.

In some embodiments, non-classical variants of APP comprise a portion of exon 14 and a portion of exon 1, 2, 3, 4, 5, 6, 7, 8, 9, 10, 11, 12, 13, 15, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 14 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 10, 11, 12, 13, 15, 16, 17, 18, or combinations thereof.

In some embodiments, non-classical variants of APP comprise a portion of exon 15 and a portion of exon 1, 2, 3, 4, 5, 6, 7, 8, 9, 10, 11, 12, 13, 14, 16, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 15 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 10, 11, 12, 13, 14, 16, 17, 18, or combinations thereof.

In some embodiments, non-classical variants of APP comprise a portion of exon 16 and a portion of exon 1, 2, 3, 4, 5, 6, 7, 8, 9, 10, 11, 12, 13, 14, 15, 17, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 16 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 10, 11, 12, 13, 14, 15, 17, 18, or combinations thereof.

In some embodiments, non-classical variants of APP comprise a portion of exon 17 and a portion of exon 1, 2, 3, 4, 5, 6, 7, 8, 9, 10, 11, 12, 13, 14, 15, 16, 18, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 17 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 10, 11, 12, 13, 14, 15, 16, or combinations thereof.

In some embodiments, non-classical variants of APP comprise a portion of exon 18 and a portion of exon 1, 2, 3, 4, 5, 6, 7, 8, 9, 10, 11, 12, 13, 14, 15, 16, 17, or combinations thereof. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon18 and at least or about 10 nt, 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 10, 11, 12, 13, 14, 15, 16, 17, or combinations thereof.

Non-classical transcript variants as described herein, in certain embodiments, comprise portions of at least 2 exons. In some embodiments, the non-classical variants comprise a portion of exon 1 and a portion of exon 11. In some embodiments, the non-classical variants comprise a portion of exon 1 and a portion of exon 12. In some embodiments, the non-classical variants comprise a portion of exon 1 and a portion of exon 14. In some embodiments, the non-classical variants comprise a portion of exon 1 and a portion of exon 17. In some embodiments, the non-classical variants comprise a portion of exon 2 and a portion of exon 14. In some embodiments, the non-classical variants comprise a portion of exon 2 and a portion of exon 16. In some embodiments, the non-classical variants comprise a portion of exon 2 and a portion of exon 17. In some embodiments, the non-classical variants comprise a portion of exon 2 and a portion of exon 18. In some embodiments, the non-classical variants comprise a portion of exon 3 and a portion of exon 9. In some embodiments, the non-classical variants comprise a portion of exon 3 and a portion of exon 14. In some embodiments, the non-classical variants comprise a portion of exon 3 and a portion of exon 16. In some embodiments, the non-classical variants comprise a portion of exon 3 and a portion of exon 17. In some embodiments, the non-classical variants comprise a portion of exon 3 and a portion of exon 18. In some embodiments, the non-classical variants comprise a portion of exon 5 and a portion of exon 16. In some embodiments, the non-classical variants comprise a portion of exon comprise exon 6 and a portion of exon 12. In some embodiments, the non-classical variants comprise a portion of exon 6 and a portion of exon 16. In some embodiments, the non-classical variants comprise a portion of exon 6 and a portion of exon 17. In some embodiments, the non-classical variants comprise a portion of exon 6 and a portion of exon 18. In some embodiments, the non-classical variants comprise a portion of exon 16 and a portion exon 18.

Described herein, in certain embodiments, are non-classical variants of APP comprising portions of at least two exons, wherein the at least two exons are linked by intraexonic junctions. In some embodiments, the intraexonic junction is between exon 1 and exon 2, 3, 4, 5, 6, 7, 8, 9, 10, 11, 12, 13, 14, 15, 16, 17, 18, or combinations thereof. In some embodiments, the intraexonic junction is between exon 2 and exon 1, 3, 4, 5, 6, 7, 8, 9, 10, 11, 12, 13, 14, 15, 16, 17, 18, or combinations thereof. In some embodiments, the intraexonic junction is between exon 3 and exon 1, 2, 4, 5, 6, 7, 8, 9, 10, 11, 12, 13, 14, 15, 16, 17, 18, or combinations thereof. In some embodiments, the intraexonic junction is between exon 4 and exon 1, 2, 3, 5, 6, 7, 8, 9, 10, 11, 12, 13, 14, 15, 16, 17, 18, or combinations thereof. In some embodiments, the intraexonic junction is between exon 5 and exon 1, 2, 3, 4, 6, 7, 8, 9, 10, 11, 12, 13, 14, 15, 16, 17, 18, or combinations thereof. In some embodiments, the intraexonic junction is between exon 6 and exon 1, 2, 3, 4, 5, 7, 8, 9, 10, 11, 12, 13, 14, 15, 16, 17, 18, or combinations thereof. In some embodiments, the intraexonic junction is between exon 7 and exon 1, 2, 3, 4, 5, 6, 8, 9, 10, 11, 12, 13, 14, 15, 16, 17, 18, or combinations thereof. In some embodiments, the intraexonic junction is between exon 8 and exon 1, 2, 3, 4, 5, 6, 7, 9, 10, 11, 12, 13, 14, 15, 16, 17, 18, or combinations thereof. In some embodiments, the intraexonic junction is between exon 9 and exon 1, 2, 3, 4, 5, 6, 7, 8, 10, 11, 12, 13, 14, 15, 16, 17, 18, or combinations thereof. In some embodiments, the intraexonic junction is between exon 10 and exon 1, 2, 3, 4, 5, 6, 7, 8, 9, 11, 12, 13, 14, 15, 16, 17, 18, or combinations thereof. In some embodiments, the intraexonic junction is between exon 11 and exon 1, 2, 3, 4, 5, 6, 7, 8, 9, 10, 12, 13, 14, 15, 16, 17, 18, or combinations thereof. In some embodiments, the intraexonic junction is between exon 12 and exon 1, 2, 3, 4, 5, 6, 7, 8, 9, 10, 11, 13, 14, 15, 16, 17, 18, or combinations thereof. In some embodiments, the intraexonic junction is between exon 13 and exon 1, 2, 3, 4, 5, 6, 7, 8, 9, 10, 11, 12, 14, 15, 16, 17, 18, or combinations thereof. In some embodiments, the intraexonic junction is between exon 14 and exon 1, 2, 3, 4, 5, 6, 7, 8, 9, 10, 11, 12, 13, 15, 16, 17, 18, or combinations thereof. In some embodiments, the intraexonic junction is between exon 15 and exon 1, 2, 3, 4, 5, 6, 7, 8, 9, 10, 11, 12, 13, 14, 16, 17, 18, or combinations thereof. In some embodiments, the intraexonic junction is between exon 16 and exon 1, 2, 3, 4, 5, 6, 7, 8, 9, 10, 11, 12, 13, 14, 15, 17, 18, or combinations thereof. In some embodiments, the intraexonic junction is between exon 17 and exon 1, 2, 3, 4, 5, 6, 7, 8, 9, 10, 11, 12, 13, 14, 15, 16, 18, or combinations thereof. In some embodiments, the intraexonic junction is between exon 18 and exon 1, 2, 3, 4, 5, 6, 7, 8, 9, 10, 11, 12, 13, 14, 15, 16, 17, or combinations thereof.

In some embodiments, sequence complementarity exists in non-classical variants of APP in the intraexonic junctions. In some embodiments, the sequence complementarity is at least or about 2, 4, 6, 8, 10, 12, 14, 16, 18, 20, 22, 24, 26, 28, 30, 32, 34, 36, 38, 40, 50, 60, 70, 80, 90, 100, or more than 100 nucleotides. In some embodiments, the sequence complementarity is in a range of about 2 nucleotides to 20 nucleotides. In some embodiments, the sequence complementarity is in a range of about 2 nucleotides to about 200 nucleotides, about 4 nucleotides to about 180 nucleotides, about 6 nucleotides to about 160 nucleotides, about 8 nucleotides to about 140 nucleotides, about 10 nucleotides to about 120 nucleotides, about 12 nucleotides to about 100 nucleotides, about 14 nucleotides to about 80 nucleotides, about 16 nucleotides to about 60 nucleotides, or about 20 nucleotides to about 40 nucleotides.

Non-classical variants of APP as described herein, in certain embodiments, comprise different sequences. In some embodiments, a number of different sequences is at least or about 2, 10, 20, 30, 40, 50, 60, 70, 80, 90, 100, 200, 300, 400, 500, 600, 700, 800, 900, 1000, or more than 1000 sequences. In some embodiments, a number of different sequences in in a range of about 2 sequences to about 1000 sequences, about 4 sequences to about 900 sequences, about 6 sequences to about 800 sequences, about 8 sequences to about 700 sequences, about 10 sequences to about 600 sequences, about 20 sequences to about 500 sequences, about 30 sequences to about 400 sequences, about 40 sequences to about 300 sequences, about 50 sequences to about 200 sequences, and about 60 sequences to about 100 sequences.

In some embodiments, non-classical variants of APP comprising portions of at least 2 exons further comprise a deletion of at least one exon or a portion of at least one exon of APP. For example, the non-classical transcript variants comprise a deletion of exon 8 or a portion of exon 8 of APP. In some embodiments, the non-classical transcript variants comprise a deletion of exon 7 or a portion of exon 7 of APP. In some embodiments, the non-classical transcript variants comprise a deletion of exon or a portion of exon 1, 2, 3, 4, 5, 6, 7, 8, 9, 10, 11, 12, 13, 14, 15, 16, 17, 18, or combinations thereof of APP. In some embodiments, the non-classical transcript variants comprise a deletion of exon or a portion of exon 2, 3, 4, 5, 6, 7, 8, 9, 10, 11, 12, 13, 14, 15, 16, 17, or combinations thereof.

The APP mRNA sequence is set forth at NCBI Reference Sequence: NM_000484.3. Exemplary non-classical variants are illustrated in Table 1.

TABLE 1

| SEQ ID NO | Name* | Sequence** |
|---|---|---|
| 1 | cAPP-R3/16 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAGGAAGGCATCCTGCAGTATTGCCAAGAAG TCTACCCTGAACTGCAGATCACC:AAGATGGATGCAGAATTCCGAC ATGACTCAGGATATGAAGTTCATCATCAAAAATTGGTGTTCTTTGC AGAAGATGTGGGTTCAAACAAAGGTGCAATCATTGGACTCATGGT GGGCGGTGTTGTCATAGCGACAGTGATCGTCATCACCTTGGTGATG CTGAAGAAGAAACAGTACACATCCATTCATCATGGTGTGGTGGAG GTTGACGCCGCTGTCACCCCAGAGGAGCGCCACCTGTCCAAGATG CAGCAGAACGGCTACGAAAATCCAACCTACAAGTTCTTTGAGCAG ATGCAGAACTAG |
| 2 | cAPP-R3/16-2 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAGGAAGGCATCCTGCAGTATTGCCAAGAAG TCTACCCTGAACTGCAGATCACC:AAGATGGATGCAGAATTCCGAC ATGACTCAGGATATGAAGTTCATCATCAAAAATTGGTGTTCTTTGC AGAAGATGTGGGTTCAAACAAAGGTGCAATCATTGGACTCATAGT GGGCGGTGTTGTCATAGCGACAGTGATCGTCATCACCTTGGTGATG CTGAAGAAGAAACAGTACACATCCATTCATCATGGTGTGGTGGAG GTTGACGCCGCTGTCACCCCAGAGGAGCGCCACCTGTCCAAGATG CAGCAGAACGGCTACGAAAATCCAACCTACAAGTTCTTTGAGCAG ATGCAGAACTAG |
| 3 | cAPP-R2/18 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAGGAAGGCATCCTG:CGCTACGAAAATCCAA CCTACAAGTTCTTTGAGCAGATGCAGAACTAG |

TABLE 1-continued

| SEQ ID NO | Name* | Sequence** |
|---|---|---|
| 4 | cAPP-R6/18 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAGGAAGGCATCCTGCAGTATTGCCAAGAAG TCTACCCTGAACTGCAGATCACCAATGTGGTAGAAGCCAACCAAC CAGTGACCATCCAGAACTGGTGCAAGCGGGGCCGCAAGCAGTGCA AGACCCATCCCCACTTTGTGATTCCCTACCGCTGCTTAGTTGGTGA GTTTGTAAGTGATGCCCTTCTCGTTCCTGACAAGTGCAAATTCTTA CACCAGGAGAGGATGGATGTTTGCGAAACTCATCTTCACTGGCAC ACCGTCGCCAAAGAGACATGCAGTGAGAAGAGTACCAACTTGCAT GACTACGGCATGTTGCTGCCCTGCGGAATTGACAAGTTCCGAGGG GTAGAGTTTGTGTGTTGCCCACTGGCTGAAGAAAGTGACAATGTG GATTCTGCTGATGCGGAGGAGGATGACTCGGATGTCTGGTGGGGC GGAGCAGACACAGACTATGCAGATGGGAGTGAAGACAAAGTAGT AGAAGTAGCAGAGGAGGAAGAAGTGGCTGAGGTGGAAGAAGAAG AAGCCGATGATGAC:GAGGAGCGCCACCTGTCCAAGATGCAGCAG AGCGGCTACGAAAATCCAACCTACAAGTTCTTTGAGCAGATGCAG AACTAG |
| 5 | cAPP-R3/14 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAGGAAGGCATCCTGCAGTATTGCCAAGAAG TCTACCCTGAACTGCAGATCACCAATGTGGTAGAAGCCAACC:ACAG AAAACGAAGTTGAGCCTGTTGATGCCCGCCCTGCTGCCGACCGAG GACTGACCACTCGACCAGGTTCTGGGTTGACAAATATCAAGACGG AGGAGATCTCTGAAGTGAAGATGGATGCAGAATTCCGACATGACT CAGGATATGAAGTTCATCATCAAAAATTGGTGTTCTTTACAGAAGA TGTGGGTTCAAACAAAGGTGCAATCATTGGACTCATGGTGGGCGG TGTTGTCATAGCGACAGTGATCGTCATCACCTTGGTGATGCTGAAG AAGAAACAGTACACATCCATTCATCATGGTGTGGTGGAGGTTGAC GCCGCTGTCACCCCAGAGGAGCGCCACCTGTCCAAGATGCAGCAG AACGGCTACGAAAATCCAACCTACAAGTTCTTTGAGCAGATGCAG AACTAG |
| 6 | ncAPP-R3/17 | ATGCTGCCCGGTTTGGCACTGCTCCTGCTGGCCGCCTGGACGGCTC GGGCGCTGGAGATACCCACTGATGGTAATGCTGGCCTGCTGGCTG AACCCCAGATTGCCATGTTCTGTGGCAGACTGAACATGCACATGA ATGTCCAGAATGGGAAGTGGGACTCAGATCCATCAGGGACCAAAA CCTGCATTGATACCAAGGAAGGCATCCTGCAGTATTGCCAAGAAG TCTACCCTGAACTGCAGATCACCAATGTGGTAGAAGCCAACCAAC CAGTGACCATCCAGAACTGGTGCAAGCGGGGCCGCAAGCAG:TGT TGTCATAGCGACAGTGATCGTCATCACCTTGGTGATGCTGAAGAA GAAACAGTACACATCCATTCATCATGGTGTGGTGGAGGTTGACGC CGCTGTCACCCCAGAGGAGCGCCACCTGTCCAAGATGCAGCAGAA CGGCTACGAAAATCCAACCTACAAGTTCTTTGAGCAGATGCAGAA CTAG |
| 7 | cAPP-R1/11 | ATGCTGCCCGGTTTGGCACTGCTCCTGCTGGCCGCCTGGACG:GCC TCGTCACGTGTTCAATATGCTAAAGAAGTATGTCCGCGCAACA GAAGGACAGACAGCACACCCTAAAGCATTTCGAGCATGTGCGCAT GGTGGATCCCAAGAAAGCCGCTCAGATCCGGTCCCAGGTTATGAC ACACCTCCGTGTGATTTATGAGCGCATGAATCAGTCTCTCTCCCTG CTCTACAACGTGCCTGCAGTGCCGAGGAGATTCAGGATGAAGTT GATGAGCTGCTTCAGAAAGAGCAAAACTATTCAGATGACGTCTTG GCCAACATGATTAGTGAACCAAGGATCAGTTACGGAAACGATGCT CTCATGCCATCTTTGACCGAAACGAAAACCACCGTGGAGCTCCTTC CCGTGAATGGAGAGTTCAGCCTGGACGATCTCCAGCCGTGGCATT CTTTTGGGGCTGACTCTGTGCCAGCCAACACAGAAAACGAAGTTG AGCCTGTTGATGCCCGCCCTGCTGCCGACCGAGGACTGACCACTCG ACCAGGTTCTGGGTTGACAAATATCAAGACGGAGGAGATCTCTGA AGTGAAGATGGATGCAGAATTCCGACATGACTCAGGATATGAAGT TCATCATCAAAAATTGGTGTTCTTTGCAGAAGATGTGGGTTCAAAC AAAGGTGCAATCATTGGACTCATGGTGGGTGGTGTTGTCATAGCG ACAGTGATCGTCATCACCTTGGTGATGCTGAAGAAGAAACAGTAC ACATCCATTCATCATGGTGTGGTGGAGGTTGACGCCGCTGTCACCC CAGAGGAGCGCCACCTGTCCAAGATGCAGCAGAACGGCTACGAAA ATCCAACCTACAAGTTCTTTGAGCAGATGCAGAACTAG |
| 8 | ncAPP-R1/13 | ATGCTGCCCGGTTTGGCACTGCTCCTGCAGTGG:GAGGAGATTCAG GATGAAGTTGATGAACTGCTTCAGAAAGAGCAAAACTATTCAGAT GACGTCTTGGCCAACATGATTAGTGAACCAAGGATCAGTTACGGA AACGATGCTCTCATGCCATCTTTGACCGAAACGAAAACCACCGTG GAGCTCCTTCCCGTGAATGGAGAGTTCAGCCTGGACGATCTCCAGC |

TABLE 1-continued

| SEQ ID NO | Name* | Sequence** |
|---|---|---|
| | | CGTGGCATTCTTTTGGGGCTGACTCTGTGCCAGCCAACACAGAAAA<br>CGAAGTTGAGCCTGTTGATGCCCGCCCTGCTGCCGACCGAGGACT<br>GACCACTCGACCAGGTTCTGGGTTGACAAATATCAAGACGGAGGA<br>GATCTCTGAAGTGAAGATGGATGCAGAATTCCGACATGACTCAGG<br>ATATGAAGTTCATCATCAAAAATTGGTGTTCTTTGCAGAAGATGTG<br>GGTTCAAACAAAGGTGCAATCATTGGACTCATGGTGGCGGTGTTG<br>TCATAGCGACAGTGATCGTCATCACCTTGGTGATGCTGAAGAAGA<br>AACAGTACACATCCATTCATCATGGTGTGGTGGAGGTTGACGCCG<br>CTGTCACCCCAGAGGAGCGCCACCTGTCCAAGATGTGGCAGAACG<br>GCTACGAAAATCCAACCTACAAGTTCTTTGAGCAGATGCAGAACT<br>AG |
| 9 | ncAPP-R1/11-2 | ATGCTGCCCGGTTTGGCACTGCTC:TGCAGGCTGTTCCTCCTCGGCC<br>TCGTCACGTGTTCAATATGCTAAAGAAGTATGTCCGCGCAGAACA<br>GAAGGACAGACAGCACACCCTAAAGCATTTCGAGCATGTGCGCAT<br>GGTGGATCCCAAGAAAGCCGCTCAGATCCGGTCCCAGGTTATGAC<br>ACACCTCCGTGTGATTTATGAGCGCATGAATCAGTCTCTCTCCCTG<br>CTCTACAACGTGCCTGCAGTGGCCGAGGAGATTCAGGATGAAGTT<br>GATGAGCTGCTTCAGAAAGAGCAAAACTATTCAGATGACGTCTTG<br>GCCAACATGATTAGTGAACCAAGGATCAGTTACGGAAACGATGCT<br>CTCATGCCATCTTTGACCGAAACGAAAACCACCGTGGAGCTCCTTC<br>CCGTGAATGGAGAGTTCAGCCTGGACGATCTCCAGCCGTGGCATT<br>CTTTTGGGGCTGACTCTGTGCCAGCCAACACAGAAAACGAAGTTG<br>AGCCTGTTGATGCCCGCCCTGCTGCCGACCGAGGACTGACCACTCG<br>ACCAGGTTCTGGGTTGACAAATATCAAGACGGAGGAGATCTCTGA<br>AGTGAAGATGGATGCAGAATTCCGACATGACTCAGGATATGAAGT<br>TCATCATCAAAAATTGGTGTTCTTTGCAGAAGATGTGGGTTCAAAC<br>AAAGGTGCAATCATTGGACTCATGGTGGGCGGTGTTGTCATAGCG<br>ACAGTGATCGTCATCACCTTGGTGATGCTGAAGAAGAAACAGTAC<br>ACATCCATTCATCATGGTGTGGTGGAGGTTGACGCCGCTGTCACCC<br>CAGAGGAGCGCCACCTGTCCAAGATGCAGCAGAACGGCTACGAAA<br>ATCCAACCTACAAGTTCTTTGAGCAGATGCAGAACTAG |
| 10 | ncAPP-R1/14 | ATGCTGCCCGGTTTGGCACTGCTCCTGCTGGCCGCCTGGACAGCT:<br>CCTTCCCGTGAATGGAGAGTTCAGCCTGGACGATCTCCAGCCGTG<br>GCATTCTTTTGGGGCTGACTCTGTGCCAGCCAACACAGAAAACGA<br>AGTTGAGCCTGTTGATGCCCGCCCTGCTGCCGACCGAGGACTGACC<br>ACTCGACCAGGTTCTGGGTTGACAAATATCAAGACGGAGGAGATC<br>TCTGAAGTGAAGATGGATGCAGAATTCCGACATGACTCAGGATAT<br>GAAGTTCATCATCAAAAATTGGTGTTCTTTGCAGAAGATGTGGGTT<br>CAAACAAAGGTGCAATCATTGGACTCATGGTGGGCGGTGTTGTCA<br>TAGCGACAGTGATCGTCATCACCTTGGTGATGCTGAAGAAGAAAC<br>AGTACACATCCATTCATCATGGTGTGGTGGAGGTTGACGCCGCTGT<br>CACCCCAGAGGAGCGCCACCTGTCCAAGATGCAGCAGAACGGCTA<br>CGAAAATCCAACCTACAAGTTCTTTGAGCAGATGCAGAACTAG |
| 11 | ncAPP-R2/17 | ATGCTGCCCGGTTTGGCACTGCTCCTGCTGGCCGCCTGGACGGCTC<br>GGGCGCTGGAGGTACCC:AATCATTGGACTCATGGTGGGCGGTGTT<br>GTCATAGCGACAGTGATCGTCATCACCTTGGTGATGCTGAAGAAG<br>AAACAGTACACATCCATTCATCATGGTGTGGTGGAGGTTGACGCC<br>GCTGTCACCCCAGAGGAGCGCCACCTGTCCAAGATGCAGCAGAAC<br>GGCTACGAAAATCCAACCTACAAGTTCTTTGAGCAGATGCAGAAC<br>TAG |
| 12 | cAPP-R2/16 | ATGCTGCCCGGTTTGGCACTGCTCCTGCTGGCCGCCTGGACGGCTC<br>GGGCGCTGGAGGTACCCACTGATGGTAATGCTGGCCTGCTGGCTG<br>AACCCCAGATTGCCATGTTCTGTGGCAGACTGAACATGCACATGA<br>ATGTCCAGAATGGGAAGTGGGATTCAGATCCATCAGGGACCAAAA<br>CCTGCATTGATACCAAGGAAGGCATCCTGCAGTAT:ATGCAGAATT<br>CCGACATGACTCAGGATATGAAGTTCATCATCAAAAATTGGTGTTC<br>TTTGCAGAAGATGTGGGTTCAAACAAAGGTGCAATCATTGGACTC<br>ATGGTGGGCGGTGTTGTCATAGCGACAGTGATCGTCATCACCTTGG<br>TGATGCTGAAGAAGAAACAGTACACATCCATTCATCATGGTGTGG<br>TGGAGGTTGACGCCGCTGTCACCCCAGAGGAGCGCCACCTGTCCA<br>AGATGCAGCAGAACGGCTACGAAAATCCAACCTACAAGTTCTTTG<br>AGCAGATGCAGAACTAG |
| 13 | cAPP-R6/17 | ATGCTGCCCGGTTTGGCACTGCTCCTGCTGGCCGCCTGGACGGCTC<br>GGGCGCTGGAGGTACCCACTGATGGTAATGCTGGCCTGCTGGCTG<br>AACCCCAGATTGCCATGTTCTGTGGCAGACTGAACATGCACATGA<br>ATGTCCAGAATGGGAAGTGGGATTCAGATCCATCAGGGACCAAAA<br>CCTGCATTGATACCAAGGAAGGCATCCTGCAGTATTGCCAAGAAG<br>TCTACCCTGAACTGCAGATCACCAATGTGGTAGAAGCCAACCAAC<br>CAGTGACCATCCAGAACTGGTGCAAGCGGGGCCGCAAGCAGTGCA<br>AGACCCATCCCCACTTTGTGATTCCCTACCGCTGCTTAGTTGGTGA<br>GTTTGTAAGTGATGCCCTTCTCGTTCCTGACAAGTGCAAATTCTTA<br>CACCAGGAGAGGATGGATGTTTGCGAAACTCATCTTCACTGGCAC |

TABLE 1-continued

| SEQ ID NO | Name* | Sequence** |
|---|---|---|
| | | ACCGTCGCCAAAGAGACATGCAGTGAGAAGAGTACCAACTTGCAT
GACTACGGCATGTTGCTGCCCTGCGGAATTGACAAGTTCCGAGGG
GTAGAGTTTGTGTGTTGCCCACTGGCTGAAGAAAGTGACAATGTG
GATTCTGCTGATGCGGAGGAGGATGACTCGGATGTCTGGTGGGGC
GGAGCAGACACAGACTATGCAGATGGGAGTGAAGACAAA:GGTGC
AATCATTGGACTCATGGTGGGCGGTGTTGTCATAGCGACAGTGATC
GTCATCACCTTGGTGATGCTGAAGAAGAAACAGTACACATCCATT
CATCATGGTGTGGTGGAGGTTGACGCCGCTGTCACCCCAGAGGAG
CGCCACCTGTCCAAGATGCAGCAGAACGGCTACGAAAATCCAACC
TACAAGTTCTTTGAGCAGATGCAGAACTAG |
| 14 | ncAPP-R2/14 | ATGCTGCCCGGTTTGGCACTGCTCCTGCTGGCCGCCTGGACGGCTC
GGGCGCTGGAGGTACCCACTGATGGTAATGCTGGCCTGCTGGCTG
AACCCCAGATTGCCATGTTCTGTGGCAGACTGAACATGCACATGA
ATGTCCAGAATGGGAAGTGGGATTCAGATCCATCAGGGACCAAAA
CCTGCATTGATACCAAG:GATCAGTTACGGAAACGATGCTCTCATG
CCATCTTTGACCGAAACGAAAACCACCGTGGAGCTCCTTCCCGTGA
ATGGAGAGTTCAGCCTGGACGATCTCCAGCCGTGGCATTCTTTTGG
GGCTGACTCTGTGCCAGCCAACACAGAAAACGAAGTTGAGCCTGT
TGATGCCCGCCCTGCTGCCGACCGAGGACTGACCACTCGACCAGG
TTCTGGGTTGACAAATATCAAGACGGAGGAGATCTCTGAAGTGAA
GATGGATGCAGAATTCCGACATGACTCAGGATATGAAGTTCATCA
TCAAAAATTGGTGTTCTTTGCAGAAGATGTGGGTTCAAACAAAGG
TGCAATCATTGGACTCATGGTGGGCGGTGTTGTCATAGCGACAGTG
ATCGTCATCACCTTGGTGATGCTGAAGAAGAAACAGTACACATCC
ATTCATCATGGTGTGGTGGAGGTTGACGCCGCTGTCACCCCAGAG
GAGCGCCACCTGTCCAAGATGCAGCAGAACGGCTACGAAAATCCA
ACCTACAAGTTCTTTGAGCAGATGCAGAACTAG |
| 15 | ncAPP-R14/17-d8 | ATGCTGCCCGGTTTGGCACTGCTCCTGCTGGCCGCCTGGACGGCTC
GGGCGCTGGAGGTACCCACTGATGGTAATGCTGGCCTGCTGGCTG
AACCCCAGATTGCCATGTTCTGTGGCAGACTGAACATGCACATGA
ATGTCCAGAATGGGAAGTGGGATTCAGATCCATCAGGGACCAAAA
CCTGCATTGATACCAAGGAAGGCATCCTGCAGTATTGCCAAGAAG
TCTACCCTGAACTGCAGATCACCAATGTGGTAGAAGCCAACCAAC
CAGTGACCATCCAGAACTGGTGCAAGCGGGCCGCAAGCAGTGCA
AGACCCATCCCCACTTTGTGATTCCCTACCGCTGCTTAGTTGGTGA
GTTTGTAAGTGATGCCCTTCTCGTTCCTGACAAGTGCAAATTCTTA
CACCAGGAGAGGATGGATGTTTGCGAAACTCATCTTCACTGGCAC
ACCGTCGCCAAAGAGACATGCAGTGAGAAGAGTACCAACTTGCAT
GACTACGGCATGTTGCTGCCCTGCGGAATTGACAAGTTCCGAGGG
GTAGAGTTTGTGTGTTGCCCACTGGCTGAAGAAAGTGACAATGTG
GATTCTGCTGATGCGGAGGAGGATGACTCGGATGTCTGGTGGGGC
GGAGCAGACACAGACTATGCAGATGGGAGTGAAGACAAAGTAGT
AGAAGTAGCAGAGGAGGAAGAAGTGGCTGAGGTGGAAGAAGAAG
AAGCCGATGATGACGAGGACGATGAGGATGGTGATGAGGTAGAG
GAAGAGGCTGAGGAACCCTACGAAGAAGCCACAGAGAGAACCAC
CAGCATTGCCACCACCACCACCACCACAGAGTCTGTGGAAGA
GGTGGTTCGAGAGGTGTGCTCTGAACAAGCCGAGACGGGGCCGTG
CCGAGCAATGATCTCCCGCTGGTACTTTGATGTGACTGAAGGGAA
GTGTGCCCCATTCTTTTACGGCGGATGTGGCGGCAACCGGAACAA
CTTTGACACAGAAGAGTACTGCATGGCCGTGTGTGGCAGCGCCAT
TCCTACAACAGCAGCCAGTACCCCTGATGCCGTTGACAAGTATCTC
GAGACACCTGGGGATGAGAATGAACATGCCCATTTCCAGAAAGCC
AAAGAGAGGCTTGAGGCCAAGCACCGAGAGAGAATGTCCCAGGT
CATGAGAGAATGGGAAGAGGCAGAACGTCAAGCAAAGAACTTGC
CTAAAGCTGATAAGAAGGCAGTTATCCAGCATTTCCAGGAGAAGG
TGGAATCTTTGGAACAGGAAGCAGCCAACGAGAGACAGCAGCTGG
TGGAGACACACATGGCCAGAGTGGAAGCCATGCTCAATGACCGCC
GCCGCCTGGCCCTGGAGAACTACATCACCGCTCTGCAGGCTGTTCC
TCCTCGGCCTCGTCACGTGTTCAATATGCTAAAGAAGTATGTACGC
GCAGAACAGAAGGCAGACAGCACACCCTAAAGCATTTCGAGCAT
GTGCGCATGGTGGATCCCAAGAAAGCCGCTCAGATCCGGTCCCAG
GTTATGACACTCCTCCGTGTGATTTATGAGCGCATGAATCAGTCTC
TCTCCCTGCTCTACAACGTGCCTGCAGTGGCCGAGGAGATTCAGGA
TGAAGTTGGT:GTTCTTTGCAGAAGATGTGGGTTCAAACAAAGGTG
CAATCATTGGACTCATGGTGGGCGGTGTTGTCATAGCGACAGTGAT
CGTCATCACCTTGGTGATGCTGAAGAAGAAACAGTACACATCCAT
TCATCATGGTGTGGTGGAGGTTGACGCCGCTGTCACCCCAGAGGA
GCGCCACCTGTCCAAGATGCAGCAGAACGGCTACGAAAATCCAAC
CTACAAGTTCTTTGAGCAGATGCAGAACTAG |

TABLE 1-continued

| SEQ ID NO | Name* | Sequence** |
|---|---|---|
| 16 | cAPP-D2/18-3 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAG<u>A:A</u>AGTTCTTTGAGCAGA TGCAGAAC |

*Nomenclature: c, coding; nc, non-coding; R, RNA; D, DNA; X/Y, junction between exon X/Y; -X, number of variants.
**X:Y indicate intraexonic junctions In some embodiments, the non-classical variant of APP is a RNA sequence encoding for amyloid beta precursor protein or a portion thereof. In some embodiments, the non-classical variant of APP is a RNA sequence comprising intraexonic junctions between exons of APP. In some embodiments, the non-classical variant of APP is a RNA sequence lacking introns between exons of APP. In some embodiments, the non-classical variant of APP is a RNA sequence comprising one or more single nucleotide variant(s) of APP. In some embodiments, the RNA sequence is set forth as in Table 1. In some embodiments, the non-classical variant of APP is a DNA sequence encoding for the amyloid beta precursor protein or a portion thereof. In some embodiments, the non-classical variant of APP is a DNA sequence comprising intraexonic junctions between exons of APP or conventional spliced exon-exon junctions present in APP RNA. In some embodiments, the non-classical variant of APP is a DNA sequence lacking introns between exons of APP. In some embodiments, the non-classical variant of APP is a DNA sequence comprising one or more single nucleotide variant(s) of APP. In some embodiments, the non-classical variant of APP is a peptide sequence of a protein encoded by a whole or a part of the non-classical variant of APP.

Provided herein, in certain embodiments, are non-classical variants of APP, wherein the non-classical variants comprise a single nucleotide variation (SNV). In some embodiments, the non-classical variants comprise one or more SNVs. In some embodiments, the SNV are familial mutations that arise somatically. In some embodiments, the SNV are associated with pathogenic Alzheimer's disease. Exemplary familial mutations associated with pathogenic Alzheimer's disease which translate to amino acid positions in APP include, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translate to amino acid positions in APP include, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N.

In some embodiments, the non-classical variants comprise a SNV in at least one exon of APP. In some embodiments, the non-classical variants comprise one or more SNVs in at least one exon of APP. In some embodiments, the non-classical variants comprise the SNV in one or more exons of APP. In some embodiments, the non-classical variants comprise the SNV in exon 1, 2, 3, 4, 5, 6, 7, 8, 9, 10, 11, 12, 13, 14, 15, 16, 17, 18, or combinations thereof of APP. In some embodiments, the non-classical variants comprise the SNV in exon 17. In some embodiments, the non-classical variants comprise the SNV in the amyloid beta region of APP. In some embodiments, the SNV in APP, which translates to amino acid positions in APP includes, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translates to amino acid positions in APP includes, but are not limited to, A673, A713, T714, V715, I716, V717, T719, and L723, wherein the amino acids correspond to positions 673, 713, 714, 715, 716, 717, 719, and 723 of SEQ ID NO: 17. In some embodiments, the SNV in APP, which translates to amino acid positions in APP includes, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translates to amino acid positions in APP includes, but are not limited to, A673V, A713T, T714I, V715M, V715A, I716M, V717I, V717F, T719P, and L723P.

TABLE 2

Amino Acid Sequence of APP

| SEQ ID NO | Accession No. | Amino Acid Sequence |
|---|---|---|
| 17 | P05067.3 | MLPGLALLLLAAWTARALEVPTDGNAGLLAEPQ IAMFCGRLNMHMNVQNGKWDSDPSGTKTCIDTK EGILQYCQEVYPELQITNVVEANQPVTIQNWCK RGRKQCKTHPHFVIPYRCLVGEFVSDALLVPDK CKFLHQERMDVCETHLHWHTVAKETCSEKSTNL HDYGMLLPCGIDKFRGVEFVCCPLAEESDNVDS ADAEEDDSDVWWGGADTDYADGSEDKVVEVAEE EEVAEVEEEEADDDEDDEDGDEVEEEAEEPYEE ATERTTSIATTTTTTESVEEVVREVCSEQAET GPCRAMISRWYFDVTEGKCAPFFYGGCGGNRNN FDTEEYCMAVCGSAMSQSLLKTTQEPLARDPVK LPTTAASTPDAVDKYLETPGDENEHAHFQKAKE RLEAKHRERMSQVMREWEEAERQAKNLPKADKK AVIQHFQEKVESLEQEAANERQQLVETHMARVE AMLNDRRRLALENYITALQAVPPRPRHVFNMLK KYVRAEQKDRQHTLKHFEHVRMVDPKKAAQIRS QVMTHLRVIYERMNQSLSLLYNVPAVAEEIQDE VDELLQKEQNYSDDVLANMISEPRISYGNDALM PSLTETKTTVELLPVNGEFSLDDLQPWHSFGAD SVPANTENEVEPVDARPAADRGLTTRPGSGLTN IKTEEISEVKMDAEFRHDSGYEVHHQKLVFFAE DVGSNKGAIIGLMVGGVVIATVIVITLVMLKKK QYTSIHHGVVEVDAAVTPEERHLSKMQQNGYEN PTYKFFEQMQN |

In some embodiments, the non-classical variant of APP comprises a sequence as set forth in SEQ ID NO: 1, 2, 3, 4, 5, 6, 7, 8, 9, 10, 11, 12, 13, 14, 15, or 16. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 1. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 2. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 3. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 4. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 5. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 6. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 7. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 8. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 9. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 10. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 11. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 12. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 13. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 14. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 15. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 16.

Methods of Identifying Non-Classical Variants

Described herein are methods for identifying non-classical variants of amyloid precursor protein (APP) gene. In some embodiments, a non-classical variant of APP is identified from an individual with Alzheimer's disease (AD). In some embodiments, a non-classical variant of APP is identified from a brain of an individual with AD. In some embodiments, a non-classical variant of APP is identified in a neuron isolated from an individual with AD. In some embodiments, the neuron is sorted and isolated. In some embodiments, the neuron is sorted and isolated using fluorescence activated nuclear sorting (FANS). In some embodiments, a non-classical variant of APP is identified from RNA extracted from a neuron of an individual with AD. In some embodiments, the RNA is reverse transcribed to cDNA, and a non-classical variant of APP is identified. In some embodiments, a non-classical variant of APP is identified from genomic DNA extracted from a neuron of an individual with AD. In some embodiments, AD is sporadic AD. In some embodiments, AD is familial AD. In some embodiments, a non-classical variant is identified using a control. In some embodiments, the control is an individual that does not have AD.

In some embodiments, a non-classical variant of APP is identified using probes that hybridize to full length APP. In some embodiments, a non-classical variant of APP is identified using probes that hybridize to full length APP comprising only exons of APP. In some embodiments, the probes hybridize to genomic DNA. In some embodiments, the probes are used for in situ hybridization. In some embodiments, the probes hybridize to cDNA of APP. An exemplary probe comprises a sequence as set forth in SEQ ID NO: 21. In some embodiments, the probes hybridize to cDNA of APP and are detected by Southern blot. In some embodiments, the Southern Blot is compared to a gel electrophoresis of cDNA of APP. In some embodiments, a non-classical variant of APP is identified by sequencing cDNA corresponding to cDNA detected by the Southern Blot.

Methods of Diagnostics

Described herein, in certain embodiments, are methods for detecting one or more non-classical variant(s) of amyloid precursor protein (APP) gene in an individual in need thereof. Further described herein, in certain embodiments, are methods for evaluating an individual for risk of developing a disease or disorder characterized by unwanted accumulation of amyloid beta protein comprising: measuring an expression profile or an activity profile of one or more non-classical variant(s) of APP gene from a biological sample from the individual; comparing the expression profile or the activity profile of the one or more non-classical variant(s) of APP to a reference expression profile or activity profile of the one or more non-classical variant(s) of APP derived from a cohort of control individuals; and identifying the individual as having or not having a risk factor for developing the disease or disorder characterized by unwanted accumulation of amyloid beta protein based on a comparison of the expression profile or activity profile to the reference expression profile or activity profile of the cohort of control individuals. Further described herein, in certain embodiments, are methods of diagnosing a disease or disorder in an individual characterized by unwanted accumulation of amyloid beta protein, comprising: identifying the individual as having the disease or disorder characterized by unwanted accumulation of amyloid beta protein by comparing an expression profile or an activity profile of one or more non-classical variant(s) of an APP gene to a reference expression profile or activity profile of the one or more non-classical variant(s) of APP derived from a cohort of control individuals. In some embodiments, the biological sample is a blood sample. In some embodiments, the biological sample comprises RNA, DNA, or protein. In some embodiments, the disease or disorder is Alzheimer's disease. In some embodiments, the Alzheimer's disease is familial Alzheimer's disease (FAD) or sporadic Alzheimer's disease.

In some embodiments, the amyloid beta protein is an amyloidogenic protein or a protein that produces an amyloid like morphology. In some embodiments, the amyloid beta protein is encoded by the one or more non-classical variant(s) of APP. In some embodiments, the amyloid beta protein is a variant peptide or protein comprising amyloid beta that is encoded by the one or more non-classical variant(s) of APP. In some embodiments, the amyloid beta protein is a variant peptide or protein that does not comprise amyloid beta and is encoded by the one or more non-classical variant(s) of APP.

In some embodiments, the expression profile is expression level of the one or more non-classical variant(s) of APP. In some embodiments, the expression profile is expression of a set of different non-classical variant of APP. In some embodiments, the activity profile is activity level of the one or more non-classical variant(s) of APP. In some embodiments, the activity profile is activity of a set of different non-classical variant of APP. In some embodiments, the non-classical variant of APP comprises a portion or all of an exon of the APP gene. In some embodiments, the non-classical variant of APP comprises a portion or all of exon 1, 2, 3, 4, 5, 6, 7, 8, 9, 10, 11, 12, 13, 14, 15, 16, 17, 18, or combinations thereof of the APP gene. In some embodiments, the non-classical variants comprise a portion or all of exon 1, 2, 3, 4, 5, 6, 7, 9, 10, 11, 12, 13, 14, 15, 16, 17, 18, or combinations thereof of APP. In some embodiments, the non-classical variants do no comprise exon 8. In some embodiments, the one or more exon(s) in the one or more non-classical variant(s) of APP is rearranged as compared to control. In some embodiments, the non-classical variant of APP does not comprise exon 8 of the APP gene. In some embodiments, the non-classical variant of APP comprises a sequence as set forth in SEQ ID NO: 1, 2, 3, 4, 5, 6, 7, 8, 9, 10, 11, 12, 13, 14, 15, or 16. In some embodiments, the non-classical variant of APP comprises a single nucleotide variation (SNV). In some embodiments, the non-classical variant of APP comprises one or more SNVs. In some embodiments, the SNV in APP, which translates to amino acid positions in APP includes, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translates to amino acid positions in APP includes, but are not limited to, A673, A713, T714, V715, I716, V717, T719, and L723, wherein the amino acids correspond to positions 673, 713,714, 715, 716, 717, 719, and 723 of SEQ ID NO: 17. In some embodiments, the SNV in APP, which translates to amino acid positions in APP includes, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translates to amino acid positions in APP includes, but are not limited to, A673V, A713T, T714I, V715M, V715A, I716M, V717I, V717F, T719P, and L723P.

Sequencing

In some embodiments, the expression profile of one or more non-classical variant(s) of amyloid precursor protein (APP) gene is measured by sequencing of a biological sample from the individual. In some embodiments, the biological sample comprises RNA or DNA. In some embodiments, sequencing is performed with any appropriate sequencing technology, including but not limited to single molecule real-time sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis.

In some embodiments, the expression profile of one or more non-classical variant(s) of APP is measured by nucleotide sequencing. In some embodiments, the nucleotide sequencing comprises long-read sequencing. In some embodiments, the long-read sequencing is single molecule real-time sequencing. In some embodiments, the single molecule real-time sequencing comprises attaching a different fluorescent dye to each of the nucleic acid bases and using a polymerase. In some embodiments, the polymerase incorporates a single nucleotide comprising the fluorescent dye. In some embodiments, the fluorescent dye is detected to generate a nucleotide sequence. In some embodiments, the polymerase is a DNA polymerase or a RNA polymerase. In some embodiments, the DNA polymerase is a modified polymerase. In some embodiments, a template to be sequenced is a DNA template or a RNA template. In some embodiments, the long-read sequencing does not require a reference genome. In some embodiments, methods for measuring the expression profile comprise preparation of a biological sample prior to sequencing. In some embodiments, DNA is extracted and purified from the biological sample. In some embodiments, RNA is extracted. In some embodiments, RNA is extracted, purified, and reverse transcribed to cDNA. In some embodiments, after RNA or DNA is extracted, the reverse transcribed cDNA or DNA is amplified prior to sequencing. In some embodiments, single molecule real-time sequencing comprises additional preparation of the biological sample prior to sequencing. In some embodiments, the DNA is fragmented. In some embodiments, target regions are amplified to obtain fragmented DNA. In some embodiments, target regions are enriched by hybridization based DNA pull-down. Following fragmentation, in some embodiments, the ends of the DNA are repaired. In some embodiments, hairpin adapters are ligated to the DNA that then hybridizes to a primer. In some embodiments, a nuclease is used to remove DNA that did not ligate to the hairpin adapters. In some embodiments, a DNA polymerase is mixed and the DNA is sequenced.

In some embodiments, the expression profile of one or more non-classical variant(s) of APP is the expression level of one or more non-classical variant(s) of APP. In some embodiments, the expression level is of a set of different non-classical variants of APP. In some embodiments, the expression level is measured following long-read sequencing. In some embodiments, the long-read sequencing is RNA sequencing. In some embodiments, the long-read sequencing is DNA sequencing. In some embodiments, the long-read sequencing is single molecule real-time sequencing. During a long-read sequencing reaction, sequenced base pairs or "reads" are generated. In some embodiments, the expression level is then quantified by counting a number of reads that map to the one or more non-classical variant(s) of APP sequences during the long-read sequencing reaction. In some embodiments, the one or more non-classical variant(s) of APP sequences comprise a sequence as set forth in SEQ ID NO: 1, 2, 3, 4, 5, 6, 7, 8, 9, 10, 11, 12, 13, 14, 15, or 16.

In some embodiments, the long read sequencing measures a change in the APP gene. In some embodiments, the change is a change in DNA of the APP gene. In some embodiments, the DNA is coding DNA. In some embodiments, the DNA is non-coding DNA. In some embodiments, the change is a change in RNA of the APP gene. In some embodiments, the RNA is coding RNA. In some embodiments, the RNA is non-coding RNA. In some embodiments, the change is a change in a protein encoded by the APP gene.

In some embodiments, the long read sequencing measures a single nucleotide variation (SNV) in the APP gene. In some embodiments, the long read sequencing measures one or more SNVs in the APP gene. In some embodiments, the SNV in APP, which translates to amino acid positions in APP includes, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translates to amino acid positions in APP includes, but are not limited to, A673, A713, T714, V715, I716, V717, T719, and L723, wherein the amino acids correspond to positions 673, 713,714, 715, 716, 717, 719, and 723 of SEQ ID NO: 17. In some embodiments, the SNV in APP, which translates to amino acid positions in APP includes, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translates to amino acid positions in APP includes, but are not limited to, A673V, A713T, T714I, V715M, V715A, I716M, V717I, V717F, T719P, and L723P.

Pull-Down Assays

In some embodiments, the expression profile of one or more non-classical variant(s) of the amyloid precursor protein (APP) gene is measured by a pull-down assay. In some embodiments, one or more probe(s) for use in the pull-down assay is designed to hybridize to a portion or all of exon 1, 2, 3, 4, 5, 6, 7, 8, 9, 10, 11, 12, 13, 14, 15, 16, 17, 18, or combinations thereof. In some embodiments, one or more probe(s) for use in the pull-down assay is designed to hybridize to a portion or all of exon 1, 2, 3, 4, 5, 6, 7, 9, 10, 11, 12, 13, 14, 15, 16, 17, 18, or combinations thereof. In some embodiments, the one or more probe(s) for use in the pull-down assay is designed to hybridize to a portion or all of a non-classical variant comprising a sequence as set forth in SEQ ID NO: 1, 2, 3, 4, 5, 6, 7, 8, 9, 10, 11, 12, 13, 14, 15, or 16.

In some embodiments, the one or more probe(s) is labeled with an affinity tag. Exemplary affinity tags include, but are not limited to, biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione.

In some embodiments, following a pull-down assay, one or more non-classical variant(s) of APP are amplified. In some embodiments, the one or more non-classical variant(s) of APP are amplified using primers designed to detect exon 1, 2, 3, 4, 5, 6, 7, 8, 9, 10, 11, 12, 13, 14, 15, 16, 17, or 18. In some embodiments, the one or more non-classical variant(s) of APP are amplified using primers designed to detect exon 1, 2, 3, 4, 5, 6, 7, 9, 10, 11, 12, 13, 14, 15, 16, 17, or 18. In some embodiments, the primers are used to detect one or more non-classical variant comprising a sequence as set forth in SEQ ID NO: 1, 2, 3, 4, 5, 6, 7, 8, 9, 10, 11, 12, 13, 14, 15, or 16. In some embodiments, the one or more non-classical variant is amplified by PCR. In some embodiments, the PCR is qPCR.

Following the pull-down assay, in some embodiments, the one or more non-classical variant(s) of APP are not amplified. In some embodiments, the one or more non-classical variant(s) of APP are visualized using a fluorescent assay, a radioactivity assay, or a luminescent assay. For example, the one or more probes used to hybridize to the one or more non-classical variant(s) of APP further comprises a fluorescent tag that is detected using the fluorescent assay. In some embodiments, the one or more non-classical variant(s) of APP are visualized by gel electrophoresis.

In some embodiments, the pull down assay measures a change in the APP gene. In some embodiments, the change is a change in DNA of the APP gene. In some embodiments, the DNA is coding DNA. In some embodiments, the DNA is non-coding DNA. In some embodiments, the change is a change in RNA of the APP gene. In some embodiments, the RNA is coding RNA. In some embodiments, the RNA is non-coding RNA. In some embodiments, the change is a change in a protein encoded by the APP gene.

Hybridization Assays

In some embodiments, the expression profile of one or more non-classical variant(s) of the amyloid precursor protein (APP) gene is measured by binding of one or probe(s) to one or more non-classical variant(s) of APP. In some embodiments, the one or more probe(s) is a polypeptide. In some embodiments, the one or more probe(s) is a polynucleotide.

In some embodiments, intraexonic rearrangements are detected by measuring binding of the one or more probe(s). In some embodiments, the one or more probe(s) hybridizes to target sequences within at least two exons of APP gene. For example, the one or more probe(s) hybridizes to sequences with one end complementary to a 3' end of one exon of APP and a second end complementary to a 5' end of a downstream exon of APP. In some embodiments, the one or more probe(s) hybridizes to target sequences within at least two exons that are consecutive exons of APP. In some embodiments, the one or more probe(s) hybridizes to target sequences within at least two exons that are non-consecutive exons of APP.

In some embodiments, the one or more probe(s) are provided in an array. In some embodiments, the array comprises one or more probe(s) for measuring an expression profile for one or more non-classical variant(s) of APP. In some embodiments, the one or more probe(s) detects RNA. In some embodiments, the one or more probe(s) detect exonic rearrangements such as intraexonic rearrangements of APP. In some embodiments, the one or more probes hybridize to a portion or all of an exon 1, 2, 3, 4, 5, 6, 7, 8, 9, 10, 11, 12, 13, 14, 15, 16, 17, 18, or combinations thereof of APP. In some embodiments, the one or more probes hybridize to a portion or all of an exon 1, 2, 3, 4, 5, 6, 7, 9, 10, 11, 12, 13, 14, 15, 16, 17, 18, or combinations thereof of APP. For example, the array comprises RNA probes designed to hybridize to the one or more non-classical variant(s) of APP.

In some embodiments, the one or more probe(s) bind to RNA or DNA from the one or more non-classical variant(s) of APP gene. In some embodiments, the one or more probe(s) are used for an amplification reaction. In some embodiments, the amplification reaction is PCR. In some embodiments, the amplification reaction is quantitative such as qPCR. In some embodiments, the PCR reaction utilizes a TaqMan™ or a similar quantitative PCR technology. In some embodiments, at least one primer used in the PCR reaction comprises a sequence as set forth in SEQ ID NO: 19 or 20.

The one or more probe(s), in some embodiments, bind to a protein encoded by the one or more non-classical variant(s) of APP gene. Exemplary methods for detecting binding of the one or more probe(s) include, but are not limited to, enzyme linked immunosorbent assays (ELISA), Western blots, spectroscopy, mass spectrometry, peptide arrays, colorimetry, electrophoresis, isoelectric focusing, immunoprecipitations, immunoassays, and immunofluorescence.

In some embodiments, the expression profile of the one or more non-classical variant(s) of the APP gene is measured by in situ hybridization or immunological hybridization. In some embodiments, the in situ hybridization is performed without amplification. In some embodiments, the in situ hybridization is performed without polymerase dependent amplification. In some embodiments, the in situ hybridization comprises capturing the one or more non-classical variant(s) of APP from the biological sample on a solid support prior to contacting the one or more non-classical variant(s) of APP with the one or more probe(s). In some embodiments, the in situ hybridization is chromogenic in situ hybridization. In some embodiments, the in situ hybridization is fluorescence in situ hybridization. In some embodiments, in situ hybridization allows for detection of intraexonic rearrangements. In some embodiments, in situ hybridization allows for detection for genomic rearrangements such as between introns and exons or between exons and exons. In some embodiments, the one or more probe(s) for in situ hybridization hybridizes to a region spanning an intraexonic rearrangement. For example, for the non-classical variant cAPP-R3/16, the one or more probe(s) hybridize to a region spanning exon 3 and exon 16. In some embodiments, the one or more probe(s) hybridize to a region of a sequence as set forth in SEQ ID NO: 1, 2, 3, 4, 5, 6, 7, 8, 9, 10, 11, 12, 13, 14, 15, or 16.

Described herein, in certain embodiments, one or more probe(s) that hybridize to an intraexonic junction are non-classical variants of APP comprising portions of at least two exons, wherein the at least two exons are linked by intraexonic junctions. In some embodiments, the one or more probe(s) hybridize to an intraexonic junction between exon 1 and exon 2, 3, 4, 5, 6, 7, 8, 9, 10, 11, 12, 13, 14, 15, 16, 17, 18, or combinations thereof. In some embodiments, the one or more probe(s) hybridize to an intraexonic junction between exon 2 and exon 1, 3, 4, 5, 6, 7, 8, 9, 10, 11, 12, 13, 14, 15, 16, 17, 18, or combinations thereof. In some embodiments, the one or more probe(s) hybridize to an intraexonic junction between exon 3 and exon 1, 2, 4, 5, 6, 7, 8, 9, 10, 11, 12, 13, 14, 15, 16, 17, 18, or combinations thereof. In some embodiments, the one or more probe(s) hybridize to an intraexonic junction between exon 4 and exon 1, 2, 3, 5, 6, 7, 8, 9, 10, 11, 12, 13, 14, 15, 16, 17, 18, or combinations thereof. In some embodiments, the one or more probe(s) hybridize to an intraexonic junction between exon 5 and exon 1, 2, 3, 4, 6, 7, 8, 9, 10, 11, 12, 13, 14, 15, 16, 17, 18, or combinations thereof. In some embodiments, the one or more probe(s) hybridize to an intraexonic junction between exon 6 and exon 1, 2, 3, 4, 5, 7, 8, 9, 10, 11, 12, 13, 14, 15, 16, 17, 18, or combinations thereof. In some embodiments, the one or more probe(s) hybridize to an intraexonic junction between exon 7 and exon 1, 2, 3, 4, 5, 6, 8, 9, 10, 11, 12, 13, 14, 15, 16, 17, 18, or combinations thereof. In some embodiments, the one or more probe(s) hybridize to an intraexonic junction between exon 8 and exon 1, 2, 3, 4, 5, 6, 7, 9, 10, 11, 12, 13, 14, 15, 16, 17, 18, or combinations thereof. In some embodiments, the one or more probe(s) hybridize to an intraexonic junction between exon 9 and exon 1, 2, 3, 4, 5, 6, 7, 8, 10, 11, 12, 13, 14, 15, 16, 17, 18, or combinations thereof. In some embodiments, the one or more probe(s) hybridize to an intraexonic junction between exon 10 and exon 1, 2, 3, 4, 5, 6, 7, 8, 9, 11, 12, 13, 14, 15, 16, 17, 18, or combinations thereof. In some embodiments, the one or more probe(s) hybridize to an intraexonic junction between exon 11 and exon 1, 2, 3, 4, 5, 6, 7, 8, 9, 10, 12, 13, 14, 15, 16, 17, 18, or combinations thereof. In some embodiments, the one or more probe(s) hybridize to an intraexonic junction between exon 12 and exon 1, 2, 3, 4, 5, 6, 7, 8, 9, 10, 11, 13, 14, 15, 16, 17, 18, or combinations thereof. In some embodiments, the one or more probe(s) hybridize to an intraexonic junction between exon 13 and exon 1, 2, 3, 4, 5, 6, 7, 8, 9, 10, 11, 12, 14, 15, 16, 17, 18, or combinations thereof. In some embodiments, the one or more probe(s) hybridize to an intraexonic junction between exon 14 and exon 1, 2, 3, 4, 5, 6, 7, 8, 9, 10, 11, 12, 13, 15, 16, 17, 18, or combinations thereof. In some embodiments, the one or more probe(s) hybridize to an intraexonic junction between exon 15 and exon 1, 2, 3, 4, 5, 6, 7, 8, 9, 10, 11, 12, 13, 14, 16, 17, 18, or combinations thereof. In some embodiments, the one or more probe(s) hybridize to an intraexonic junction between exon 16 and exon 1, 2, 3, 4, 5, 6, 7, 8, 9, 10, 11, 12, 13, 14, 15, 17, 18, or combinations thereof. In some embodiments, the one or more probe(s) hybridize to an intraexonic junction between exon 17 and exon 1, 2, 3, 4, 5, 6, 7, 8, 9, 10, 11, 12, 13, 14, 15, 16, 18, or combinations thereof. In some embodiments, the one or more probe(s) hybridize to an intraexonic junction between exon 18 and exon 1, 2, 3, 4, 5, 6, 7, 8, 9, 10, 11, 12, 13, 14, 15, 16, 17, or combinations thereof. In some embodiments, the one or more probe(s) hybridize to an intraexonic junction between exon 1 and exon 11, exon 1 and exon 14, exon 2 and exon 17, exon 2 and exon 14, exon 2 and exon 18, exon 2 and exon 16, exon 3 and exon 16, exon 3 and exon 14, exon 3 and exon 17, exon 6 and exon 17, exon 6 and exon 18, exon 3 and exon 9, exon 2 and exon 9, exon 16 and exon 18, exon 6 and exon 12, exon 5 and exon 16, or exon 16 and exon 17.

In situ hybridization, in some embodiments, comprises probes for detecting one or more non-classical variant(s) of APP. In some embodiments, the probes hybridize to RNA comprising the one or more non-classical variant(s) of APP. In some embodiments, the probes hybridize to DNA comprising the one or more non-classical variant(s) of APP. In some embodiments, the probes hybridize to RNA comprising a portion of a sequence as set forth in SEQ ID NO: 1, 2, 3, 4, 5, 6, 7, 8, 9, 10, 11, 12, 13, 14, 15, or 16. In some embodiments, the probes comprise a base-pairing region complementary to the target nucleic acid, a spacer sequence, and a base-tail sequence. In some embodiments, two tail sequences form a hybridization site for amplification. In some embodiments, the target nucleic acid is visualized following amplification. In some embodiments, the probes hybridize to protein encoded by the non-classical variant of APP. In some embodiments, the probes are removed prior to visualization. In some embodiments, the probes are removed enzymatically, chemically, or mechanically. For example, the probes are removed using restriction enzymes.

In some embodiments, a number of probes are used for in situ hybridization. In some embodiments, in situ hybridization comprises at least or about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more 100 probes. In some embodiments, in situ hybridization comprises at most 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 probes. In some embodiments, a number of probe pairs are used for in situ hybridization. In some embodiments, the number of probe pairs comprises at least or about 1, 2, 3, 4, 5, 6, 7, 8, 9, 10, 11, 12, 13, 14, 15, 16, 17, 18, 19, 20, 25, 30, 35, 40, 45, 50, or more than 50 probe pairs. In some embodiments, in situ hybridization comprises at most 1, 2, 3, 4, 5, 6, 7, 8, 9, 10, 11, 12, 13, 14, 15, 16, 17, 18, 19, 20, 25, 30, 35, 40, 45, or 50 probe pairs. In some embodiments, following hybridization of a probe or a probe pair, the probe or probe pair are amplified prior to visualization.

In some embodiments, a probe is labeled. In some embodiments, a probe is labeled with a radioactive label, a fluorescent label, an enzyme, a chemiluminescent tag, a colorimetric tag, an affinity tag or other labels or tags that are known in the art.

Exemplary affinity tags include, but are not limited to, biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione.

In some embodiments, the fluorescent label is a fluorophore, a fluorescent protein, a fluorescent peptide, quantum dots, a fluorescent dye, a fluorescent material, or variations or combinations thereof.

Exemplary fluorophores include, but are not limited to, Alexa-Fluor® dyes (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, and Alexa Fluor® 750), APC, Cascade Blue, Cascade Yellow and R-phycoerythrin (PE), DyLight 405, DyLight 488, DyLight 550, DyLight 650, DyLight 680, DyLight 755, DyLight 800, FITC, Pacific Blue, PerCP, Rhodamine, and Texas Red, Cy5, Cy5.5, Cy7.

Examples of fluorescent peptides include GFP (Green Fluorescent Protein) or derivatives of GFP (e.g., EBFP, EBFP2, Azurite, mKalamal, ECFP, Cerulean, CyPet, YFP, Citrine, Venus, YPet).

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes. In some embodiments, the fluorescein dye is, but not limited to, 5-carboxyfluorescein, fluorescein-5-isothiocyanate, fluorescein-6-isothiocyanate and 6-carboxyfluorescein. In some embodiments, the rhodamine dye is, but not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, and rhodamine 101 sulfonyl chloride (sold under the tradename of TEXAS RED®). In some embodiments, the cyanine dye is Cy3, Cy3B, Cy3.5, Cy5, Cy5.5, Cy7, IRDYE680, Alexa Fluor 750, IRDye800CW, or ICG.

Fluorescent labels are detected by any suitable method. For example, a fluorescent label is detected by exciting the fluorochrome with the appropriate wavelength of light and detecting the resulting fluorescence, e.g., by microscopy, visual inspection, via photographic film, by the use of electronic detectors such as charge coupled devices (CCDs), or photomultipliers. In some embodiments, the one or more probe(s) are labeled with the same fluorescent label. In some embodiments, the one or more probe(s) are labeled with different fluorescent labels.

In some embodiments, the expression profile is expression level of the one or more non-classical variant(s) of APP. In some embodiments, the expression level is of a set of different non-classical variants of APP. In some embodiments, the expression level is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the expression level is measured using qPCR. In some embodiments, the qPCR comprises use of fluorescent dyes or fluorescent probes. In some embodiments, the fluorescent dye is an intercalating dye. Examples of intercalating dyes include, but are not limited to, intercalating dyes include SYBR green I, SYBR green II, SYBR gold, ethidium bromide, methylene blue, Pyronin Y, DAPI, acridine orange, Blue View, or phycoerythrin. In some embodiments, the qPCR comprises use of more than one fluorescent probe. In some embodiments, the use of more than one fluorescent probes allows for multiplexing. For example, different non-classical variants are hybridized to different fluorescent probes and can be detected in a single qPCR reaction.

In some embodiments, the probe is used for visualization of the one or more non-classical variant(s) of APP in an individual. In some embodiments, the probe is visualized by X-Ray, fluoroscopes, ultrasound, CT-scan, PET scan, magnetic resonance image (MRIs), or electromagnetic field.

In some embodiments, the hybridization assay measures a change in the APP gene. In some embodiments, the change is a change in DNA of the APP gene. In some embodiments, the DNA is coding DNA. In some embodiments, the DNA is non-coding DNA. In some embodiments, the change is a change in RNA of the APP gene. In some embodiments, the RNA is coding RNA. In some embodiments, the RNA is non-coding RNA. In some embodiments, the change is a change in a protein encoded by the APP gene.

Samples

Described herein, in certain embodiments are methods for diagnosing an individual having or suspected of having Alzheimer's disease by measuring the expression profile or the activity profile of the one or more non-classical variant(s) of amyloid precursor protein (APP) gene. In some embodiments, the expression profile or the activity profile of the one or more non-classical variant(s) of APP is associated with unwanted accumulation of amyloid beta protein but the individual does not have Alzheimer's disease.

In some embodiments, the expression profile or the activity profile is determined from a biological sample from the individual. In some embodiments, the biological sample comprises RNA or DNA. In some embodiments, the RNA is pre-mRNA. In some embodiments, the RNA is mRNA. In some embodiments, the DNA is nuclear DNA. In some embodiments, the DNA is extrachromosomal or extranuclear DNA. In some embodiments, the DNA is circular DNA.

In some embodiments, the biological sample is from a blood sample. The blood sample is taken, for example, from the individual by a blood draw. In some embodiments, the blood sample is processed by centrifugation such as by density centrifugation. In some embodiments, the blood sample is treated with a red blood cell lysis agent. In some embodiments, the blood sample comprises cells from the Central Nervous System (e.g., neurons, astrocytes, or microglia) that are released during break down of the blood brain barrier. In some embodiments, the biological sample is from cerebrospinal fluid. In some embodiments, the cerebrospinal fluid comprises cells from the Central Nervous System (e.g., neurons, astrocytes, or microglia) that are released during break down of the blood brain barrier.

A biological sample, in some embodiments, comprises exosomes. Exosomes are cell-derived vesicles that are released from many cell types including, but not limited to, dendritic cells (DCs), lymphocytes, platelets, mast cells, epithelial cells, endothelial cells, and neurons. In some embodiments, the exosomes are found in blood. In some embodiments, the exosomes are found in cerebrospinal fluid. In some embodiments, the biological sample comprises exosomes from the blood. In some embodiments, the biological sample comprises exosomes from cerebrospinal fluid.

In some embodiments, nucleic acid is extracted from the biological sample. In some embodiments, the nucleic acid is DNA. In some embodiments, the DNA is genomic DNA. In some embodiments, the DNA is extrachromosomal DNA. In some embodiments, the DNA is circular DNA. In some embodiments, the nucleic acid is RNA. The nucleic acid, in some embodiments, is extracted using any technique that does not interfere with subsequent analysis. For example, the nucleic acid is extracted using alcohol precipitation using ethanol, methanol, or isopropyl alcohol. In some embodiments, the nucleic acid is extracted using phenol, chloroform, or any combination thereof. In some embodiments, the nucleic acid is extracted using cesium chloride. In some embodiments, the nucleic acid is extracted using sodium, potassium or ammonium acetate or any other salt commonly used to precipitate DNA. In some embodiments, the nucleic acid is extracted using utilizes a column or resin based nucleic acid purification. In some embodiments, after extraction the nucleic acid is stored in water, Tris buffer, or Tris-EDTA buffer before subsequent analysis. For example, storage is less than 8° C., 4° C., −20° C., or −70° C. In some embodiments, the nucleic acid is stored for 1, 2, 3, 4, 5, 6, or 7 days. In some embodiments, the nucleic acid is stored for 1, 2, 3, or 4 weeks. In some embodiments, the nucleic acid is stored for 1, 2, 3, 4, 5, 6, 7, 8, 9, 10, 11, or 12 months.

Described herein, in certain embodiments, are methods for evaluating an individual for risk of developing a disease or disorder characterized by unwanted accumulation of amyloid beta protein from a biological sample. In some embodiments, methods for evaluating the individual comprise measuring the expression profile or the activity profile of the one or more non-classical variant(s) of APP. In some embodiments, the one or more non-classical variant(s) of APP comprise a portion or all of an exon of APP gene. For example, the one or more non-classical variant(s) of APP comprise a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) of APP comprise a portion or all of exon 1, 2, 3, 4, 5, 6, 7, 9, 10, 11, 12, 13, 14, 15, 16, 17, 18, or combinations thereof. In some embodiments, the one or more non-classical variant(s) of APP does not comprise exon 8. In some embodiments, the one or more non-classical variant(s) of APP comprise a sequence as set forth in SEQ ID NO: 1, 2, 3, 4, 5, 6, 7, 8, 9, 10, 11, 12, 13, 14, 15, or 16. In some embodiments, the non-classical variants comprise a single nucleotide variation (SNV) in APP, which translate to amino acid positions in APP include, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translate to amino acid positions in APP include, but are not limited to, A673, A713, T714, V715, I716, V717, T719, and L723, wherein the amino acids correspond to positions 673, 713,714, 715, 716, 717, 719, and 723 of SEQ ID NO: 17. In some embodiments, the SNV in APP, which translate to amino acid positions in APP include, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translate to amino acid positions in APP include, but are not limited to, A673V, A713T, T714I, V715M, V715A, I716M, V717I, V717F, T719P, and L723P. In some embodiments, the non-classical variants comprise one or more SNVs. In some embodiments, the expression profile is measured by long-read sequencing. In some embodiments, the long read-sequencing is single molecule real-time sequencing. In some embodiments, the expression profile is measured using probe-based assays. For example, the expression profile is measured by quantitative-PCR, in situ hybridization, or pull down assays.

Further described herein, in certain embodiments, are methods for detecting one or more non-classical variant(s) of an APP gene in an individual in need thereof, comprising: detecting an expression profile or an activity profile of the one or more non-classical variant(s) of the APP gene in a biological sample from the individual by a method comprising long-read sequencing of the biological sample. In some embodiments, the biological sample is a blood sample. In some embodiments, the biological sample comprises RNA or DNA. In some embodiments, the one or more non-classical variant(s) of APP comprise a portion or all of an exon of APP gene. In some embodiments, the one or more non-classical variant(s) of APP comprise a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) of APP comprise a portion or all of exon 1, 2, 3, 4, 5, 6, 7, 9, 10, 11, 12, 13, 14, 15, 16, 17, 18, or combinations thereof. In some embodiments, the one or more non-classical variant(s) of APP does not comprise exon 8. In some embodiments, the non-classical variants comprise a single nucleotide variation (SNV) in APP, which translate to amino acid positions in APP include, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translate to amino acid positions in APP include, but are not limited to, A673, A713, T714, V715, I716, V717, T719, and L723, wherein the amino acids correspond to positions 673, 713,714, 715, 716, 717, 719, and 723 of SEQ ID NO: 17. In some embodiments, the SNV in APP, which translate to amino acid positions in APP include, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translate to amino acid positions in APP include, but are not limited to, A673V, A713T, T714I, V715M, V715A, I716M, V717I, V717F, T719P, and L723P. In some embodiments, the one or more non-classical variant(s) of APP comprise a sequence as set forth in SEQ ID NO: 1, 2, 3, 4, 5, 6, 7, 8, 9, 10, 11, 12, 13, 14, 15, or 16.

Further described herein, in certain embodiments, are methods of detecting one or more non-classical variant(s) of an APP gene in an individual in need thereof, comprising: detecting an expression profile or an activity profile of the one or more non-classical variant(s) of the APP gene in the biological sample from the individual by a method comprising binding of one or more probe(s) to the one or more non-classical variant(s) of APP. In some embodiments, the biological sample is a blood sample. In some embodiments, the biological sample comprises RNA, DNA, or protein. In some embodiments, the one or more non-classical variant(s) of APP comprise a portion or all of an exon of APP gene. In some embodiments, the one or more non-classical variant(s) of APP comprise a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) of APP comprise a portion or all of exon 1, 2, 3, 4, 5, 6, 7, 9, 10, 11, 12, 13, 14, 15, 16, 17, 18, or combinations thereof. In some embodiments, the one or more non-classical variant(s) of APP does not comprise exon 8. In some embodiments, the single nucleotide variation (SNV) in APP, which translates to amino acid positions in APP includes, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNVs in APP, which translate to amino acid positions in APP include, but are not limited to, A673, A713, T714, V715, I716, V717, T719, and L723, wherein the amino acids correspond to positions 673, 713, 714, 715, 716, 717, 719, and 723 of SEQ ID NO: 17. In some embodiments, the SNVs in APP, which translate to amino acid positions in APP include, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNVs in APP, which translate to amino acid positions in APP include, but are not limited to, A673V, A713T, T714I, V715M, V715A, I716M, V717I, V717F, T719P, and L723P. In some embodiments, the one or more non-classical variant(s) of APP comprise a sequence as set forth in SEQ ID NO: 1, 2, 3, 4, 5, 6, 7, 8, 9, 10, 11, 12, 13, 14, 15, or 16.

In some embodiments, the expression profile or the activity profile of an individual at risk of developing a disease or disorder characterized by unwanted accumulation of amyloid beta protein is compared to a reference expression profile or activity profile from a cohort of control individuals. In some embodiments, a presence or absence of one or more non-classical variant(s) of APP is compared to the reference expression profile or activity from the cohort of control individuals. In some embodiments, the expression profile is expression of a set of different non-classical variant(s) of APP. In some embodiments, the activity profile is activity of a set of different non-classical variant(s) of APP. In some embodiments, the non-classical variant of APP comprises a portion or all of an exon of the APP gene. In some embodiments, the non-classical variant of APP comprises a portion or all of exon 1, 2, 3, 4, 5, 6, 7, 8, 9, 10, 11, 12, 13, 14, 15, 16, 17, 18, or combinations thereof of the APP gene. In some embodiments, the one or more non-classical variant(s) of APP comprise a portion or all of exon 1, 2, 3, 4, 5, 6, 7, 9, 10, 11, 12, 13, 14, 15, 16, 17, 18, or combinations thereof. In some embodiments, the one or more non-classical variant(s) of APP does not comprise exon 8. In some embodiments, the non-classical variant of APP comprises a single nucleotide variation (SNV). In some embodiments, the non-classical variant of APP comprises one or more SNVs. In some embodiments, the SNV in APP, which translate to amino acid positions in APP include, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translate to amino acid positions in APP include, but are not limited to, A673, A713, T714, V715, I716, V717, T719, and L723, wherein the amino acids correspond to positions 673, 713, 714, 715, 716, 717, 719, and 723 of SEQ ID NO: 17. In some embodiments, the SNV in APP, which translate to amino acid positions in APP include, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translate to amino acid positions in APP include, but are not limited to, A673V, A713T, T714I, V715M, V715A, I716M, V717I, V717F, T719P, and L723P. In some embodiments, the one or more exon(s) in the one or more non-classical variant(s) of APP is rearranged as compared to control. In some embodiments, the non-classical variant of APP does not comprise exon 8 of the APP gene. In some embodiments, the non-classical variant of APP comprises a sequence as set forth in SEQ ID NO: 1, 2, 3, 4, 5, 6, 7, 8, 9, 10, 11, 12, 13, 14, 15, or 16.

In some embodiments, the expression profile is expression level. In some embodiments, the expression level of the one or more non-classical variants is at least or about 50%, 100%, 200%, 300%, 400%, 500%, 600%, 700%, or more than 700% increased or elevated as compared to the expression level from the cohort of control individuals. In some embodiments, the activity profile is activity level. In some embodiments, the activity level of the one or more non-classical variants is at least or about 50%, 100%, 200%, 300%, 400%, 500%, 600%, 700%, or more than 700% increased or elevated as compared to the activity level from the cohort of control individuals. In some embodiments, the expression profile or activity profile is used to detect the presence of one or more non-classical variant(s) of APP.

In some embodiments, the expression profile or the activity profile is used to diagnose an individual. In some embodiments, the individual has a disease or disorder characterized by unwanted accumulation of amyloid beta protein. In some embodiments, the individual has or is suspected of having Alzheimer's disease. In some embodiments, the individual is diagnosed with Alzheimer's disease by measuring the expression profile or the activity profile of the one or more non-classical variant(s) of APP. In some embodiments, the individual is diagnosed with Alzheimer's disease by measuring the expression profile or the activity profile of the one or more non-classical variant(s) of APP and comparing the expression profile or the activity profile to a reference expression profile or activity profile from a cohort of control individuals. In some embodiments, the individual is diagnosed with Alzheimer's disease when one or more exon(s) in the one or more non-classical variant(s) of APP is rearranged as compared to a control. In some embodiments, the expression profile is expression level. In some embodiments, the individual is diagnosed with Alzheimer's disease when the expression level is at least or about 50%, 100%, 200%, 300%, 400%, 500%, 600%, 700%, or more than 700% increased or elevated as compared to the expression level from the cohort of control individuals. In some embodiments, the activity profile is activity level. In some embodiments, the individual is diagnosed with Alzheimer's disease when the activity level is at least or about 50%, 100%, 200%, 300%, 400%, 500%, 600%, 700%, or more than 700% increased or elevated as compared to the activity level from the cohort of control individuals.

In some embodiments, the expression profile or the activity profile is used to more accurately diagnose or treat an individual having a disease or disorder. In some embodiments, use of the expression profile or the activity profile is at least or about 15%, 20%, 25%, 30%, 35%, 40%, 45%, 50%, 55%, 60%, 65%, 70%, 75%, 80%, 85%, 90%, 95% or more than 95% more accurate at diagnosing a disease or disorder. In some embodiments, use of the expression profile or the activity profile is at least or about 1.5×, 2×, 2.5×, 3×, 3.5×, 4.0×, 4.5×, 5×, 6×, 7×, 8×, 9×, 10×, or more than 10× more accurate at diagnosing a disease or disorder. In some embodiments, the disease or disorder is Alzheimer's disease. In some embodiments, methods as described herein for accurately diagnosing or treating Alzheimer's disease are improved as compared to methods comprising neurological tests, mental exams, or brain imaging (e.g. MRI, CT, or PET scans).

In some embodiments, determining whether the individual has or is predisposed to Alzheimer's disease is based on the expression profile or the activity profile from, wherein a likelihood of having or being predisposed to Alzheimer's disease is increased when the expression profile or the activity profile is elevated compared to a reference expression profile or reference activity profile of the one or more non-classical variant(s) derived from a cohort of control individuals. Methods as described herein for determining a likelihood of having or being predisposed to Alzheimer's disease, in some embodiments, are improved as compared to methods comprising neurological tests, mental exams, or brain imaging (e.g. MRI, CT, or PET scans). In some embodiments, the likelihood of having or being predisposed to Alzheimer's disease is increased by at least or about 15%, 20%, 25%, 30%, 35%, 40%, 45%, 50%, 55%, 60%, 65%, 70%, 75%, 80%, 85%, 90%, 95% or more than 95% by determining the expression profile or activity profile of the one or more non-classical variant(s). In some embodiments, the likelihood of having or being predisposed to Alzheimer's disease is increased by at least or about 1.5×, 2×, 2.5×, 3×, 3.5×, 4.0×, 4.5×, 5×, 6×, 7×, 8×, 9×, 10×, or more than 10× by determining the expression profile or activity profile of the one or more non-classical variant(s).

In some embodiments, the expression profile or the activity profile is used for treating an individual having a disease or disorder. In some embodiments, the expression profile or the activity profile is associated with Alzheimer's disease. In some embodiments, a therapeutic agent is administered based on the expression profile or the activity profile. In some embodiments, the therapeutic agent is optimized based on the expression profile or the activity profile. In some embodiments, the expression profile or the activity profile is measured prior to a treatment, during a treatment, or after a treatment. For example the expression profile or the activity profile is measured at 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years before treatment. In some embodiments, the expression profile or the activity profile is measured at 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years occurs after treatment.

Therapeutic Agents

Disclosed herein, in certain embodiments, are agents for treating a disease or disorder characterized by unwanted accumulation of amyloid beta protein. Further disclosed herein, in certain embodiments, are methods of treating a disease or disorder characterized by unwanted accumulation of amyloid beta protein in an individual in need thereof, comprising: administering to the individual an agent that inhibits activity of one or more non-classical variant(s) of an amyloid precursor protein (APP) gene. Further disclosed herein, in certain embodiments, are methods of diagnosing and treating a disease or disorder characterized by unwanted accumulation of amyloid beta protein in an individual in need thereof, comprising: identifying the individual as having the disease or disorder characterized by unwanted accumulation of amyloid beta protein if binding of one or more probe(s) to one or more non-classical variant(s) of an APP gene is measured; and administering to the individual having the expression profile or the activity profile of the one or more non-classical variant(s) of APP an agent that inhibits activity of the one or more non-classical variant(s) of APP. Further disclosed herein, in certain embodiments, are methods of diagnosing and treating a disease or disorder characterized by unwanted accumulation of amyloid beta protein in an individual in need thereof, comprising: identifying the individual as having the disease or disorder characterized by unwanted accumulation of amyloid beta protein if an expression profile or an activity profile of one or more non-classical variant(s) of an APP gene is measured by a method comprising long-read sequencing of a biological sample from the individual; and administering to the individual having the expression profile or the activity profile of the one or more non-classical variant(s) of APP an agent that inhibits activity of the one or more non-classical variant(s) of APP.

In some embodiments, the agents inhibit an expression profile of the one or more non-classical variant(s) of APP. In some embodiments, the expression profile is expression level. In some embodiments, the expression profile is expression of a set of different non-classical variants. In some embodiments, the agents inhibit activity of the one or more non-classical variant(s) of APP.

In some embodiments, the one or more non-classical variant(s) of APP comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) of APP comprise a portion or all of exon 1, 2, 3, 4, 5, 6, 7, 9, 10, 11, 12, 13, 14, 15, 16, 17, 18, or combinations thereof. In some embodiments, the one or more non-classical variant(s) of APP does not comprise exon 8. In some embodiments, the one or more exon(s) in the one or more non-classical variant(s) of APP is rearranged as compared to a control. In some embodiments, the one or more non-classical variant(s) of APP comprises a sequence as set forth in SEQ ID NO: 1, 2, 3, 4, 5, 6, 7, 8, 9, 10, 11, 12, 13, 14, 15, or 16.

In some embodiments, the agents inhibit unwanted accumulation of amyloid beta protein. In some embodiments, the unwanted accumulation of amyloid beta protein is associated with a disease or disorder. In some embodiments, the disease or disorder is Alzheimer's disease. In some embodiments, the Alzheimer's disease is familial Alzheimer's disease or sporadic Alzheimer's disease. In some embodiments, the agents inhibit plaque formation comprising a portion of or all amyloid beta. In some embodiments, the agents inhibit soluble amyloid beta protein. In some embodiments, the unwanted accumulation of amyloid beta protein is associated with one or more non-classical variant(s) of APP.

In some embodiments, the agents target one or more non-classical variant(s) of APP gene or protein thereof. Exemplary agents include, but are not limited to, an antibody, an antigen binding fragment, a RNA interfering agent (RNAi), a small interfering RNA (siRNA), a short hairpin RNA (shRNA), a microRNA (miRNA), an antisense oligonucleotide (AON), a peptide, a peptidomimetic, a small molecule, or an aptamer.

In some embodiments, the agent is an N-methyl-D-aspartate (NMDA) receptor antagonist, or an anti-amyloid beta antibody. In some embodiments, the cholinesterase inhibitor is selected from the group consisting of Donepezil, Galantamine, and Rivastigmine. In some embodiments, the NMDA receptor antagonist is memantine. In some embodiments, the anti-amyloid beta antibody is selected from the group consisting of Bapineuzumab, Solanezumab, Gantenerumab, Crenezumab, BAN2401, Ponezumab, and Aducanumab. In some embodiments, the N-methyl-D-aspartate (NMDA) receptor antagonist, or an anti-amyloid beta antibody is administered in conjunction with an agent that targets one or more non-classical variant(s) of APP gene or protein thereof. In some embodiments, the agent is an antibody, an antigen binding fragment, a RNA interfering agent (RNAi), a small interfering RNA (siRNA), a short hairpin RNA (shRNA), a microRNA (miRNA), an antisense oligonucleotide (AON), a peptide, a peptidomimetic, a small molecule, or an aptamer that targets the one or more non-classical variant(s) of APP gene or protein thereof.

In some embodiments, the N-methyl-D-aspartate (NMDA) receptor antagonist, or an anti-amyloid beta antibody is administered prior to administration of an agent that targets one or more non-classical variant(s) of APP gene or protein thereof. In some embodiments, the N-methyl-D-aspartate (NMDA) receptor antagonist, or an anti-amyloid beta antibody is administered up to 1 day, up to 2 days, up to 3 days, up to 5 days, or more than 5 days prior to administration of an agent that targets one or more non-classical variant(s) of APP gene or protein thereof. In some embodiments, the N-methyl-D-aspartate (NMDA) receptor antagonist, or an anti-amyloid beta antibody is administered singly, or over a time course, such as daily, multiple times weekly, weekly, biweekly, monthly or less frequently prior to administration of an agent that targets one or more non-classical variant(s) of APP gene or protein thereof.

In some embodiments, the N-methyl-D-aspartate (NMDA) receptor antagonist, or an anti-amyloid beta antibody is administered prior to administration of an agent that targets one or more non-classical variant(s) of APP gene or protein thereof. In some embodiments, the N-methyl-D-aspartate (NMDA) receptor antagonist, or an anti-amyloid beta antibody is administered up to 1 day, up to 2 days, up to 3 days, up to 5 days, or more than 5 days prior to administration of an agent that targets one or more non-classical variant(s) of APP gene or protein thereof. In some embodiments, the N-methyl-D-aspartate (NMDA) receptor antagonist, or an anti-amyloid beta antibody is administered singly, or over a time course, such as daily, multiple times weekly, weekly, biweekly, monthly or less frequently prior to administration of an agent that targets one or more non-classical variant(s) of APP gene or protein thereof.

In some embodiments, the agent is a small molecule. In some embodiments, the small molecule is an antagonist of APP. In some embodiments, the small molecule is an antagonist of one or more non-classical variant(s) of APP. In some embodiments, the one or more non-classical variant(s) of APP comprises a sequence as set forth in SEQ ID NO: 1, 2, 3, 4, 5, 6, 7, 8, 9, 10, 11, 12, 13, 14, 15, or 16. In some embodiments, the small molecule is an antagonist of protein encoded by the APP gene.

In some embodiments, the agent is an antibody. Exemplary antibodies include, but are not limited to, a monoclonal antibody, a polyclonal antibody, a bi-specific antibody, a multispecific antibody, a grafted antibody, a human antibody, a humanized antibody, a synthetic antibody, a chimeric antibody, a camelized antibody, a single-chain Fvs (scFv), a single chain antibody, a Fab fragment, a F(ab') fragment, disulfide-linked Fvs (sdFv), an intrabody, an anti-idiotypic (anti-Id) antibody, or ab antigen-binding fragments thereof. In some embodiments, the antibody comprises immunoglobulin molecules and immunologically active fragments of immunoglobulin molecules, e.g., molecules that contain an antigen binding site. Immunoglobulin molecules are of any type, class (e.g., IgG, IgE, IgM, IgD, IgA and IgY), or subclass (e.g., IgG1, IgG2, IgG3, IgG4, IgA1 and IgA2).

In some embodiments, the antibody selectively binds to a protein encoded by one or more non-classical variant(s) of APP gene. "Selectively binds" refers to the preference of an antibody to interact with one molecule as compared to another.

In some embodiments, the antibody specifically binds to a protein encoded by one or more non-classical variant(s) of APP gene. The phrase "specifically binds" when referring to the interaction between an antibody or other binding molecule and a protein or polypeptide or epitope, typically refers to an antibody or other binding molecule that recognizes and detectably binds with high affinity to the target of interest. Preferably, under designated or physiological conditions, the specified antibodies or binding molecules bind to a particular polypeptide, protein or epitope yet does not bind in a significant or undesirable amount to other molecules present in a biological sample. For example, the specified antibody or binding molecule does not undesirably cross-react with non-target antigens and/or epitopes.

In some embodiments, the antibody binds to a protein encoded by the one or more non-classical variant(s) of APP. In some embodiments, the antibody binds to a protein encoded by the one or more non-classical variant(s) of APP comprising a sequence as set forth in SEQ ID NO: 1, 2, 3, 4, 5, 6, 7, 8, 9, 10, 11, 12, 13, 14, 15, or 16. In some embodiments, the antibody does not bind to wild-type protein.

In some embodiments, agents for inhibiting one or more non-classical variant(s) of APP comprise an antisense RNA that hybridizes to a target RNA and inhibits the activity. In some embodiments, the antisense RNA stringently hybridizes to the target RNA and inhibits the activity. In some embodiments, the target RNA is one or more non-classical variant. In some embodiments, the target RNA is one or more non-classical variant comprising a sequence as set forth in SEQ ID NO: 1, 2, 3, 4, 5, 6, 7, 8, 9, 10, 11, 12, 13, 14, 15, or 16.

In some embodiments, the agent is an antisense RNA molecule. Exemplary antisense RNA molecules include, but are not limited to, RNAi, siRNA, shRNA, or miRNA. In some embodiments, the antisense RNA is double stranded or single stranded. In some embodiments, the antisense RNA comprises about 1 to about 50 nucleotides. In some embodiments, the antisense RNA comprises about 5 to about, about 5 to about 30, about 10 to about 30, about 15 to about 25, or about 20 to about 25 nucleotides. In some embodiments, the antisense RNA is at least or about 70%, 75%, 80%, 85%, 90%, 95%, 98%, 99%, or 100% complementary to the target RNA.

In some embodiments, the antisense RNA inhibits activity of APP. In some embodiments, the antisense RNA is a double-stranded antisense RNA molecule (e.g., siRNA, miRNA, shRNA) that down-regulates expression of APP, wherein one of the strands of the double-stranded antisense RNA molecule comprises a nucleotide sequence that is complementary to a nucleotide sequence of APP RNA encoded by APP or a portion thereof, and wherein the second strand of the double-stranded antisense RNA molecule comprises a nucleotide sequence substantially similar to the nucleotide sequence of APP or RNA encoded by APP or a portion thereof. In some embodiments, the antisense RNA is a double-stranded antisense RNA molecule that down-regulates expression of APP, wherein each strand of the antisense RNA molecule comprises about 15 to 25, 18 to 24, or 19 to about 23 nucleotides, and wherein each strand comprises at least about 14, 17, or 19 nucleotides that are complementary to the nucleotides of the other strand. In some embodiments, the antisense RNA is a double-stranded antisense RNA molecule that down-regulates expression of APP, wherein each strand of the antisense RNA molecule comprises about 19 to about 23 nucleotides, and wherein each strand comprises at least about 19 nucleotides that are complementary to the nucleotides of the other strand. In some embodiments, the RNA interfering activity occurs within a cell. In other embodiments, the RNA interfering activity occurs in a reconstituted in vitro system.

In some embodiments, the antisense RNA is a single-stranded antisense RNA molecule that down-regulates expression of APP, wherein the single-stranded antisense RNA molecule comprises a nucleotide sequence that is complementary to a nucleotide sequence of APP or RNA encoded by APP or a portion thereof. In some embodiments, antisense RNA is a single-stranded antisense RNA molecule that down-regulates expression of APP, wherein the antisense RNA molecule comprises about 15 to 25, 18 to 24, or 19 to about 23 nucleotides. In some embodiments, antisense RNA molecule is a single-stranded antisense RNA molecule that down-regulates expression of APP, wherein the antisense RNA molecule comprises about 19 to about 23 nucleotides. In some embodiments, the RNA interfering activity occurs within a cell. In other embodiments, the RNA interfering activity occurs in a reconstituted in vitro system.

In some embodiments, the antisense RNA molecule is a double-stranded polynucleotide molecule comprising self-complementary sense and antisense regions, wherein the antisense region comprises a nucleotide sequence that is complementary to a nucleotide sequence in a target nucleic acid molecule or a portion thereof and the sense region has a nucleotide sequence corresponding to the target nucleic acid sequence or a portion thereof. In some embodiments, the antisense RNA molecule is assembled from two separate polynucleotides, where one strand is the sense strand and the other is the antisense strand, wherein the antisense and sense strands are self-complementary (e.g., each strand comprises a nucleotide sequence that is complementary to the nucleotide sequence in the other strand; such as where the antisense strand and sense strand form a duplex or double-stranded structure, for example wherein the double-stranded region is about 19, 20, 21, 22, 23, or more base pairs); the antisense strand comprises a nucleotide sequence that is complementary to a nucleotide sequence in a target nucleic acid molecule or a portion thereof and the sense strand comprises a nucleotide sequence corresponding to the target nucleic acid sequence or a portion thereof. In some embodiments, the antisense RNA molecule is assembled from a single oligonucleotide, where the self-complementary sense and antisense regions of the antisense RNA molecule are linked by means of a nucleic acid based or non-nucleic acid-based linker(s).

In some embodiments, the antisense RNA molecule is a polynucleotide with a duplex, asymmetric duplex, hairpin, or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region has a nucleotide sequence corresponding to the target nucleic acid sequence or a portion thereof. In other embodiments, the antisense RNA molecule is a circular single-stranded polynucleotide having two or more loop structures and a stem comprising self-complementary sense and antisense regions, wherein the antisense region comprises a nucleotide sequence that is complementary to a nucleotide sequence in a target nucleic acid molecule or a portion thereof and the sense region has a nucleotide sequence corresponding to the target nucleic acid sequence or a portion thereof, and wherein the circular polynucleotide is processed either in vivo or in vitro to generate an active antisense RNA molecule capable of mediating RNA interfering activity. In additional embodiments, the antisense RNA molecule also comprises a single-stranded polynucleotide having a nucleotide sequence complementary to a nucleotide sequence in a target nucleic acid molecule or a portion thereof, wherein the single stranded polynucleotide further comprises a terminal phosphate group, such as a 5'-phosphate, or 5',3'-diphosphate.

In some embodiments, an asymmetric duplex is a linear antisense RNA molecule comprising an antisense region, a loop portion that comprises nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin antisense RNA molecule comprises an antisense region having length sufficient to mediate RNA interfering activity in a cell or in vitro system (e.g., about 19 to about 22 nucleotides) and a loop region comprising about 4 to about 8 nucleotides, and a sense region having about 3 to about 18 nucleotides that are complementary to the antisense region. In some embodiments, the asymmetric hairpin the antisense RNA molecule also comprises a 5'-terminal phosphate group that is chemically modified. In additional embodiments, the loop portion of the asymmetric hairpin antisense RNA molecule comprises nucleotides, non-nucleotides, linker molecules, or conjugate molecules.

In some embodiments, an asymmetric duplex is an antisense RNA molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex antisense RNA molecule comprises an antisense region having length sufficient to mediate RNA interfering activity in a cell or in vitro system (e.g., about 19 to about 22 nucleotides) and a sense region having about 3 to about 18 nucleotides that are complementary to the antisense region.

In some embodiments, an antisense RNA inhibits activity of a target RNA in a cleavage-dependent process. For example, the cleavage-dependent process involves the RNA-induced silencing complex (RISC). In some embodiments, the antisense RNA (e.g., siRNA) comprises a passenger strand and guide strand. The guide strand pairs with a complementary sequence in a mRNA molecule and induces cleavage by an RNase H endonuclease of the RISC complex. In some embodiments, the RNase H endonuclease is Argonaute. In some embodiments, an antisense RNA inhibits activity in a cleavage-independent process. For example, the antisense RNA (e.g., miRNA) comprises nucleotide mismatches with their targets and effect gene silencing through translational repression of the target gene.

In some embodiments, an antisense RNA inhibits the one or more non-classical variant(s) of APP gene. In some embodiments, the antisense RNA inhibits pre-mRNA. In some embodiments, the antisense RNA inhibits mRNA. In some embodiments, the antisense RNA alters various functions of the target RNA. In some embodiments, the antisense RNA alters splicing of the RNA to yield one or more mRNA species. In some embodiments, the antisense RNA alters translation of protein from RNA. In some embodiments, the antisense RNA alters translocation of the RNA to the site of protein translation. In some embodiments, the antisense RNA alters a catalytic activity of the RNA or which is facilitated by the RNA. Alternatively or in combination, the antisense RNA reduces an amount of pre-mRNA.

In some embodiments, the one or more non-classical variant(s) comprise exons that are inverted. For example, the one or more non-classical variant(s) of APP comprises one or more exons of APP that are inverted. In some embodiments, the one or more non-classical variant(s) of APP comprises one or more exons of APP and one or more exons of APP that are inverted. In some embodiments, agents for inhibiting one or more non-classical variant(s) of APP, wherein the one or more exons of APP are inverted, comprise a sense RNA that hybridizes to a target RNA and inhibits the activity. In some embodiments, the sense RNA stringently hybridizes to the target RNA and inhibits the activity. In some embodiments, the target RNA is one or more non-classical variants of APP comprising inverted exons of APP.

In some embodiments, the agent is a sense RNA molecule. In some embodiments, the sense RNA is double stranded or single stranded. In some embodiments, the sense RNA comprises about 1 to about 50 nucleotides. In some embodiments, the sense RNA comprises about 5 to about, about 5 to about 30, about 10 to about 30, about 15 to about 25, or about 20 to about 25 nucleotides. In some embodiments, the sense RNA is at least or about 70%, 75%, 80%, 85%, 90%, 95%, 98%, 99%, or 100% complementary to the target RNA. In some embodiments, the target RNA comprises inverted exons of APP.

In some embodiments, a sense RNA inhibits the one or more non-classical variant(s) of APP gene, wherein the one or more non-classical variant(s) comprises inverted exons of the APP gene. In some embodiments, the sense RNA inhibits pre-mRNA. In some embodiments, the sense RNA inhibits mRNA. In some embodiments, the sense RNA alters various functions of the target RNA. In some embodiments, the sense RNA alters splicing of the RNA to yield one or more mRNA species. In some embodiments, the sense RNA alters translation of protein from RNA. In some embodiments, the sense RNA alters translocation of the RNA to the site of protein translation. In some embodiments, the sense RNA alters a catalytic activity of the RNA or which is facilitated by the RNA. Alternatively or in combination, the sense RNA reduces an amount of pre-mRNA.

In some embodiments, the agent is an antisense oligonucleotide (AON). In some embodiments, the AON comprises antisense oligonucleotide strands. In some embodiments, the AON comprises sense oligonucleotide strands. In some embodiments, the AON comprises antisense oligonucleotide strands and sense oligonucleotide strands. In some embodiments, the AON restores a reading frame and allow for production of functional APP. In some embodiments, the AON targets RNA of the one or more non-classical variant(s) of APP gene. In some embodiments, the RNA is pre-mRNA. In some embodiments, the RNA is mRNA. In some embodiments, the AON targets DNA of the one or more non-classical variant(s) of APP gene. In some embodiments, the DNA is genomic DNA. In some embodiments, the DNA is nuclear DNA. In some embodiments, the DNA is extrachromosomal or extranuclear DNA. In some embodiments, the DNA is circular DNA.

Antisense oligonucleotides (AONs), in some embodiments, inhibit the expression of one or more non-classical variant(s) of APP gene. In some embodiments, the AONs inhibit the activity of the one or more non-classical variant(s) of APP gene. In some embodiments, the AONs inhibit the expression or activity of the one or more non-classical variant(s) of APP gene by targeting RNA of the one or more non-classical variant(s) of APP gene for degradation.

In some embodiments, antisense oligonucleotides (AONs) inhibit a gene of a protein involved in transcription of APP. An exemplary protein is a transcription factor, coactivator, corepressor, chromatin modifying enzyme, histone acetyltransferase, histone deacetylase, kinase, or methylase, or any other protein involved in a signal transduction pathway that results in transcription of APP. In some embodiments, the AONs inhibit the gene of a protein involved in transcription of APP to inhibit generation of of the one or more non-classical variants of APP.

In some embodiments, the antisense oligonucleotide (AON) results in an insertion, deletion, duplication, or alteration in an incorrectly processed transcript of the APP gene. In some embodiments, the incorrectly processed transcript of the APP gene is one or more non-classical variant(s) of the APP gene. In some embodiments, the one or more non-classical variant(s) comprise a portion or all of an exon of APP. In some embodiments, the one or more non-classical variant(s) comprise a portion or all of exon 1, 2, 3, 4, 5, 6, 7, 8, 9, 10, 11, 12, 13, 14, 15, 16, 17, 18, or combinations thereof of APP. In some embodiments, the one or more non-classical variant(s) of APP does not comprise exon 8. In some embodiments, the AON induces exon skipping or exon inclusion to restore the translational reading frame of the one or more non-classical variant(s) of APP.

In some embodiments, the antisense oligonucleotide (AON) induces exon skipping. In some embodiments, the AON is a short nucleic acid sequence that binds to specific mRNA or pre-mRNA sequences of the APP gene to induce exon skipping. In some embodiments, the AON is a short nucleic acid sequence that binds to specific DNA sequences of the APP gene to induce exon skipping. In some embodiments, the AON binds splice sites or exonic enhancers. In some embodiments, binding of the AON to specific mRNA or pre-mRNA sequences generates double-stranded regions. In some embodiments, formation of double-stranded regions occurs at sites where the spliceosome or proteins associated with the spliceosome would normally bind and causes exons to be skipped. In some embodiments, skipping of exons results in restoration of the transcript reading frame and allows for production of functional APP.

In some embodiments, the antisense oligonucleotide (AON) induces exon inclusion. In some embodiments, the AON binds to at least one of a splice site, a site near a splice site, and a site distant to a splice site. In some embodiments, the AON binds at site in the RNA to prevent disruption of an exon splice enhancer or intron splice enhancer. In some embodiments, the AON binds at site in the RNA to prevent creation of an exon splice silencer or intron splice silencer.

In some embodiments, the antisense oligonucleotide (AON) comprises natural, synthetic, or artificial nucleotide analogues or bases. In some embodiments, the AON comprises DNA, RNA, or nucleotide analogues. In some embodiments, the synthetic or artificial nucleotide analogues or bases comprise modifications at one or more of ribose moiety, phosphate moiety, nucleoside moiety, or a combination thereof.

In some embodiments, the antisense oligonucleotide (AON) comprises a nucleobase that is unmodified such as adenine, guanine, cytosine, thymine, and uracil or any synthetic or modified nucleobase. Examples of modified nucleobases include, without limitation, hypoxanthine, xanthine, 7-methylguanine, 5,6-dihydrouracil, 5-methylcytosine, and 5-hydroxymethoylcytosine.

In some embodiments, the antisense oligonucleotide (AON) comprises a backbone that connects components of the AON. In some embodiments, the backbone comprises a 3'-5' phosphodiester linkage connecting sugar moieties of the AON. Examples of a backbone structure or linkages of the AON, include, but are not limited to, phosphorothioate, phosphorodithioate, phosphoroselenoate, phosphorodiselenoate, phosphoroanilothioate, phosphoraniladate, and phosphoramidate. In some embodiments, the backbone structure of the AON does not comprise phosphorous but comprises peptide bonds, for example in a peptide nucleic acid (PNA), or linking groups including carbamate, amides, and linear and cyclic hydrocarbon groups. In some embodiments, the backbone modification is a phosphorothioate linkage. In some embodiments, the backbone modification is a phosphoramidate linkage.

In some embodiments, the antisense oligonucleotide (AON) comprises an unmodified sugar moiety such as ribose or deoxyribose or a modified sugar moiety or sugar analog, including a morpholino ring. Non-limiting examples of modified sugar moieties include 2' substitutions such as 2'-O-methyl (2'-O-Me), 2'-O-methoxyethyl (2'MOE), 2'-O-aminoethyl, 2'F; N3'→P5' phosphoramidate, 2'dimethylaminooxyethoxy, 2'dimethylaminoethoxyethoxy, 2'-guanidinidium, 2'-O-guanidinium ethyl, carbamate modified sugars, and bicyclic modified sugars. In some embodiments, the sugar moiety modification is an extra bridge bond, such as in a locked nucleic acid (LNA). In some embodiments the sugar analog contains a morpholino ring, such as phosphorodiamidate morpholino (PMO). In some embodiments, the sugar moiety comprises a ribofuransyl or 2'deoxyribofuransyl modification. In some embodiments, the sugar moiety comprises 2'4'-constrained 2'O-methyloxyethyl (cMOE) modifications. In some embodiments, the sugar moiety comprises cEt 2', 4' constrained 2'-O ethyl BNA modifications. In some embodiments, the sugar moiety comprises tricycloDNA (tcDNA) modifications. In some embodiments, the sugar moiety comprises ethylene nucleic acid (ENA) modifications. In some embodiments, the sugar moiety comprises MCE modifications.

In some embodiments, the antisense oligonucleotide (AON) comprises an artificial nucleotide analogue. Exemplary artificial nucleotide analogues include 2'-O-methyl, 2'-O-methoxyethyl (2'-O-MOE), 2'-O-aminopropyl, 2'-deoxy, T-deoxy-2'-fluoro, 2'-O-aminopropyl (2'-0-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof. In some embodiments, the modified nucleotide analogue is a constrained ethyl (cEt) nucleotide.

In some embodiments, the antisense oligonucleotide (AON) comprises a number of nucleobases. In some embodiments, the number of nucleobases comprises a range of about 8 to 50, 8 to 40, 8 to 35, 8 to 30, 8 to 25, 8 to 20, 8 to 15, 9 to 50, 9 to 40, 9 to 35, 9 to 30, 9 to 25, 9 to 20, 9 to 15, 10 to 50, 10 to 40, 10 to 35, 10 to 30, 10 to 25, 10 to 20, 10 to 15, 11 to 50, 11 to 40, 11 to 35, 11 to 30, 11 to 25, 11 to 20, 11 to 15, 12 to 50, 12 to 40, 12 to 35, 12 to 30, 12 to 25, 12 to 20, 12 to 15, 13 to 50, 13 to 40, 13 to 35, 13 to 30, 13 to 25, 13 to 20, 14 to 50, 14 to 40, 14 to 35, 14 to 30, 14 to 25, 14 to 20, 15 to 50, 15 to 40, 15 to 35, 15 to 30, 15 to 25, 15 to 20, 20 to 50, 20 to 40, 20 to 35, 20 to 30, 20 to 25, 25 to 50, 25 to 40, 25 to 35, or 25 to 30 nucleobases.

In some embodiments, the sequence of the antisense oligonucleotide (AON) is at least or about 40%, 50%, 55%, 60%, 65%, 70%, 75%, 80%, 85%, 90%, 95%, 98%, 99%, or 99.5% complementary to a target sequence. In some embodiments, the target sequence is a sequence of the one or more non-classical variant(s) of APP gene. In some embodiments, the target sequence is a RNA sequence. In some embodiments, the target sequence is a sequence as set forth in SEQ ID NO: 1, 2, 3, 4, 5, 6, 7, 8, 9, 10, 11, 12, 13, 14, 15, or 16. In some embodiments, the target sequence is a DNA sequence.

In some embodiments, the agent inhibits transcription of APP. In some embodiments, the agent inhibits transcription of APP and subsequent incorporation of one or more non-classical variants of APP into the genome. In some embodiments, the agent inhibits a protein in a signal transduction pathway involved in the transcription of APP. In some embodiments, the protein is extracellular. Exemplary extracellular proteins include cell membrane receptors including, but not limited to, G protein-coupled receptors, integrin receptors, Notch receptors, cadherin receptors, receptor tyrosine kinase receptors, chemokine receptors, cytokine receptors, death receptors, T-cell receptors, and any combination thereof. In some embodiments, the agent targets a signaling molecule that signals through the extracellular proteins. Exemplary signaling molecules include, but are not limited to, hormones, neurotransmitters, cytokines, growth factors, cell adhesion molecules, and vitamins. In some embodiments, the agent targets a signaling molecule of an extracellular protein receptor to prevent binding of the signaling molecule and the extracellular protein to subsequently inhibit transcription of APP. In some embodiments, the agent mimics a signaling molecule of an extracellular protein receptor to inhibit signaling and subsequent transcription of APP.

In some embodiments, the agent inhibits transcription of APP by inhibiting an intracellular protein involved in transcription of APP. In some embodiments, the protein is cytosolic. In some embodiments, the protein is nuclear. In some embodiments, the protein modulates transcription of APP. In some embodiments, the protein is a transcription factor, coactivator, corepressor, chromatin modifying enzyme, histone acetyltransferase, histone deacetylase, kinase, or methylase that modulates transcription of APP.

Exemplary signal transduction pathways involved in transcription of APP include, but are not limited to, Wnt signal transduction pathway, 5' adenosine monophosphate-activated protein kinase (AMPK), mechanistic target of rapamycin (mTOR) complexes, the Sirtuin 1 (silent mating-type information regulator 2 homolog 1)/peroxisome proliferator-activated receptor gamma co-activator 1-α (Sirt1/PGC-1α) axis, and cholinergic receptor signaling.

In some embodiments, the agent edits a nucleic acid of one or more non-classical variant(s) of APP. In some embodiments, the agent edits DNA. In some embodiments, the agent edits RNA. An exemplary system for nucleic acid editing comprises Clustered Regularly Interspaced Short Palindromic Repeats (CRISPR) and a CRISPR-associated (Cas) protein. When expressed or transferred into cells alongside a guide RNA (gRNA), a Cas protein allows for the targeted introduction or deletion of genetic information via a complex with CRISPR sequence of mRNA. Generally, the gRNA comprises a target sequence region, a protospacer-adjacent motif (PAM) region, and a hairpin region. In a CRISPR/Cas process, a gRNA shepherds the Cas enzyme to a specific stretch of nucleic acid. In some embodiments, the gRNA is a single stranded guide RNA (sgRNA). In some embodiments, the gRNA is a dual stranded guide RNA (dgRNA). Cas then cleaves the nucleic acid to disable or repair a gene. In some embodiments, the nucleic acid is DNA. In some embodiments, the nucleic acid is RNA.

Provided herein, in certain embodiments, are methods for targeting a nucleic acid of one or more non-classical variants of APP using a CRISPR/Cas system. In some embodiments, the CRISPR/Cas system targets DNA of the one or more non-classical variant(s) of APP. In some embodiments, CRISPR/Cas system targets RNA of the one or more non-classical variant(s) of APP. In some embodiments, the one or more non-classical variant(s) comprise a portion or all of an exon of APP. In some embodiments, the one or more non-classical variant(s) comprise a portion or all of exon 1, 2, 3, 4, 5, 6, 7, 8, 9, 10, 11, 12, 13, 14, 15, 16, 17, 18, or combinations thereof of APP. In some embodiments, the one or more non-classical variant(s) of APP comprise a portion or all of exon 1, 2, 3, 4, 5, 6, 7, 9, 10, 11, 12, 13, 14, 15, 16, 17, 18, or combinations thereof. In some embodiments, the one or more non-classical variant(s) of APP does not comprise exon 8. In some embodiments, the one or more non-classical variant(s) of APP comprise a single nucleotide variation (SNV) in the APP gene. In some embodiments, the non-classical variant of APP comprises one or more SNVs in the APP gene. In some embodiments, the SNV is in the amyloid beta region of APP. In some embodiments, the SNV in APP, which translate to amino acid positions in APP include, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translate to amino acid positions in APP include, but are not limited to, A673, A713, T714, V715, I716, V717, T719, and L723, wherein the amino acids correspond to positions 673, 713, 714, 715, 716, 717, 719, and 723 of SEQ ID NO: 17. In some embodiments, the SNV in APP, which translate to amino acid positions in APP include, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translate to amino acid positions in APP include, but are not limited to, A673V, A713T, T714I, V715M, V715A, I716M, V717I, V717F, T719P, and L723P.

In some embodiments, a nuclease for use in the CRISPR/Cas system is from a species of, but not limited to, *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium,* Corynebacter, *Carnobacterium, Rhodobacter, Listeria, Paludibacter, Clostridium,* Lachnospiraceae, Clostridiaridium, *Leptotrichia, Francisella, Legionella, Alicyclobacillus, Methanomethyophilus, Porphyromonas, Prevotella,* Bacteroidetes, *Helcococcus,* Letospira, *Desulfovibrio, Desulfonatronum, Desulfurococcus,* Opitutaceae, *Tuberibacillus, Bacillus, Brevibacillus, Methylobacterium, Natronobacterium, Flavobacterium, Saccharomyces, Chlamydomonas, Thermus, Pyrococcus, Mycoplasma,* or *Acidaminococcus.*

Exemplary Cas proteins include, but are not limited to, Cpf1, C2c1, C2c2, Cas1, Cas1B, Cas2, Cas3, Cas4, Cas5, Cas6, Cas7, Cas8, Cas9 (Csn1 or Csx12), Cas10, Cas13, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, and modified versions thereof. In some embodiments, the Cas protein targets DNA. In some embodiments, the Cas protein targets RNA. In some embodiments, the Cas protein is Cas9. In some embodiments, the Cas protein is Cas13. Cas proteins include, but are not limited to, wild-type Cas and derivatives, chimeras, or mutants thereof.

In some embodiments, the agent modulates generation of one or more non-classical variant(s) of APP as a result of strand breaks. In some embodiments, the agent modulates generation of one or more non-classical variant(s) of APP as a result of single stranded breaks. In some embodiments, the agent modulates generation of one or more non-classical variant(s) of APP as a result of double stranded breaks (DSBs). In some embodiments, the agent inhibits formation of DSBs. In some embodiments, the agent inhibits formation of DSBs by inhibiting the cause of DSBs including, but not limited to, V (D) J recombination, class switch recombination, meiosis, ionizing radiation, oxidative free radicals, replication across a nick, and inadvertent enzyme actions.

DSBs, in some embodiments, are repaired by a DNA repair pathway. In some embodiments, alteration in a DNA repair pathway results in an inability or reduced ability to repair DSBs. In some embodiments, agents for treating a disease or disorder characterized by unwanted accumulation of amyloid beta protein modulate a DNA repair pathway. Exemplary DNA repair pathways include, but are not limited to, non-homologous end joining (NHEJ), microhomology-mediated end joining (MMEJ), homologous recombination, mismatch repair, nucleotide excision repair, or DNA strand cross-link repair. In some embodiments, agents for treating a disease or disorder characterized by unwanted accumulation of amyloid beta protein modulate a DNA DSB repair activity.

In some embodiments, the agent targets a gene involved in a DNA repair pathway. Exemplary genes involved in the DNA repair pathway include, but are not limited to, ATM, ATR, MRN, RAD51, BRCA1/BRCA2, KU70/80, DNA- PKcs, Artemis, Ligase IV, and XRCC4. In some embodiments, the agent targets a protein involved in the DNA repair pathway. Exemplary proteins involved in the DNA repair pathway include, but are not limited to, ATM, ATR, CHK1, RAD51, RAD54, PARP1, ERCC1, DNA-PKcs, and Ligase IV.

In some embodiments, the agent inhibits a protein involved in a DNA repair pathway, wherein the DNA repair pathway is non-homologous end joining (NHEJ). In some embodiments, the protein is involved in a step of NHEJ. For example, the protein is involved in DNA termini recognition, bridging of the DNA ends, DNA end processing, or DNA recognition. Exemplary proteins involved in NHEJ include, but are not limited to, DNA-PKcs, KU70/80, Artemis, Ligase IV/XRCC4, Pol μ, or Pol λ. In some embodiments, the agent is an inhibitor of a protein involved in NHEJ. Exemplary inhibitors of DNA-PKcs include, but are not limited to, wortmannin, LY294002, NU7026, NU7441, KU-0060648, MSC2490484A, CC-122, and CC-115. Exemplary inhibitors of Ligase IV include, but are not limited to, L189 and SCR7.

In some embodiments, the agent inhibits a protein involved in a DNA repair pathway, wherein the DNA repair pathway is homologous recombination. In some embodiments, the agent inhibits CHK1, MRE1, RAD51, or RAD54. In some embodiments, the inhibitor of CHK1 is UCN-01. In some embodiments, the inhibitor of MRE11 is mirin. In some embodiments, the inhibitor of RAD51 is RI-1 or RI-2. In some embodiments, the inhibitor of RAD54 is streptonigrin.

In some embodiments, the agent inhibits a protein involved in one or more DNA repair pathways. For example, the inhibitor inhibits a protein involved in homologous recombination and non-homologous end joining (NHEJ). Exemplary proteins involved in homologous recombination and NHEJ include, but are not limited to, ATM and ATR. In some embodiments, the inhibitor of ATM is KU55933. In some embodiments, the inhibitor of ATR is caffeine, VE-821, or NU6027.

In some embodiments, the agent inhibits a protein involved in a DNA repair pathway, wherein the DNA repair pathway comprises repair of single stranded breaks. In some embodiments, the agent inhibits PARP1. Exemplary PARP1 inhibitors include, but are not limited to, Olaparib (AZD2281), Iniparib (BSI 201), Rucaparib (AG014699), Velparib (ABT-888), Talazoparib (BMN-673), CEP 9722, MK 4827, BMN-673, NU1025, E7016, BGB-290, and 3-aminobenzamide.

Methods for Screening

Described herein, in certain embodiments, are methods for screening for therapeutic agents for treating a disease or disorder in an individual characterized by unwanted accumulation of amyloid beta protein. Further provided herein, in certain embodiments, are in vitro methods for screening for a therapeutic agent for treating a disease or disorder characterized by unwanted accumulation of amyloid beta protein, comprising: contacting a cell that expresses a non-classical variant of an amyloid precursor protein (APP) gene with a test agent; detecting inhibition of expression of the non-classical variant of the APP gene compared to a control; and identifying the test agent as a therapeutic agent if the test agent inhibits expression of the non-classical variant of the APP gene compared to the control. Further provided herein, in certain embodiments, are in vitro methods of screening for a therapeutic agent for treating a disease or disorder characterized by unwanted accumulation of amyloid beta protein, comprising: contacting a cell that expresses a non-classical variant of an APP gene with a test agent; detecting inhibition of the activity of the non-classical variant of the APP gene as compared to a control; and identifying the test agent as the therapeutic agent if the test agents inhibits activity of the non-classical variant of an APP gene as compared to the control. Further provided herein, in certain embodiments, are in vitro methods of screening for a therapeutic agent for treating a disease or disorder characterized by unwanted accumulation of amyloid beta protein, comprising: contacting a cell that expresses a non-classical variant of an APP gene with a test agent; detecting binding of the test agent to the non-classical variant of the APP gene; and identifying the test agent as the therapeutic agent if the test agents binds to the non-classical variant of the APP gene.

In some embodiments, the therapeutic agents are screened using various methods known in the art. For example, the one or more non-classical variant(s) of APP are expressed (e.g., by transfection or transduction) in a cell or organism, contacted with the therapeutic agents, and assayed for changes in activity. In some embodiments, the cell is a neuron. In some embodiments, the therapeutic agents are assayed for binding, specificity, stability, or downstream activity.

In some embodiments, the therapeutic agents are screened for inhibition of expression of the non-classical variant of APP gene. In some embodiments, expression of the non-classical variant of APP is measured by qPCR or gel electrophoresis. In some embodiments, inhibition of protein expression of a protein encoded by the non-classical variant of the APP gene is measured. Exemplary methods for measuring protein expression include, but are not limited to, Western blot, enzyme-linked immunosorbent assays (ELISA), or chromatography. Example of chromatography methods, include but are not limited to, high-performance liquid chromatography (HPLC) or liquid chromatography-mass spectrometry (LC/MS).

In some embodiments, the therapeutic agents are screened for inhibition of activity of the non-classical variant of APP. For example, the activity of the non-classical variant comprises accumulation of amyloid beta protein. In some embodiments, the accumulation of amyloid beta protein is measured by a method comprising Western blot, enzyme-linked immunosorbent assays (ELISA), or chromatography. In some embodiments, the therapeutic agents are screened using an enzymatic activity assay or reporter protein activity assay. For example, the one or more non-classical variant(s) are engineered to express a reporter gene. Exemplary reporter genes include, but are not limited to, acetohydroxyacid synthase (AHAS), alkaline phosphatase (AP), beta galactosidase (LacZ), beta glucuronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), luciferase, and derivatives thereof. Methods to determine modulation of a reporter gene are well known in the art, and include, but are not limited to, fluorometric methods (e.g. fluorescence spectroscopy, Fluorescence Activated Cell Sorting (FACS), fluorescence microscopy), and antibiotic resistance determination.

In some embodiments, therapeutic agents are screened for reducing activity or expression of one or more non-classical variant(s) of APP or protein thereof. In some embodiments, the therapeutic agents are identified as therapeutic agents if activity is reduced by at least or about 10%, 20%, 30%, 40%, 50%, 60%, 70%, 80%, 90%, or more than 90%. In some embodiments, the therapeutic agents are identified as therapeutic agents if expression is reduced by at least or about 10%, 20%, 30%, 40%, 50%, 60%, 70%, 80%, 90%, or more than 90%. In some embodiments, the therapeutic agents are identified as therapeutic agents if accumulation of amyloid beta protein is by at least or about 10%, 20%, 30%, 40%, 50%, 60%, 70%, 80%, 90%, or more than 90%.

Therapeutic agents, in some embodiments, are identified by binding assays. Exemplary binding assays, include but are not limited to, radioactive binding assays, fluorescence resonance energy transfer, surface plasmon resonance, enzyme-linked immunosorbent assays (ELISA), kinetic exclusion assays, and crystallography assays.

In certain embodiments, following identification of therapeutic agents, the therapeutic agents are used for treating an individual in need thereof. Described herein, in certain embodiments, are methods of treating a disease or disorder characterized by unwanted accumulation of amyloid beta protein in an individual in need thereof, comprising: administering to the individual an agent that inhibits activity of one or more non-classical variant(s) of an APP gene. In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) comprises a portion or all of exon 1, 2, 3, 4, 5, 6, 7, 9, 10, 11, 12, 13, 14, 15, 16, 17, 18, or combinations thereof. In some embodiments, the one or more non-classical variant(s) of APP does not comprise exon 8. In some embodiments, the one or more exon(s) in the one or more non-classical variant(s) of APP is rearranged as compared to a control. In some embodiments, the one or more non-classical variant(s) of APP comprises a sequence as set forth in SEQ ID NO: 1, 2, 3, 4, 5, 6, 7, 8, 9, 10, 11, 12, 13, 14, 15, or 16. In some embodiments, the disease or disorder is Alzheimer's disease. In some embodiments, the Alzheimer's disease is familial Alzheimer's disease (FAD) or sporadic Alzheimer's disease. In some embodiments, the agent that inhibits the activity of APP is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. In some embodiments, the antibody binds to a protein encoded by the one or more non-classical variant(s) of APP. In some embodiments, the protein is encoded by the one or more non-classical variant(s) of APP comprising a sequence as set forth in SEQ ID NO: 1, 2, 3, 4, 5, 6, 7, 8, 9, 10, 11, 12, 13, 14, 15, or 16.

Kits

Described herein are kits for identifying one or more non-classical variant(s) of amyloid precursor protein (APP) gene. In some embodiments, kits are provided for detecting a portion or all of exon 1, 2, 3, 4, 5, 6, 7, 8, 9, 10, 11, 12, 13, 14, 15, 16, 17, 18, or combinations thereof. In some embodiments, kits are provided for detecting a portion or all of exon 1, 2, 3, 4, 5, 6, 7, 9, 10, 11, 12, 13, 14, 15, 16, 17, 18, or combinations thereof. In some embodiments, kits are provided for detecting intraexonic junction between exon 1 and exon 11, exon 1 and exon 14, exon 2 and exon 17, exon 2 and exon 14, exon 2 and exon 18, exon 2 and exon 16, exon 3 and exon 16, exon 3 and exon 14, exon 3 and exon 17, exon 6 and exon 17, exon 6 and exon 18, exon 3 and exon 9, exon 2 and exon 9, exon 16 and exon 18, exon 6 and exon 12, exon 5 and exon 16, or exon 16 and exon 17. In some embodiments, kits are provided for detecting the one or more non-classical variant(s) of APP that comprise a sequence as set forth in SEQ ID NO: 1, 2, 3, 4, 5, 6, 7, 8, 9, 10, 11, 12, 13, 14, 15, or 16.

In some embodiments, kits comprise nucleic acid or polypeptide isolation reagents. In some embodiments, kits comprise one or more probe(s) for hybridization or amplification of a target nucleic acid whose expression profile or activity profile is associated with Alzheimer's disease. In some embodiments, kits include one or more probe(s) for control genes, such as housekeeping genes. In some embodiments, the one or more probe(s) for control genes are used, for example, in $\Delta C_t$ calculations. In some embodiments, a probe of the one or more probe(s) is labeled with an enzyme, a radioactive isotope, or a fluorescent label. In some embodiments, the probe is labeled using an affinity tag. Exemplary affinity tags include, but are not limited to, biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione. In some embodiments, the kit comprises a detecting reagent that binds to the one or more probe(s). In some embodiments, the detecting reagent comprises a radioactive isotope or a fluorescent label In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

In some embodiments, kits comprise one or more additional containers, each with one or more of various materials (such as reagents, optionally in concentrated form, and/or devices) desirable from a commercial and user standpoint for use of described herein. Non-limiting examples of such materials include, but are not limited to, buffers, primers, enzymes, diluents, filters, carrier, package, container, vial and/or tube labels listing contents and/or instructions for use and package inserts with instructions for use. A set of instructions is optionally included. In some embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In some embodiments, a label is used to indicate that the contents are to be used for a specific therapeutic application. In some embodiments, a label also indicates directions for use of the contents, such as in the methods described herein.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Identification of Non-Classical Variants

Non-classical variants were identified from neurons isolated from non-diseased brains and Alzheimer's disease brains.

Fluorescence Activated Cell Sorting of Neurons

Neuronal nuclei were isolated from postmortem frontal cortices (CTX) and cerebellums (CBL) of non-diseased (Non-AD) and Alzheimer's disease (AD) brains and prepared for fluorescence activated cell sorting (FACS). Isolated nuclei were fixed and labeled with rabbit anti-NeuN antibody (1:800) (Millipore, Germany) and Alexa Fluor 488 donkey anti-rabbit IgG secondary (1:500) (Life Technologies, Carlsbad, CA), and counterstained with propidium iodide, PI (50 µg/ml) (Sigma, St. Louis, MO). Electronically gated diploid neuronal nuclei, determined by PI fluorescence and immunolabeling, were analyzed and sorted.

RNA Extraction

Following FACS, RNA was extracted from populations of 50 NeuN positive nuclei. Extracted RNA were reverse-transcribed with (CTAGTTCTGCATCTGCT-CAAAGAACTTG) (SEQ ID NO: 18) and amyloid precursor protein (APP) cDNA was amplified by polymerase-chain reactions (PCR) using a forward primer (ATGCTGCCCGGTTTGGCA) (SEQ ID NO: 19) and a reverse primer (CTAGTTCTGCATCTGCT-CAAAGAACTTG) (SEQ ID NO: 20).

Figure 2:
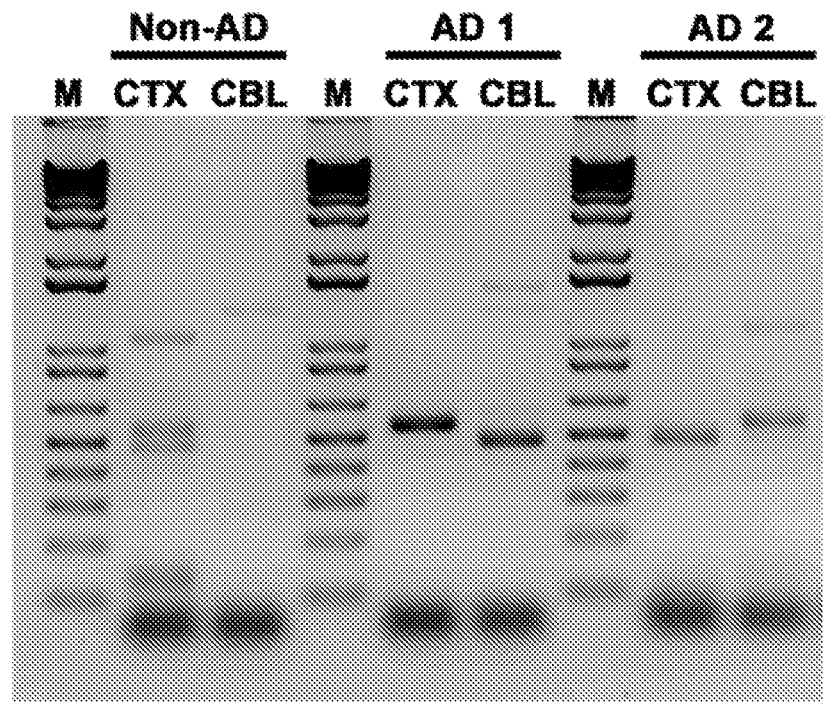
FIG. 2 illustrates a gel electrophoresis of RT-PCR from neurons isolated from cortices (CTX) and cerebellums (CBL) from non-diseased (Non-AD) postmortem brains and Alzheimer's disease (AD) brains. M represents DNA ladder marker.
Figure 3:
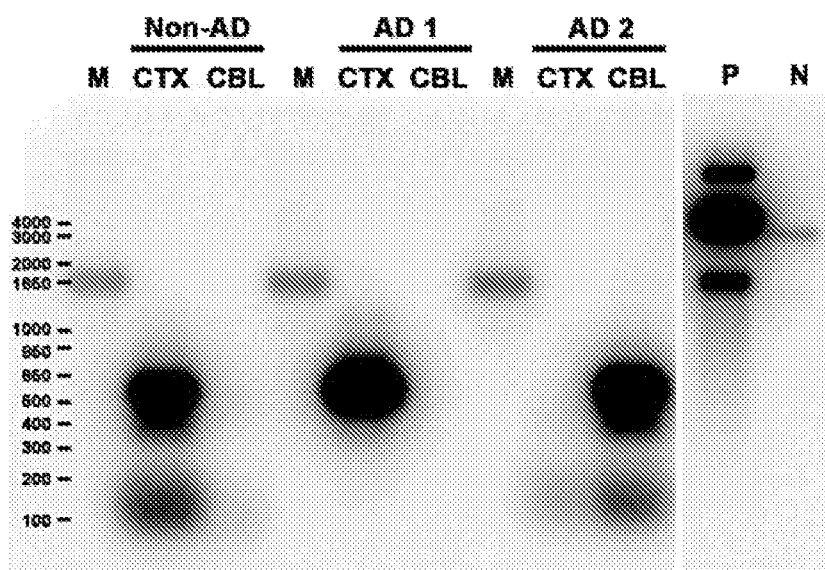
FIG. 3 illustrates a Southern blot of RT-PCR from neurons isolated from cortices (CTX) and cerebellums (CBL) from non-diseased (Non-AD) postmortem brains and Alzheimer's disease (AD) brains hybridized with APP cDNA probe. P and N represent positive (APP plasmid) and negative (Presenilin 1 plasmid) control, respectively.

Half of the PCR products were run and separated on agarose gels with a DNA ladder (M) (FIG. 2). Gels were transferred to nylon membranes and then blotted with $P^{32}$-labelled APP cDNA probe (SEQ ID NO. 21) as seen in Table 3. Radioactivity on the membranes was detected by Typhoon phosphorimager (FIG. 3).

TABLE 3

| SEQ ID NO | Name | Sequence |
| --- | --- | --- |
| 21 | APP cDNA Probe | ACTGCTCCTGCTGGCCGCCTGGACGGCTCGGGCGCTG GAGGTACCCACTGATGGTAATGCTGGCCTGCTGGCTG AACCCCAGATTGCCATGTTCTGTGGCAGACTGAACAT GCACATGAATGTCCAGAATGGGAAGTGGGATTCAGAT CCATCAGGGACCAAAACCTGCATTGATACCAAGGAAG GCATCCTGCAGTATTGCCAAGAAGTCTACCCTGAACT GCAGATCACCAATGTGGTAGAAGCCAACCAACCAGTG ACCATCCAGAACTGGTGCAAGCGGGGCCGCAAGCAGT GCAAGACCCATCCC |

Figure 4:
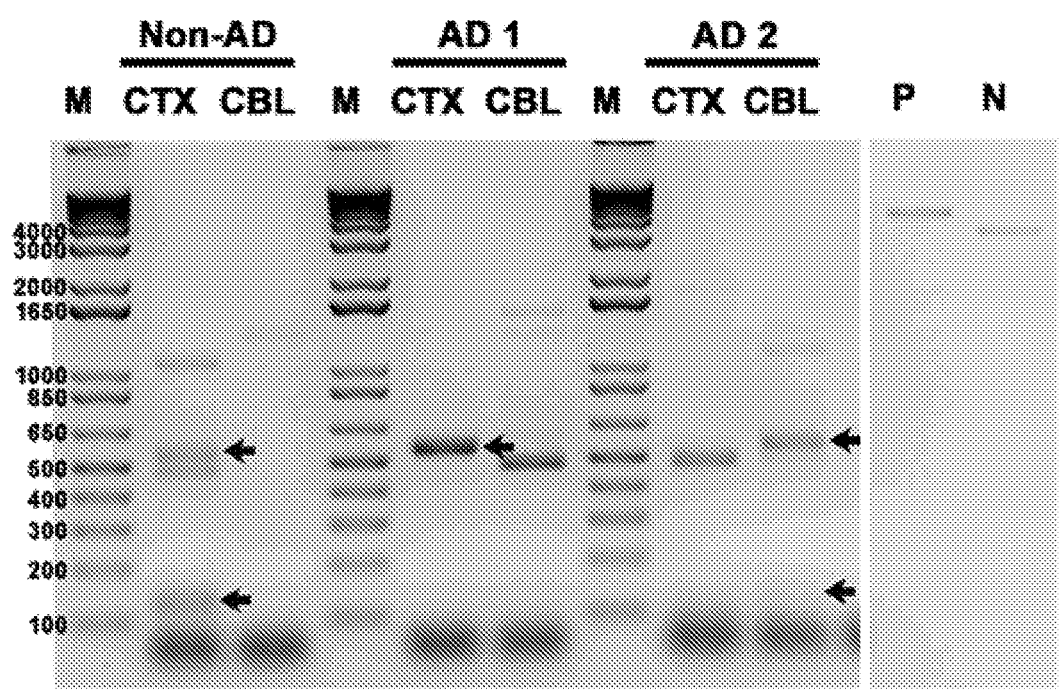
FIG. 4 illustrates a gel electrophoresis of RT-PCR from neurons isolated from cortices (CTX) and cerebellums (CBL) from non-diseased (Non-AD) postmortem brains and Alzheimer's disease (AD) brains. Arrows indicate positive signals corresponding to signal from Southern blot.
Figure 5:
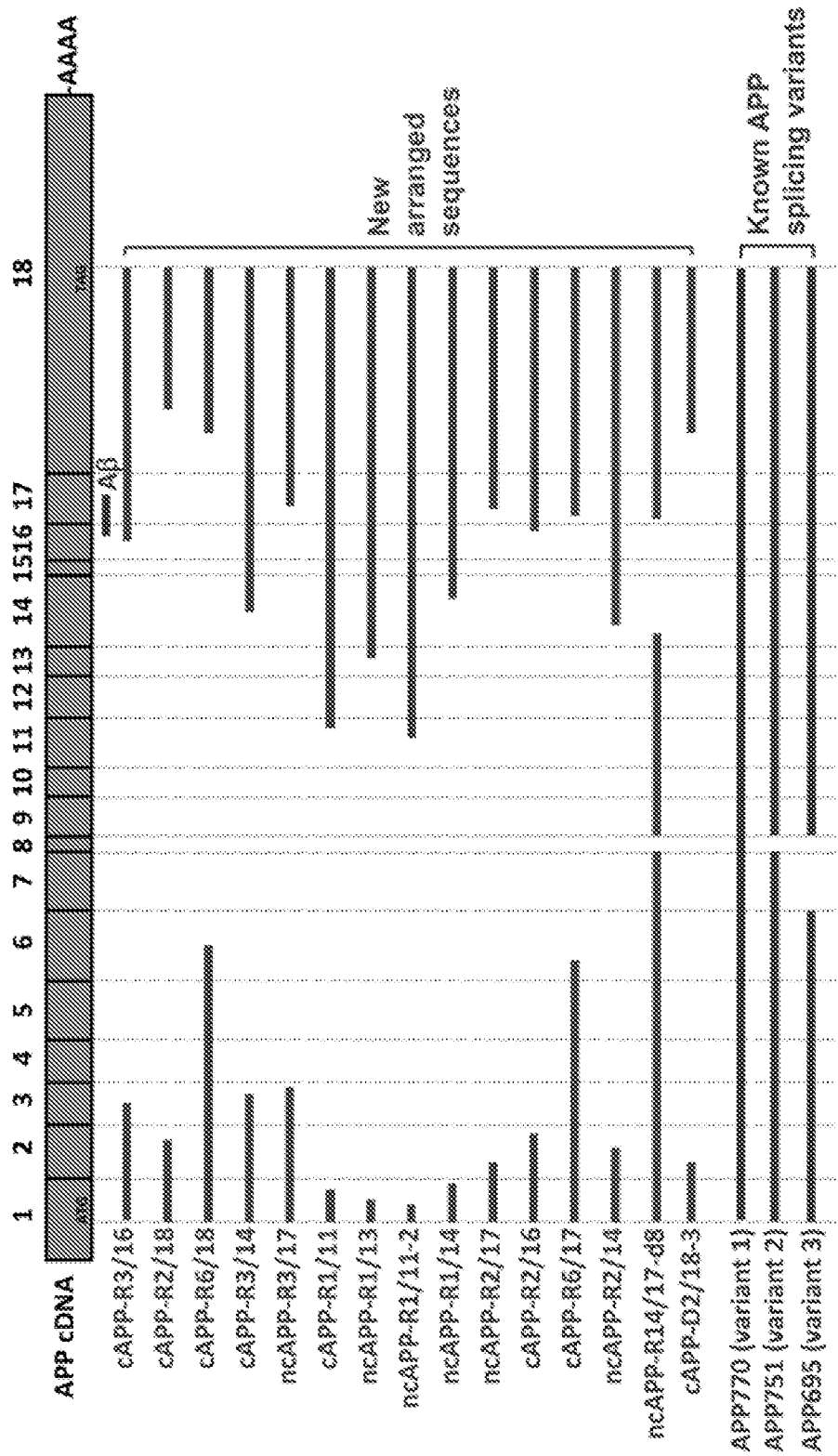
FIG. 5 illustrates exemplary non-classical variants.

The remaining PCR products were run on another agarose gel, and the bands corresponding to the positive signals (indicated by arrows) on nylon membranes were excised (FIG. 4). Excised PCR products were cloned and sequenced for variant analysis. Following sequencing, non-classical variants as seen FIG. 5 were identified.

Example 2. cDNA Library

A cDNA library was prepared from populations of 50-nuclei from non-diseased (Non-AD) and Alzheimer's disease (AD) brains with lambda phage library system (Clonetech Laboratories).

Percentages of non-classical variants cAPP-R3/16, ncAPP-R2/17, ncAPP-R1/13, and cAPP-R1/11 were determined in Non-AD and AD nuclei as seen in Table 4.

TABLE 4

| Non-classical Variant | Non-AD | AD |
| --- | --- | --- |
| cAPP-R3/16 | 25% | 89.4% |
| ncAPP-R2/17 | 75% | 0% |
| ncAPP-R1/13 | 0% | 5.3% |
| cAPP-R1/11 | 0% | 5.3% |

Figure 6A:
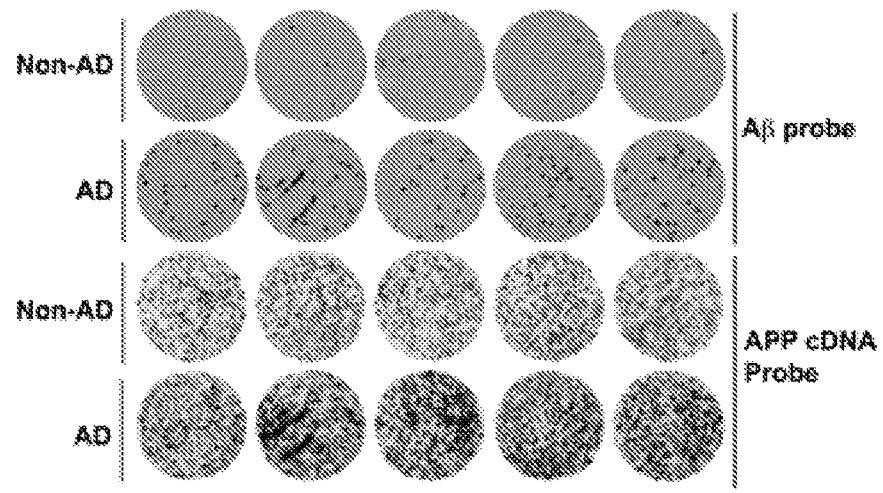
FIG. 6A illustrates amyloid beta positive clones from non-diseased (Non-AD) brains and Alzheimer's disease (AD) brains detected with amyloid beta (Aβ) probes and APP cDNA probes.
Figure 6B:
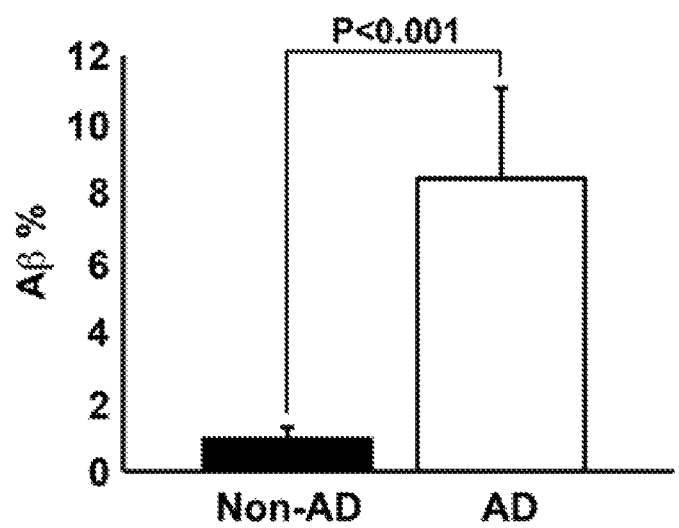
FIG. 6B illustrates a graph of percentage of amyloid beta in non-diseased (Non-AD) brains and Alzheimer's disease (AD) brains.

Percentages of amyloid beta positive phage clones from Non-AD and AD brains were also determined using probes for amyloid beta (GATGCAGAATTCCGA-CATGACTCAGGATATGAAGTTCATCATCAAAAAT-TGGTG TTCTTTGCAGAAGATGTGGGTT-CAAACAAAGGTGCAATCATTGGACTCATGGTGG GCGGTGTTGTCATAGCG) (SEQ ID NO: 22) and APP cDNA (FIG. 6A). A significant increase in percentage of amyloid beta was seen in AD brains than non-AD brains (FIG. 6B).

Figure 7:
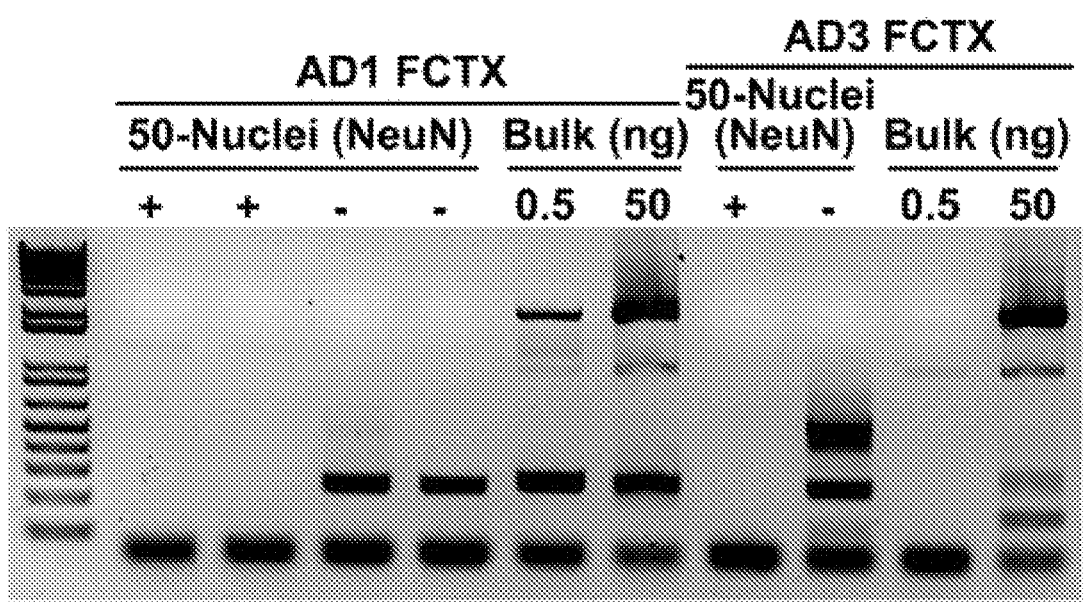
FIG. 7 illustrates a gel electrophoresis of RT-PCR from frontal cortices of Alzheimer's disease (AD) brains (AD1 and AD3) in sorted neuronal and non-neuronal nuclei and bulk RNA.

Comparing APP mRNA in sorted nuclei or bulk RNA, FIG. 7 shows that full-length APP mRNA is mainly in the cytoplasm.

Example 3. Non-Classical Variants Detected in Genomic DNA

Neuronal nuclei were sorted from human postmortem frontal cortices from non-diseased and Alzheimer's disease brains. Genomic DNA was extracted and purified using DNeasy Blood and Tissue Kit (Qiagen, Valencia, CA). Purified genomic DNA was used as a template for PCR amplification using primers for APP comprising a forward primer (ATGCTGCCCGGTTTGGCA) (SEQ ID NO: 23) and a reverse primer (CTAGTTCTGCATCTGCT-CAAAGAACTTG) (SEQ ID NO: 24). PCR products amplified with APP primers were run on an agarose gel (FIG. 8A) as well as a no template control (NTC). In addition to APP, PSEN1 primers were used to amplify the purified genomic DNA and were run on an agarose gel with a positive control (PC) and a no template control (NTC) (FIG. 8B). PCR products were cloned and sequenced for variant identification.

Figure 8A:
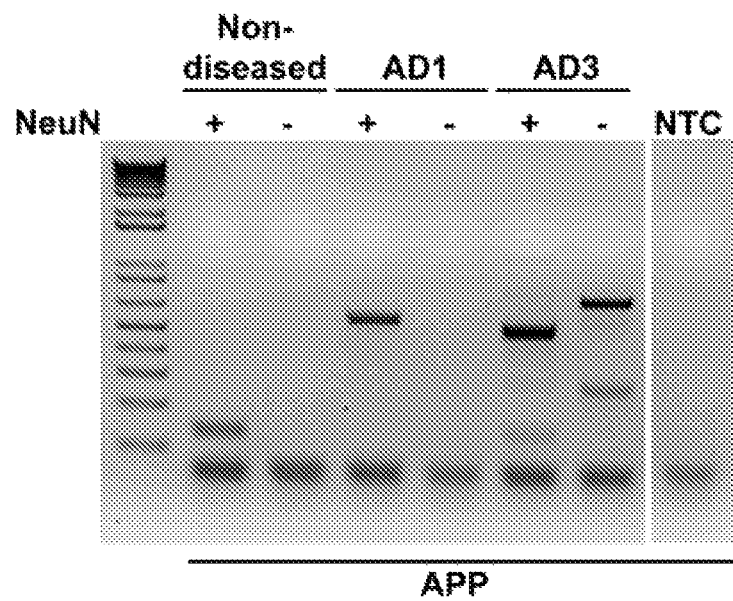
FIG. 8A illustrates a gel electrophoresis of PCR for genomic DNA isolated from frontal cortices of non-diseased brains and Alzheimer's disease (AD) brains (AD1 and AD3) with APP primers. NTC represents no template control.
Figure 8B:
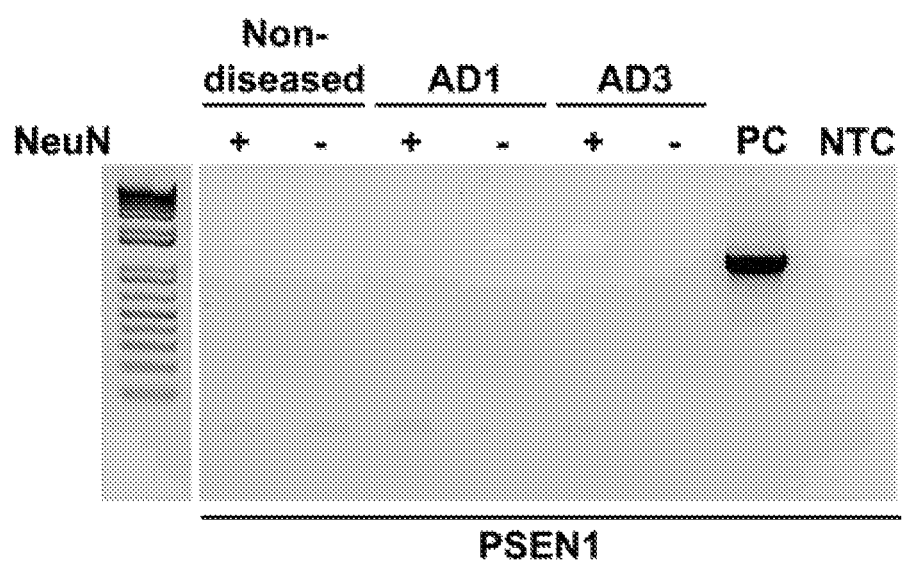
FIG. 8B illustrates a gel electrophoresis of PCR for genomic DNA isolated from frontal cortices of non-diseased brains and Alzheimer's disease (AD) brains (AD1 and AD3) with Presenilin 1 (PSEN1) primers. NTC represents no template control, and PC represents positive control.

Referring to FIG. 8A, non-classical variants of APP were identified in neuronal and non-neuronal gDNA. Using primers for PSEN1, non-classical variants were not identified on gDNA (FIG. 8B).

Example 4. Quantitative Polymerase Chain Reaction of Non-Classical Variant cAPP-R3/16 on DNA Populations of 20-nuclei were isolated as in Example 1 and analyzed by quantitative polymerase chain reaction (qPCR) to detect non-classical variant cAPP-R3/16.

Genomic DNA from sorted nuclei was extracted by QuickExtract DNA extraction solution (Epicentre) and pre-amplified by TaqMan PreAmp Master Mix (Thermo Fisher Scientific). Standard qPCR reactions using TaqMan probe based assays were performed in triplicate. Reactions were run on a BioRad qPCR thermocycler using TaqMan Real-Time PCR Master Mix (Thermo Fisher Scientific). The crossing threshold (Ct) was determined for primers for cAPP-R3/16, PSEN1 and TERT within the linear region of the amplification curve.

Figure 9:
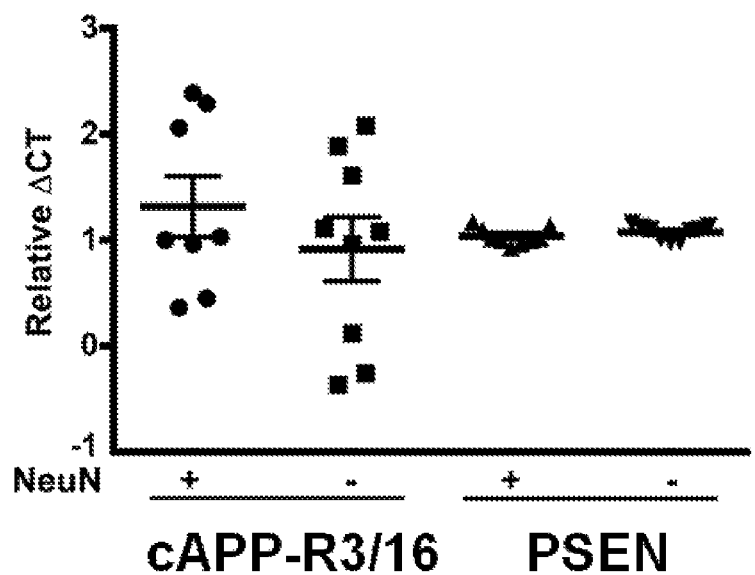
FIG. 9 illustrates a graph of relative ΔCT for neuronal and non-neuronal samples in which cAPP-R3/16 and PSEN are detected.
Figure 10:
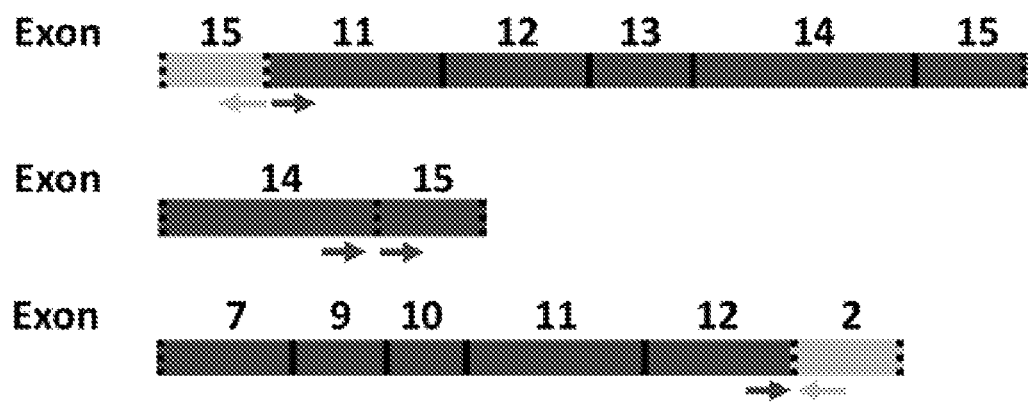
FIG. 10 illustrates a schema for detection of non-classical variants by DNA pull-down assay.

Referring to FIG. 9, the non-classical variant cAPP-R3/16 was quantitatively detected in neuronal and non-neuronal cells with a wide range of distribution whereas as PSEN1 was with a consistent distribution.

Example 5. Pull-Down Assay of Non-Classical Variants

Non-classical variants were detected using a DNA pull-down assay. The in vitro transcribed RNA probe sequence used for DNA pull-down was APP cDNA sequence. The pull-down sequences were cloned and sequenced for APP variant analysis.

Example 6. DNA In Situ Hybridization of Neuronal Cells

Neuronal nuclei were isolated from frontal cortices of AD brains as described in Example 1 and analyzed for intron/exon and exon/exon sequences of APP.

gDNA in nuclei were hybridized with intron/exon and exon/exon probes and labeled with different colors by chromogenic method. Briefly, neuronal nuclei from AD brains were fixed and sorted for NeuN positivity, and dried onto slides. Neuronal nuclei were treated with RNase cocktail (Ambion) for 1 hour at 40° C., following by hydrogen peroxide treatment for 10 minutes at room temperature and protease treatment for 10 minutes at 40° C. DNA denaturation was performed by incubating the slides with 0.58× SSC, 70% formamide, and 0.1% SDS for 20 minutes at 80° C. DNA in situ hybridization probes were incubated with samples at 40° C. overnight.

Chromogenic developing procedures were performed according to manufacturer's protocol (Advanced Cell Diagnostics). Slides were then visualized by microscopy.

Figure 11:
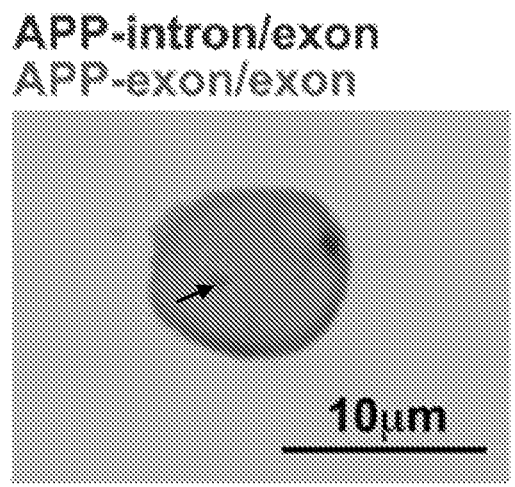
FIG. 11 illustrates genomic rearrangements in an Alzheimer's disease (AD) neuronal nuclei detected by DNA in situ hybridization.

As seen in FIG. 11, genomic rearrangements were observed. Specifically, exon-exon junctions as seen in the arrow were present.

Example 7. RNA In Situ Hybridization of Tissue

Brain samples from patients with AD were isolated and sectioned, and non-classical variants were analyzed.

Non-classical variants were analyzed using RNA in situ hybridization. 10 µm human AD frontal cortices were sectioned and fixed by neutral buffered formalin. Fixed tissue sections were treated with hydrogen peroxide for 10 minutes at room temperature, followed by target retrieval and protease treatment. RNA in situ hybridization probes were incubated with samples for 2 hours at 40° C. Chromogenic developing procedures were performed according to manufacturer's protocol. After RNA in situ hybridization, anti-Aβ monoclonal antibody (MOAB, Millipore) was incubated with sample at room temperature overnight. Horseradish peroxidase based developing method was used for signal detection. Slides were then visualized by microscopy at 200× and 630× magnification.

Figure 12:
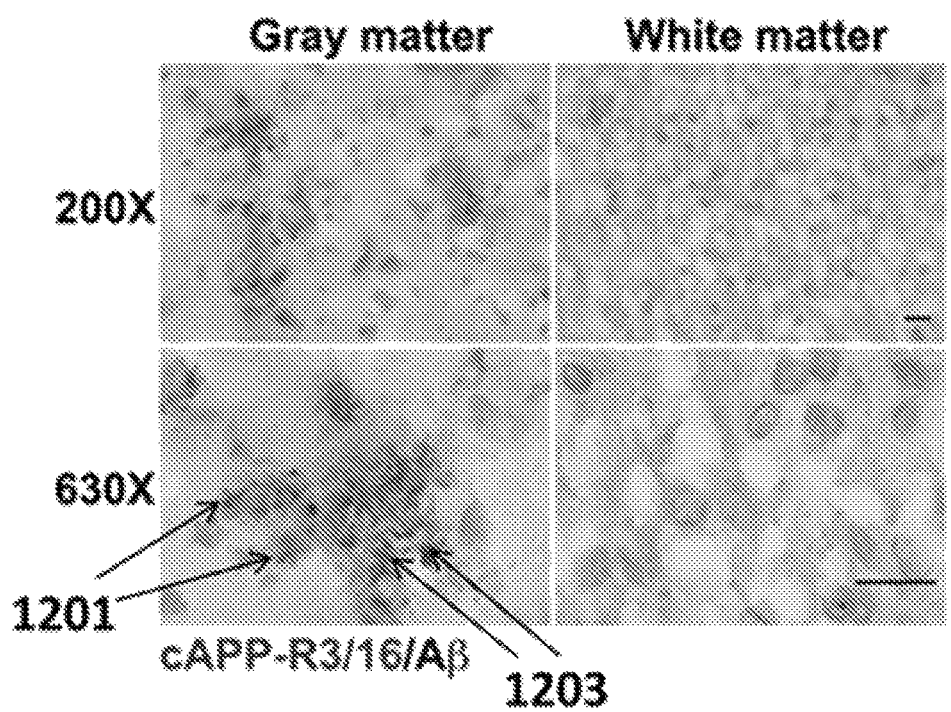
FIG. 12 illustrates intraexonic rearrangements in tissue sections from an Alzheimer's disease (AD) brain detected by RNA in situ hybridization of non-classical variant cAPP-R3/16 (1201). Amyloid beta (Aβ) is indicated (1203). Tissue sections are visualized at 200× and 630× magnification.

As seen in FIG. 12, intraexonic rearrangement junctions were observed. Specifically, the non-classical variant cAPP-R3/16 (red, 1201) was detected near amyloid beta plaques (brown, 1203).

Example 8. Single Molecule Real-Time Sequencing of Non-Classical Variants

Non-classical variants were detected by single molecule real-time (SMRT) sequencing.

RNA Samples were prepared from 2 AD temporal lobes. Methods for preparation of RNA for sequencing were provided according to manufacturer's instructions (Pacific Biosciences). Briefly, target cDNA was prepared and captured by xGene lockdown probes. cDNA of interest was then ligated to adaptors and ready for SMRT sequencing with RSII sequencer.

Figure 13:
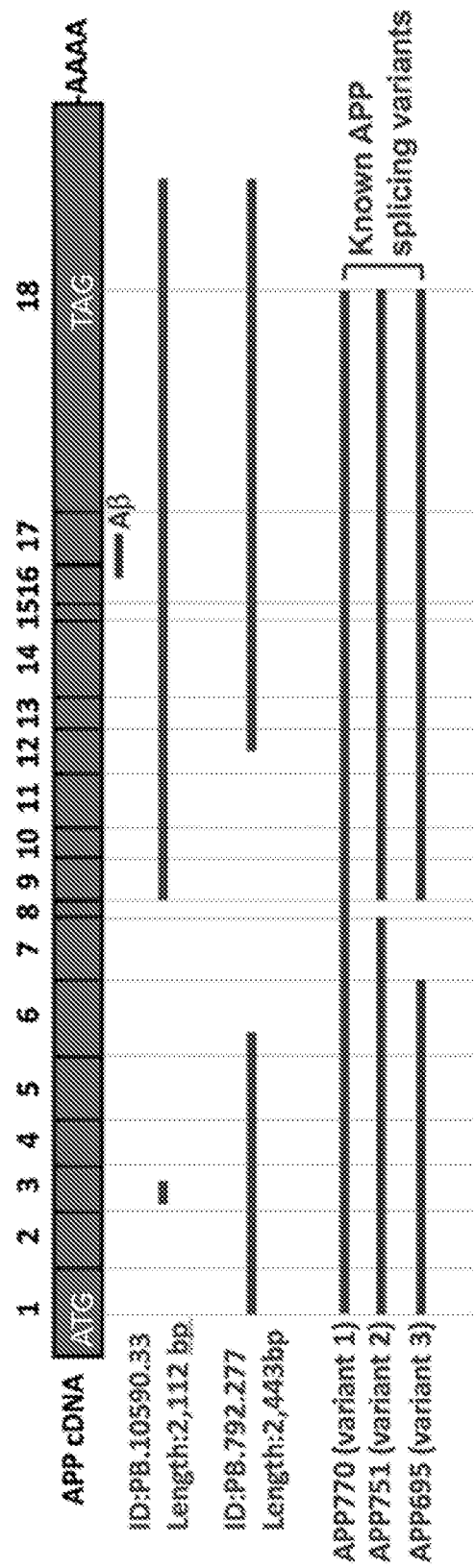
FIG. 13 illustrates non-classical variants detected by single molecule real-time sequencing.

Following cDNA sequencing, non-classical variants were identified (FIG. 13).

Example 9. DNA In Situ Hybridization of Nuclei from AD and Non-Diseased Brains

Non-neuronal and neuronal nuclei were isolated from non-diseased and AD brains as described in Example 1 and analyzed for exon-exon junctions and intraexonic rearrangements of APP. Non-classical variants were analyzed using DNA in situ hybridization. Briefly, nuclei dried on to slides were treated with RNase cocktail for 1 hour at 40° C., followed by hydrogen peroxidase treatment, target retrieval, protease treatment, and DNA denaturation. DNA in situ hybridization probes were incubated with samples at 40° C. overnight. Chromogenic developing procedures were performed according to manufacturer's protocol. Probes used here were designed to detect exon 16 and exon 17.

Figure 14:
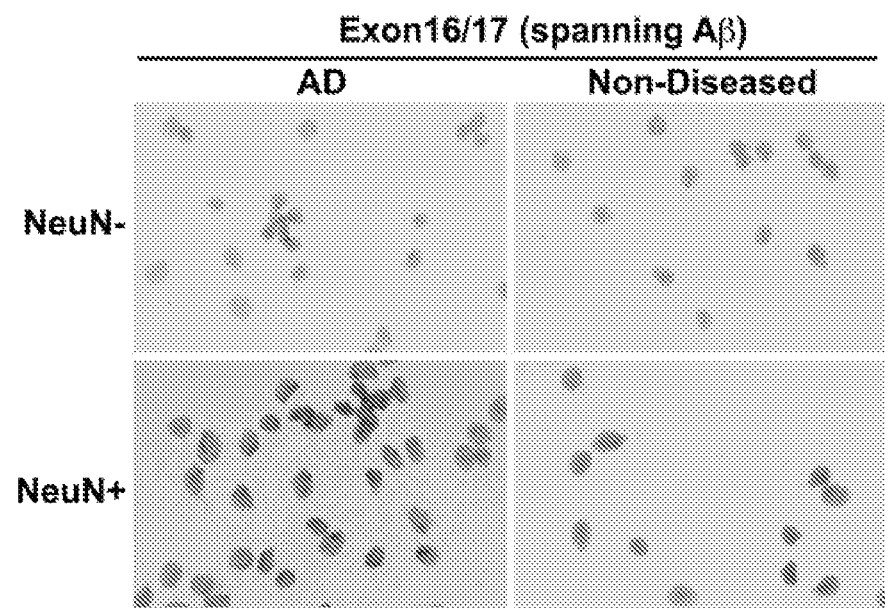
FIG. 14 illustrates the presence of exon 16 and exon 17 junction in neuronal and non-neuronal nuclei from non-diseased and Alzheimer's disease (AD) brains detected by DNA in situ hybridization.

Nuclei from neuronal and non-neuronal cells showed an increased signal in AD brains as compared to non-diseased brains (FIG. 14).

Example 10. Non-Classical Variants Expressed Protein

Non-classical variants were analyzed for ability to express protein.

Figure 15A:
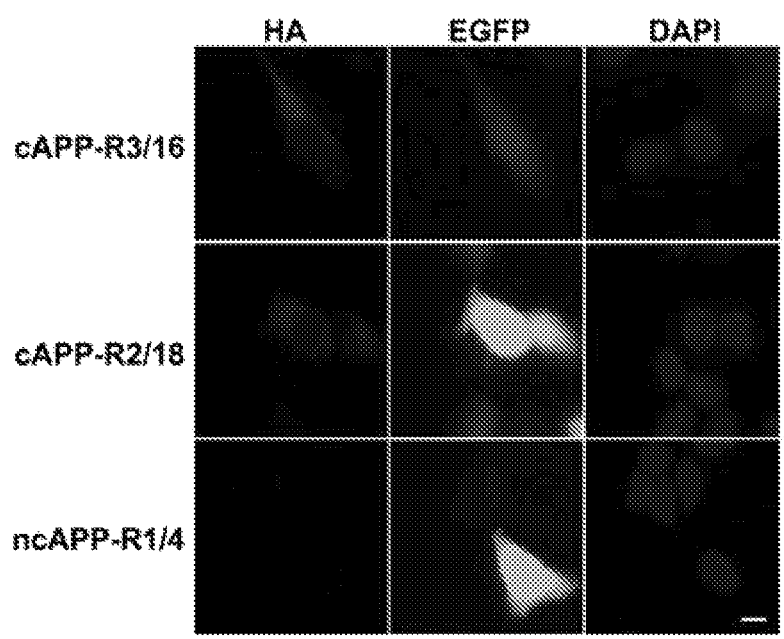
FIG. 15A illustrates immunofluorescence images of cells transfected with non-classical variants cAPP-R3/16, cAPP-R2/18, and ncAPP-R1/4 that are hemagglutinin (HA) epitope tagged (left panel). EGFP co-expression (middle panel) and DAPI staining (right panel) are shown.
Figure 15B:
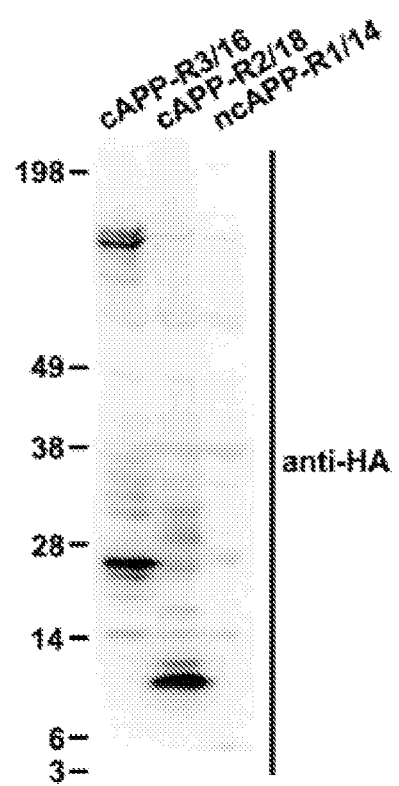
FIG. 15B illustrates a Western blot of cell lysate from cells transfected with non-classical variants cAPP-R3/16, cAPP-R2/18, and ncAPP-R1/4 that are hemagglutinin (HA) epitope tagged. The Western blot was probed with HA antibody.

Non-classical variants cAPP-R3/16, cAPP-R2/16, and ncAPP-R1/4 were epitope tagged with hemagglutinin (HA). The non-classical variants were transfected and expressed in cells. Referring to FIG. 15A, nuclei were stained with DAPI (right panel). The epitope tagged non-classical variants also heterologously expressed EGFP (center panel). Non-classical variants comprising coding regions expressed HA-tagged protein (left panel). Western blot for HA showed similar results in that non-classical variants comprising coding regions expressed HA-tagged protein (FIG. 15B).

Example 11. Non-Classical Variants Detected in Cells Expressing APP cDNA

Figure 16A:
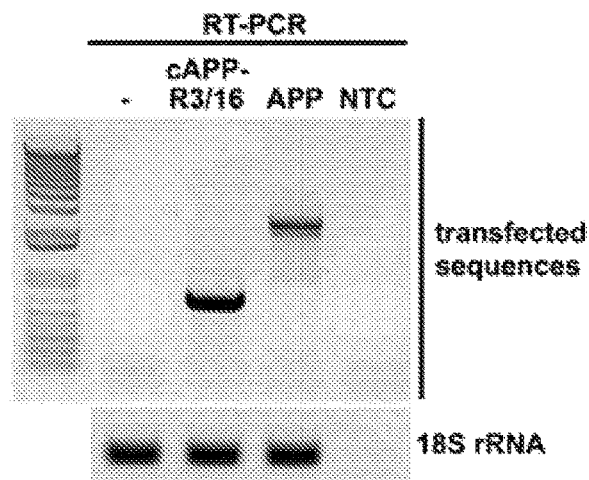
FIG. 16A illustrates a gel electrophoresis of RT-PCR of LN-229 cells transfected with non-classical variant cAPP-R3/16 or wild-type APP (APP).

LN-229 cells were transfected with vehicle, non-classical variant cAPP-R3/16, or wild-type APP cDNA (APP). RNA was extracted from the LN-229 cells and subject to reverse transcription PCR (RT-PCR). RT-PCR products were run on a gel. The non-classical variant cAPP-R3/16 and APP were detected (FIG. 16A).

Figure 16B:
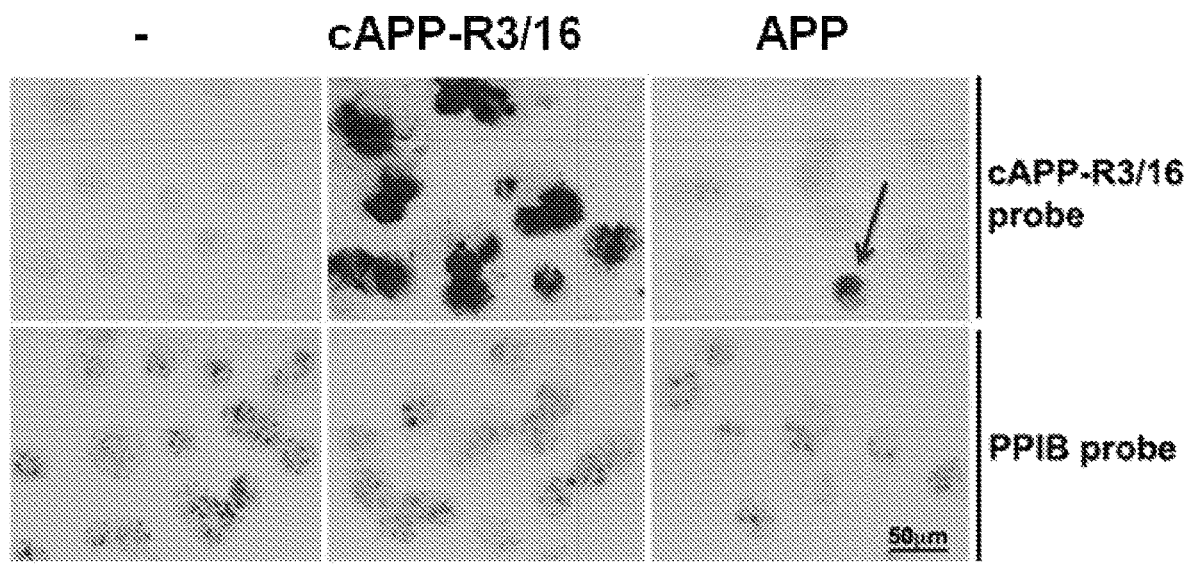
FIG. 16B illustrates cAPP-R3/16 induction in LN-229 cells transfected with CAPP-R3/16 or wild-type APP (APP) detected by DNA in situ hybridization using cAPP-R3/16 probe and PPIB probe as a positive control.

LN-229 cells were also transfected with vehicle, non-classical variant cAPP-R3/16, or APP for analysis by RNA in situ hybridization. Cells were fixed in neutral buffered formalin for 10 min at room temperature. Fixed cells were treated with hydrogen peroxide, following by target retrieval and protease treatment. RNA in situ hybridization probes were incubated with samples for 2 hours at 40° C. Chromogenic developing procedures were performed according to manufacturer's protocol. Probes used for staining were cAPP-R3/16 and PPIB as a positive control. The non-classical variant cAPP-R3/16 was detected in cells expressing non-classical variant cAPP-R3/16 as well as in cells expressing wild-type APP (FIG. 16B).

Example 12. Methods for Analysis of Non-Classical Variants of APP

Nuclei Extraction and Fluorescence-Activated Nuclear Sorting (FANS)

For in situ, hybridization analyses, isolated nuclei were fixed in 1:10 diluted buffered formalin (Fisher Healthcare) for 5 minutes. Fixed or unfixed nuclei were then labeled with anti-NeuN rabbit monoclonal antibody (1:800) (Millipore, Germany) and Alexa Fluor 488 donkey anti-rabbit IgG (1:500) (Life Technology, Carlsbad, CA), and counterstained with propidium iodide (PI) (50µ/ml) (Sigma, St. Louis, MO). Diploid NeuN positive and negative nuclei were gated by PI and immunofluorescence, and sorted into appropriate populations for RT-PCR or genomic DNA PCR and in situ hybridization. FANS was performed by FACS-Aria with a FACS-Aria II.

RNA Extraction and RT-PCR

RNA extraction from 50-nuclei populations and bulk tissues were performed using Quick-RNA MicroPrep (Zymo Research, Irvine, CA) and RNAeasy Mini kits (Qiagen, Valencia, CA), respectively, according to manufacturer's protocol. OneStep Ahead RT-PCR (Qiagen, Valencia, CA) was used for RT-PCR with APP sense primer 5'-ATGCTGCCCGGTTTGGCA-3' (SEQ ID NO: 25) and APP anti-sense primer 5'-CTAGTTCTGCATCTGCT-CAAAGAACTTG-3' (SEQ ID NO: 26). Low annealing stringency PCR was carried out with the following thermal cycling steps: 95° C. 15 seconds, 55° C. 15 seconds, and 68° C. 2.5 minutes.

Southern Blotting

RT-PCR products were run on an agarose gel, denatured, and transferred to a positively charged nylon membrane. UV crosslinked membranes were incubated with denatured and purified $^{32}$P-labelled APP cDNA probes at 42° C. overnight. Blots were washed four times with increasing washing stringency. Images were developed by Typhoon (GE Healthcare Life Sciences) or Fujifilm FLA-5100 phosphorimager.

DNA Extraction and Genomic DNA PCR

DNA extraction from isolated neuronal nuclei populations was performed using DNAeasy and QIAamp DNA Mini kits (Qiagen, Valencia, CA) according to manufacturer's instruction. High annealing stringency PCR for APP was performed by FastStart PCR master (Sigma, St. Louis, MO) with 95° C. 30 seconds, 65° C. 30 seconds, and 72° C. 2.5 minutes, and Platinum SuperFi DNA polymerase (Life Technology) with 98° C. 10 seconds, 65° C. 10 seconds, and 72° C. 1.5 minutes. For PSEN1 PCR, the primer sequences were the following: sense 5'-ATGACAGAGTTACCTGCACC-3' (SEQ ID NO: 27) and anti-sense 5'-CTAGATATAAAATT-GATGGAA-3' (SEQ ID NO: 28). Thermal cycling steps were 95° C. 30 seconds, 52° C. 30 seconds, 72° C. 2 minutes, and 98° C. 10 seconds, 52° C. 10 seconds, 72° C. 1 minute for FastStart PCR master and Platinum SuperFi DNA polymerase, respectively.

Junction-Specific Genomic In Situ Hybridization (jgISH) and RNA-ISH

For jgISH pretreatment, sorted nuclei were dried on Plus Gold slides (Fisher Scientific, Pittsburgh, PA). Nuclei were then treated with RNase cocktail enzyme mix (1:50) (ThermoFisher) at 40° C. for 60 minutes, followed by 1:10 dilution buffered formalin fixation at room temperature for 5 minutes. After two washes with distilled water, slides were treated with hydrogen peroxide at room temperature for 10 minutes, target retrieval reagent at 95° C. for 15 minutes, followed by protease treatment at 40° C. for 10 minutes. Restriction enzyme was applied after protease treatment for 2 hours if needed. DNA was denatured (2×SSC, 70% formamide and 0.1% sodium dodecyl sulfate) at 80° C. for 20 minutes. After cooling down the slides to room temperature, probes were applied and incubated with nuclei at 40° C. overnight. Samples were then developed.

For RNA-ISH pretreatment, 10 µm fresh frozen human tissue sections were fixed by 1:10 dilution buffered formalin on ice for 10 minutes. After two washes with PBS, tissue sections were soaked in serial diluted ethanol (50%, 70% and 100%) for 5 minutes at each step. Slides were then treated with hydrogen peroxide at room temperature for 10 minutes, followed by protease at room temperature for 20 minutes. Probes were incubated with tissue sections at 40° C. for 2 hours. Hydrogen peroxide, 10× target retrieval buffer, proteases, probes (Ex16/17 targeting ACATGACTCAGGATATGAAGTTCATCATCAAAAAT-TGGTGTTCTTTGCA (SEQ ID NO: 29); IEJ 3/16 targeting TGCCAAGAAGTCTACCCTGAACTGCAGATCAC-CAAGATGGATGC (SEQ ID NO: 30, including sense and anti-sense probes) and reagents for signal developing were all purchased from Advanced Cell Diagnosis (ACD, Newark, CA). Nuclei or tissue sections were counterstained with hematoxylin. Zeiss AX10 Imager.M2 microscope and ZEN2 software were used for image acquisition. Images were thresholded, and foci number/size were quantified using ImageJ for statistical analysis.

SMRT Sequencing

Neuronal DNA was used as template for APP PCR by Platinum SuperFi DNA polymerase with high annealing stringency (98° C. 10 seconds, 65° C. 10 seconds, and 72° C. 1.5 minutes). Multiple PCR reactions were pooled and purified by DNA Clean and Concentrator-5 (Zymo Research, Irvine, CA) for SMRT sequencing library preparation. PCR products were repaired using SMRTbell template prep kit version 2.0 (PacBio) and purified using AMPure PB beads (PacBio). Adapters were ligated to DNA to create SMRTbell libraries. Sequencing polymerase was annealed, and the SMRTbell library was loaded using Magbead binding. Raw bam sequencing files were converted to fastq format using the ccs2 algorithm in SMRTLink Version 4.0. Reads were only included in the analyzed fastq file if 1) there were more than 20 passes of the sequencing polymerase over the DNA molecule in the zero mode waveguide well and 2) the read was calculated to possess a >0.9999 predicted accuracy.

Genomic Data Analyses with Customized Bioinformatic Algorithms

Novel algorithms were developed to detect and analyze exon rearrangement in genes of interest. The algorithms were specifically designed to analyze long-read sequences generated by Pacific Biosciences Sequel platform. A series of quality control (QC) procedures were performed prior to sequence processing to ensure high quality of reads being analyzed.

Quality control: Consensus sequence and read quality. PacBio circular consensus sequences (CCS) reads with less than 20 passes were filtered out to ensure overall sequence quality. Quality score and read length distributions are examined: for APP gene PCR enriched sequences, average median read-wide Phred score is 93 and read length ranged from 64 to 2470 nucleotides. Reads for which the median Phred score was >85 were analyzed.

Quality control: Sequencing artifacts. Errors in homopolymers were handled with a method combining quality score information and reference sequence at the beginning of a homopolymer. The CCS FASTQ files encoded uncertainty in the homopolymer run length in the first Phred score of each run. If this Phred score was lower than a threshold of 30, then this position was marked as a likely sequencing artifact and not a real variant.

PCR primer filter. The reads were checked to ensure the correct start and end sites with forward and reverse PCR primer sequences. BLAST (command line tool "blastn" 2.6.0+) was used to align primer sequences in either orientation to each read with word size 13, gap open penalty 0 and gap extension penalty 2. Any read where both primers were not detected was filtered out. Furthermore, reads on the negative strand were reverse complemented in this step. BLAST seed length was optimized to avoid ambiguity and ensure sensitivity.

Alignment to APP reference sequences. Ensembl reference sequence for APP protein was downloaded from the GRCh38 reference human genome assembly using the UCSC Genome Browser with RefSeq accession number NM_000484.3. Since the PCR primers started at the start codon and end with the stop codon, sequences of exons 1 and 18 were trimmed to these positions so only the coding sequence of each of the 18 exons was kept and stored as a FASTA file. BLAST was then used to look for local alignment between 18 exons and each quality-filtered CCS read; blastn parameters used: -outfmt 6, -wordsize 25, -gapopen 0, -gapextend 2. These resulting alignment coordinates were used to mark regions of each read covered by exons for analysis of exon arrangements, lengths and patterns of exon-exon joins.

Construction and retroviral transduction of human APP exon 16/exon 17 concatamers. Phosphorylated oligonucleotides (Integrated DNA Technologies) composed of human APP exon 16 and exon 17 sequences with BamHI and BglII restriction sites on the 5' ends were annealed, and ligated into the BamHI site of the retroviral expression vector S-003-AB LZRSpBMN-linker-IRES-EGFP. Single and concatamerized oligonucleotide inserts were identified by PCR using primers flanking the BamHI insertion site and identified clones were sequenced to confirm insert copy number (GENEWIZ). Helper-free ecotropic virus was produced by transfecting DNA constructs (Lipofecatime 2000, Thermo Fisher Scientific) with single or multiple copies of the oligonucleotide inserts into the retrovirus packaging line Phoenix-ECO. 48 hours post-transfection, retroviral supernatants were harvested and 2 mL of selected virus was used for transduction of NIH-3T3 cells in 6 well plates. Retroviral transduction was carried out by removing the cell growth medium, replacing it with 2 mL of retroviral supernatant containing 4 μg/ml polybrene, and spinning at 25° C. for 1 hour at 2800 r.p.m. 48 hours post-transduction, the percentage of GFP+ cells, as identified by flow cytometry, was used to evaluate the transduction efficiency. The following primers were used to produce the retroviral constructs: 16/17 Bam: 5'-GATCCACATGACTCAGGATATGAAGTTCAT-CATCAAAAATTGGTGTTCTTTGCAA-3', (SEQ ID NO: 31) and 16/17 BglII Rev: 5'-GATCTTGCAAAGAACAC-CAATTTTTGATGATGAACTTCATATCCTGAGT-CATGTG-3' (SEQ ID NO: 32).

Cell Culture

NIH-3T3 cells were purchased from ATCC. Cells were maintained in Dulbecco's modified Eagle's medium (Invitrogen) containing 5% fetal bovine serum (Invitrogen) at 37° C. under 5% CO2.

Example 13. Non-Classical RNA Variants of APP in Populations of Neuronal Nuclei

Non-classical variants were analyzed in transcriptionally amplified RNA from populations of neuronal nuclei.

Figure 17A:
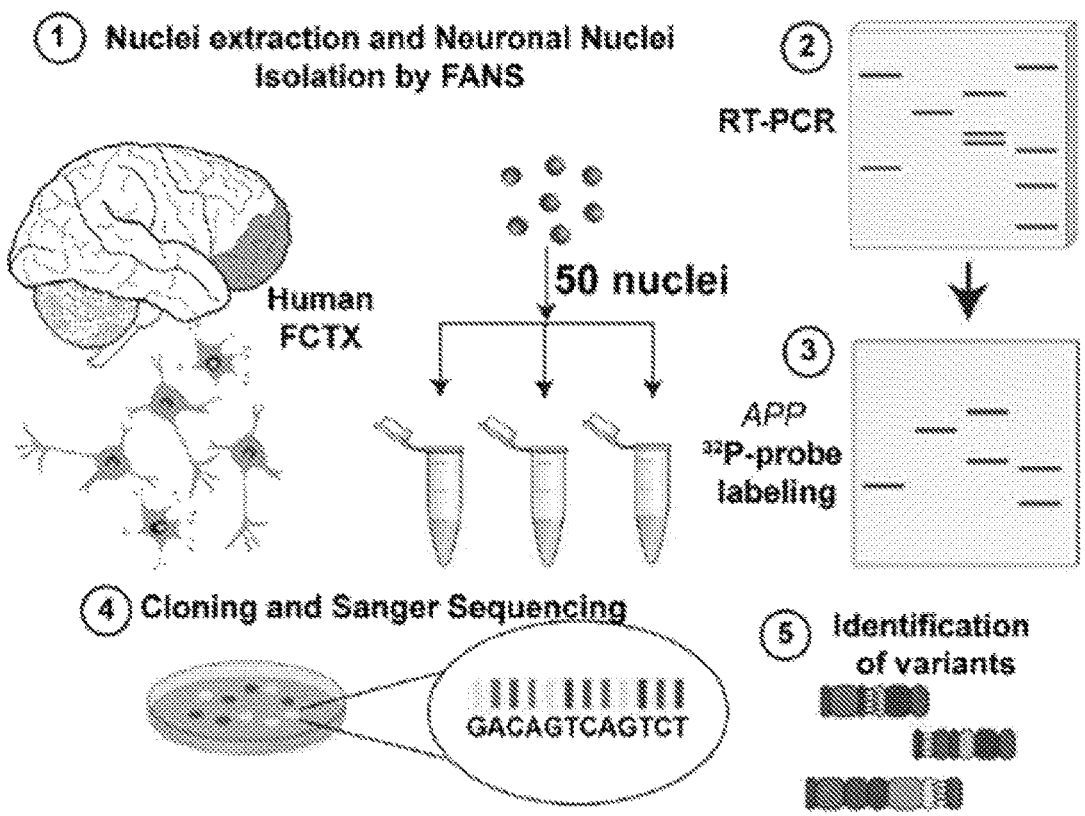
FIG. 17A illustrates a schematic for identification of non-classical RNA variants of APP from populations of neurons. (1) 50-neuronal nuclei were sorted from human prefrontal cortices (FCTX) by fluorescence-activated nuclear sorting (FANS) and used for (2) RT-PCR. Resulting RT-PCR products were screened by (3) Southern blot with $^{32}$P-labeled APP cDNA probes. (4) Bands with positive signals from duplicate gels were cloned and sequenced. (5) Non-classical variants were identified. Figure discloses SEQ ID NO: 33.

Non-classical variant sequences of APP were analyzed by RT-PCR in nuclei isolated by fluorescence activated nuclear sorting (FANS). The workflow (FIG. 17A) commenced with FANS to isolate neurons from both non-diseased and verified SAD prefrontal cerebral cortex (Table 5), which were run in parallel. Groups of 50, NeuN-positive neuronal nuclei were isolated and processed for RT-PCR (FIG. 17A). Validated primers capable of amplifying full-length APP cDNA (APP 770, NM_000484.3) were used, followed by agarose gel electrophoresis.

TABLE 5

Brain Information.

| Brain Name | Braak | Sex | PMI (Hours) | Age (years) |
|---|---|---|---|---|
| SAD-1 | 6 | F | 6 | 88 |
| SAD-2 | 6 | F | 12 | 88 |
| SAD-3 | 6 | F | 6 | 84 |
| SAD-4 | 6 | F | 4 | 86 |
| SAD-5 | 6 | M | 5 | 83 |
| SAD-6 | 6 | F | 10 | 72 |
| ND-1 | 1 | M | U | 87 |
| ND-2 | 1 | F | 72 | 83 |
| ND-3 | U | M | U | 83 |
| ND-4 | 1 | F | 12 | 80 |
| ND-3 | 1 | F | 18 | 93 |
| ND-6 | 2 | M | 12 | 94 |
| ND-7 | U | M | 12 | 69 |
| SAD-7 | 5 | F | 3.7 | 77 |

F = Female,
M = Male,
U = Unknown

Figure 17B:
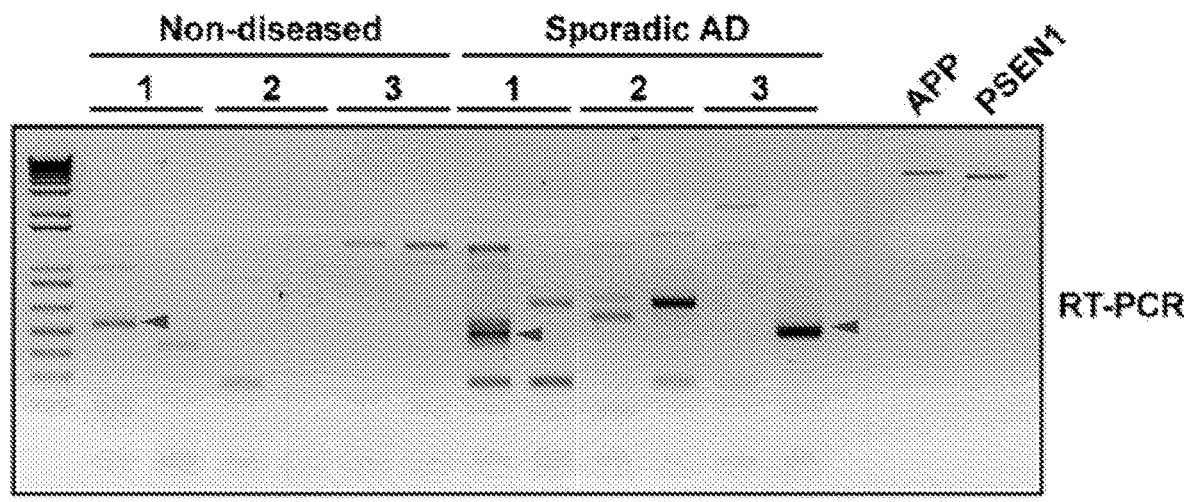
FIG. 17B illustrates electrophoresis of RT-PCR products from 3 non-diseased and 3 sporadic AD brains. APP and PSEN1 plasmids were run as positive and negative controls for Southern blotting, respectively.
Figure 17C:
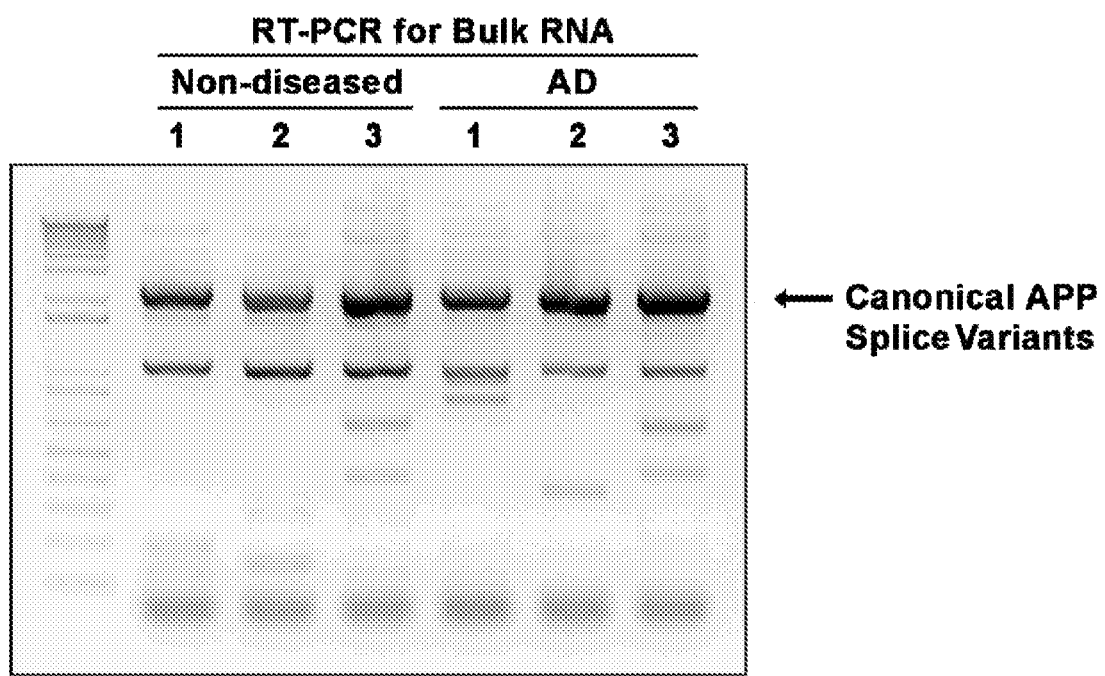
FIG. 17C illustrates a gel electrophoresis of RT-PCR for bulk RNA detecting canonical APP splice variants as major products. Bulk RNA from 3 non-diseased and 3 sporadic Alzheimer's disease (SAD) prefrontal cortices was used for APP RT-PCR. Major products detected were canonical APP splice variants.
Figure 17D:
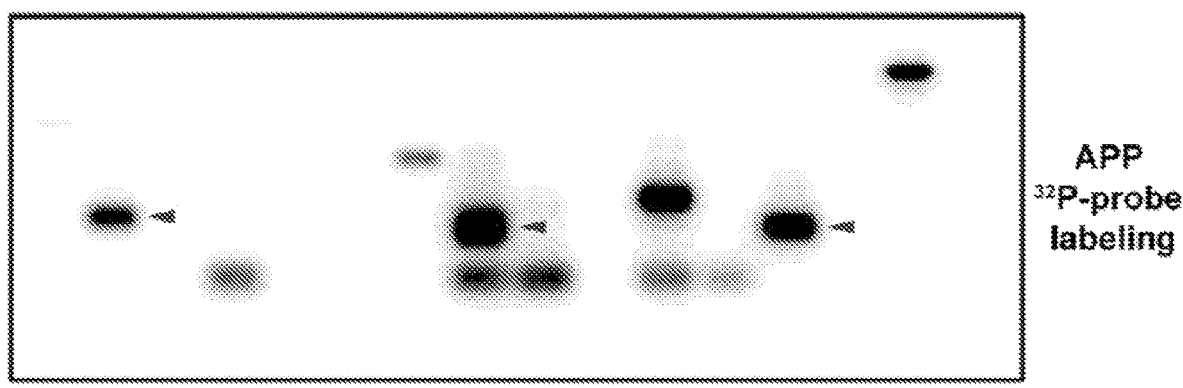
FIG. 17D illustrates Southern blot of RT-PCR products. Arrows indicate examples of corresponding bands from FIG. 17B that were cloned and Sanger sequenced.
Figure 17E:
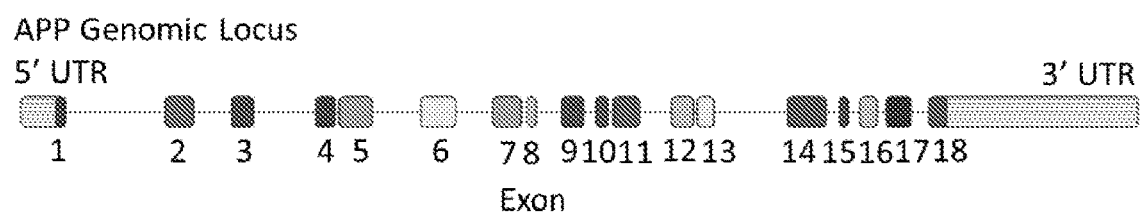
FIG. 17E illustrates a schema of structure of human APP genomic locus.

In small population RT-PCR, the splice variants APP 751 (NM_201413.2) and APP 695 (NM_201414.2) were detected. Smaller bands of varied sizes were also detected (FIG. 17B). RT-PCR on bulk RNA detected the highly expressed canonical APP 751 splice variants as the major product as well as smaller bands (FIG. 17C). These RT-PCR products were Southern blotted with $^{32}$P-labeled APP cDNA probes (FIG. 17D), which produced positive bands from duplicate gels, that were cloned and Sanger sequenced. APP splice variants 751 and 695 as well as non-classical variants of APP were detected and characterized by loss of central exons with proximal and distal exons linked by intraexonic junctions (IEJs) (FIG. 17E).

Figure 17F:
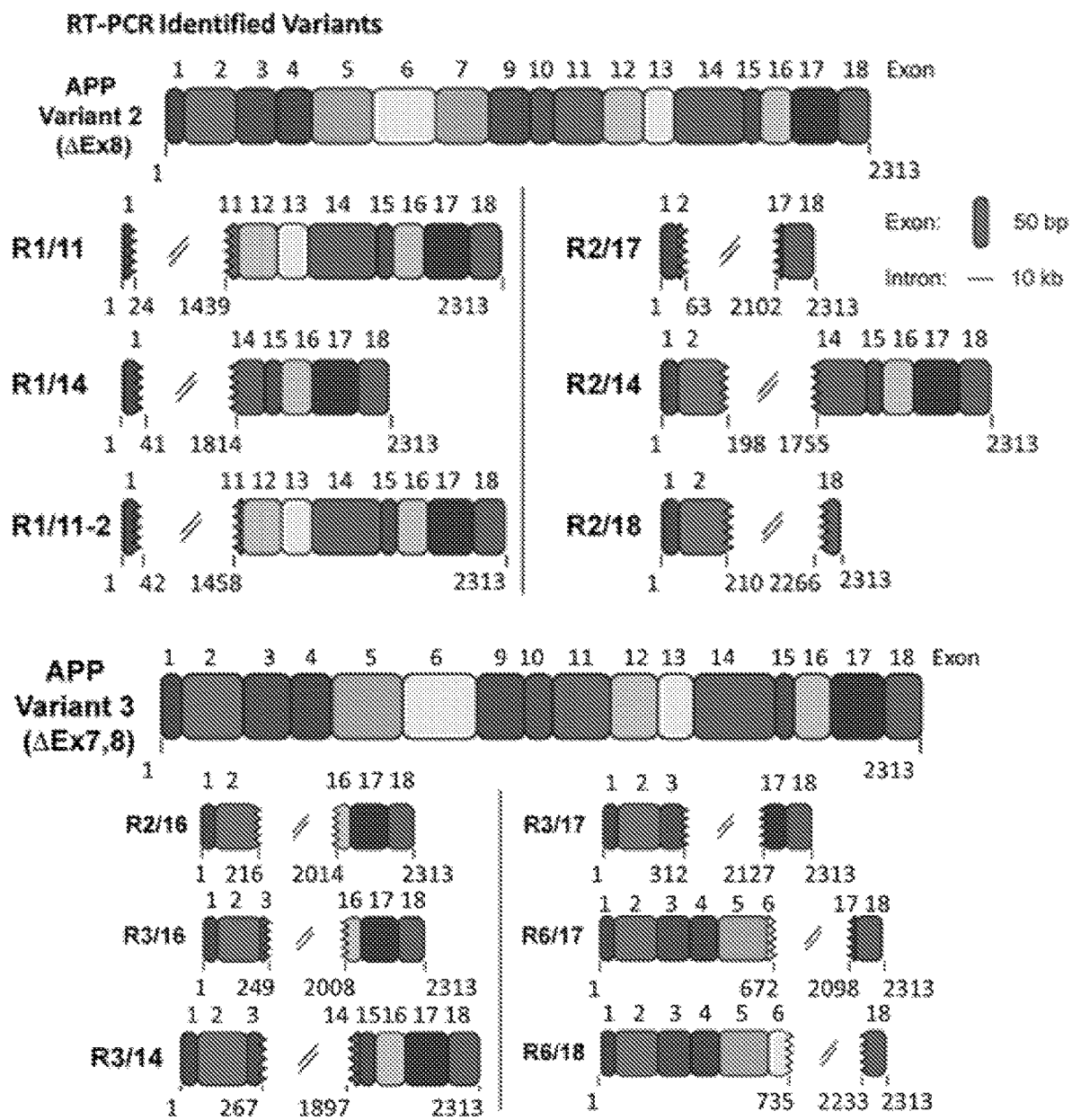
FIG. 17F illustrates schemas of non-classical RNA variants of APP identified by RT-PCR.
Figure 17G:
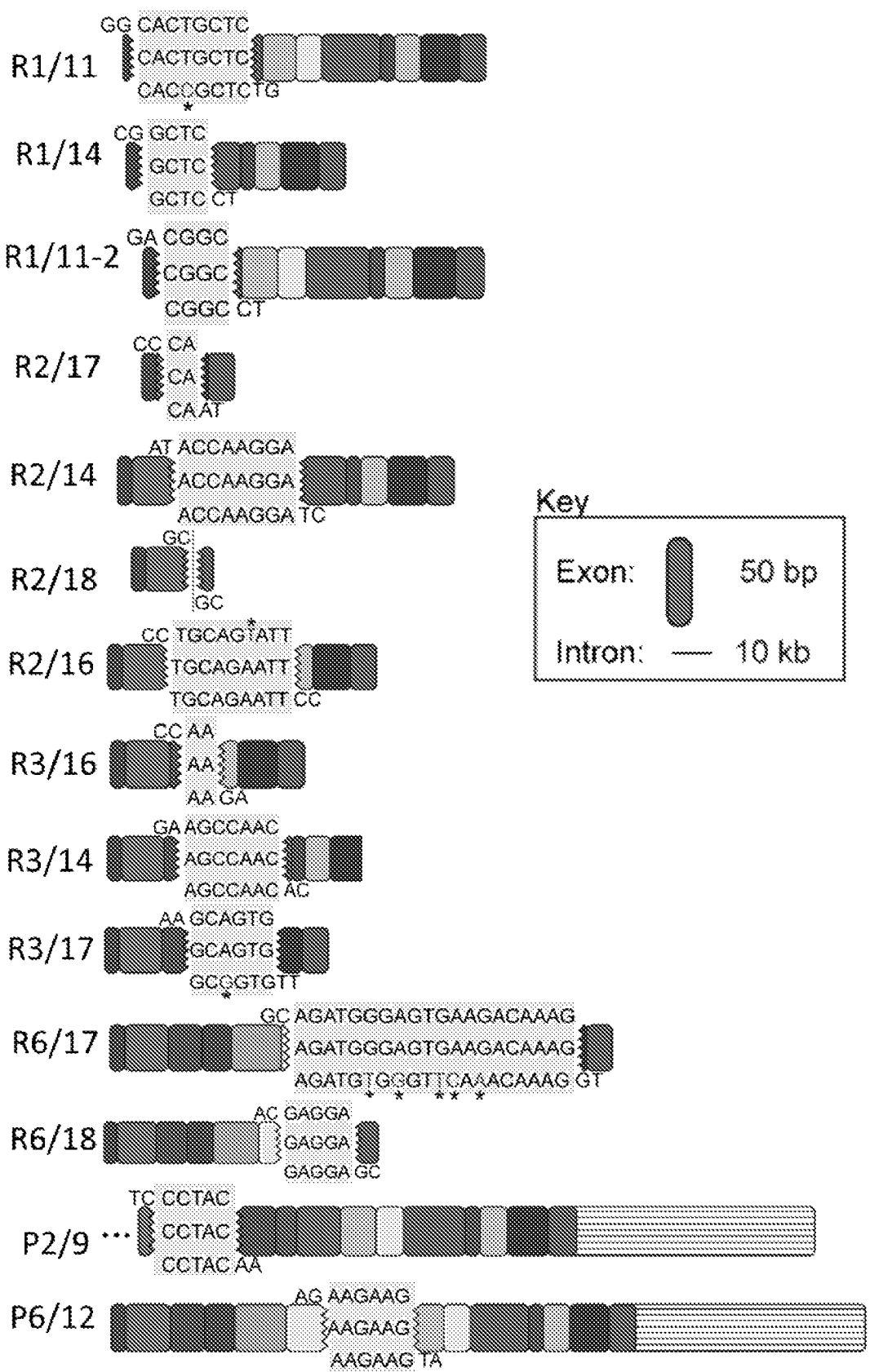
FIG. 17G illustrates schemas of sequence homology of non-classical RNA variants of APP at intraexonic junctions. Homology sequences of proximal and distal exons are shaded in gray. Middle sequence is the identified variant, top and bottom sequences are publicly available coding sequences from NM_000484.3 from the respective exons. Nucleotide variations are indicated an asterisk. Non-classical RNA variants identified by Sanger sequencing and PacBio data sets are shown with R and P, respectively. Figure discloses SEQ ID NOS 34-42, respectively, in order of appearance.
Figure 17H:
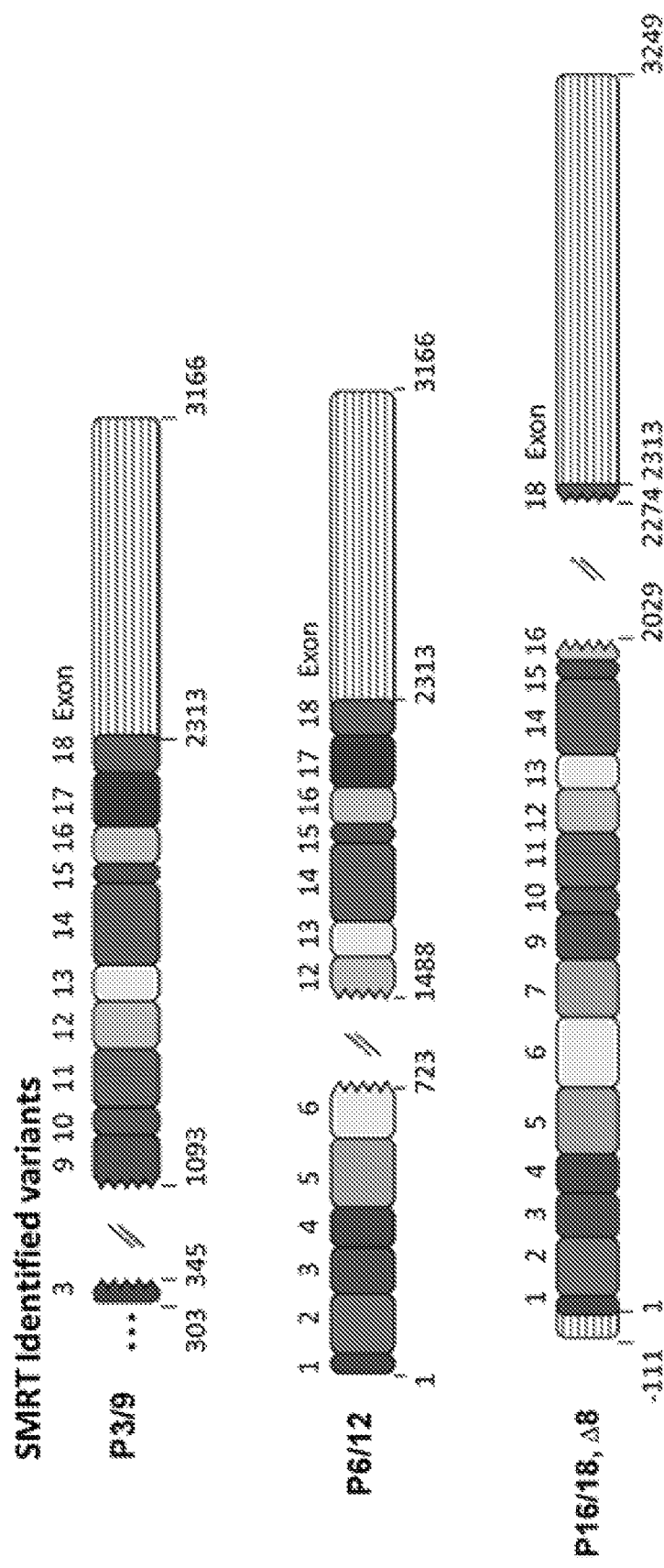
FIG. 17H illustrates non-classical RNA variants of APP identified from independent long-read single molecule real-time (SMRT) sequencing data sets.

Twelve non-classical variant sequences with IEJs were identified (FIG. 17F). One non-classical variant sequence was characterized by an IEJ between the 24$^{th}$ nucleotide of exon 3 and 45$^{th}$ nucleotide of exon 16 (FIG. 17F, "R3/16"). The sequence complementarity of joined exons was found in 11 IEJs ranging in overlap from 2 to 20 nucleotides (FIG. 17G). PCR artifacts were ruled out using independently produced long-read RNAseq data sets derived from oligo-dT-primed RNA from whole SAD brain and SAD temporal lobe, which yielded non-classical variants with similar IEJs (FIG. 17H).

Example 14. Non-Classical Genomic cDNA Variants of APP in Populations of Neuronal Nuclei Non-classical variants of APP were analyzed in genomic DNA from populations of neuronal nuclei.

Figure 18A:
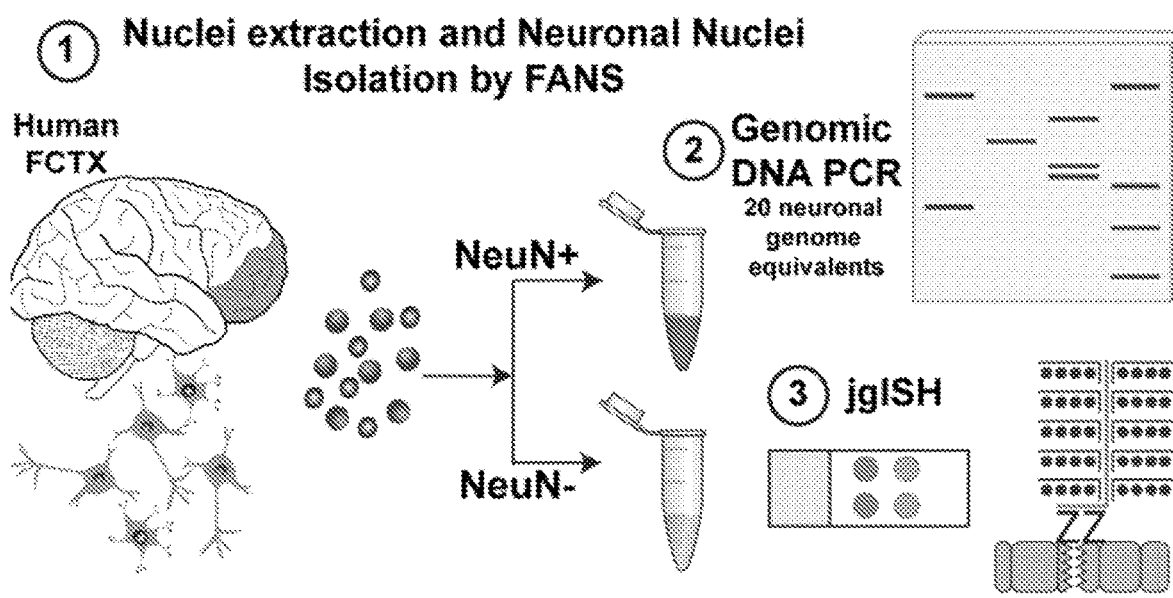
FIG. 18A illustrates a schema for analyzing non-classical genomic cDNA (gencDNA) variants of APP. (1) Neuronal nuclei from human prefrontal cortices (FCTX) were used for (2) genomic DNA PCR and (3) junction-specific genomic in situ hybridization (jgISH).
Figure 18B:
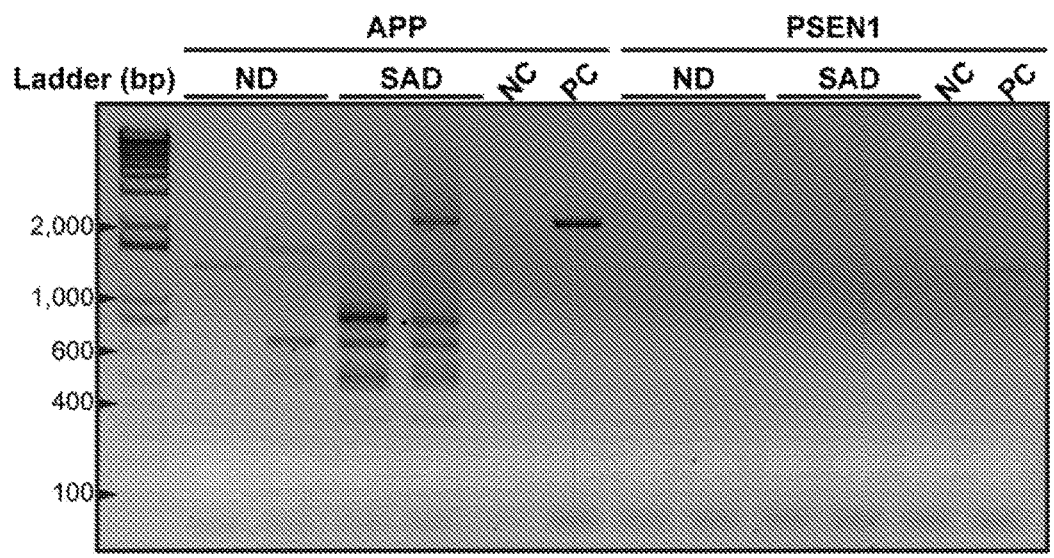
FIG. 18B illustrates a gel electrophoresis of genomic DNA PCR products with APP and PSEN1 primer sets using DNA from non-diseased (ND) and sporadic AD (SAD) neurons. Non-template control (NC) and positive control (PC) with indicated plasmids are shown.
Figure 18C:
FIG. 18C illustrates a schema showing 13 variants identified first by RT-PCR (APP-R) and DNA PCR (APP-D). Seven were identified in both methods, five by RT-PCR only, and one by DNA PCR only.
Figure 18C:
Figure 18C:
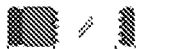
Figure 18C:
Figure 18C:
Figure 18C:
Figure 18C:
Figure 18C:
Figure 18C:
Figure 18C:
Figure 18C:
Figure 18C:
Figure 18C:

High-stringency amplification using the APP primers described above was pursued on thoroughly RNased DNA obtained from sets of 20 neuronal nuclei from both normal and SAD brains (FIG. 18A). PCR of nuclear genomic DNA generated clear bands that were similar in size to non-classical variants from RNA-derived RT-PCR products (FIG. 18B, ~100-2,300 bp). Interrogation of a second AD related gene, Presenilin 1 (PSEN1), did not produce products from genomic DNA (FIG. 18B; 94 Kb). Cloning and Sanger sequencing of these genomic DNA products revealed a range of genomic cDNAs (gencDNAs) showing precise exon::exon junctions, central exon deletions, and IEJs, including some species with sequences identical to the non-classical RNA variants identified (FIG. 18C).

Example 15. Non-Classical Genomic cDNA (GencDNA) Variants of APP in Single Nuclei The presence of APP gencDNA junctions within single neuronal genomes was analyzed using jgISH.

Figure 19A:
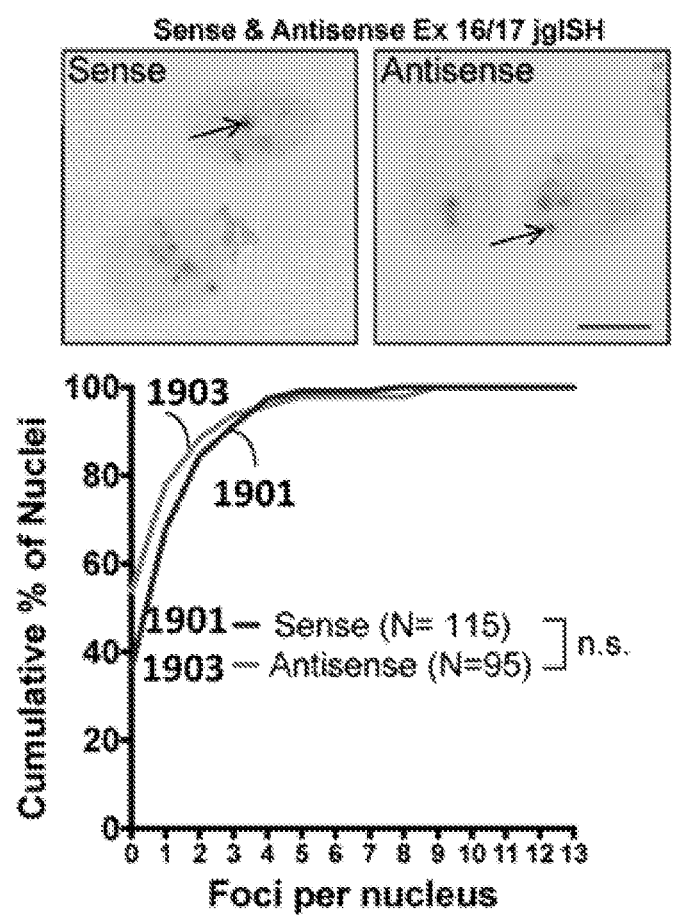
FIGS. 19A-19B illustrate jgISH performed with sense and anti-sense probes targeting APP exon 16 and exon 17 junction (Ex 16/17) (FIG. 19A) and intraexonic junction between APP exon 3 and exon 16 (IEJ 3/16) on SAD neuronal nuclei (FIG. 19B).
Figure 19B:
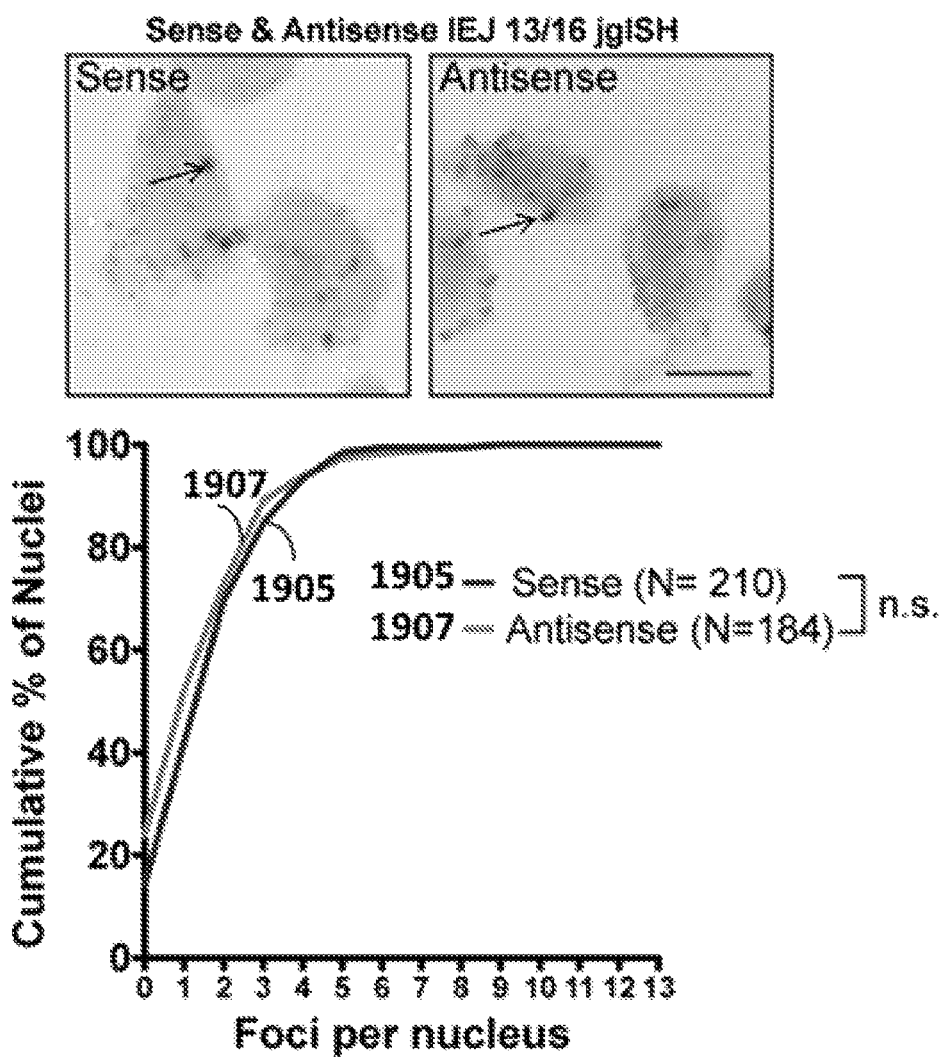
Figure 19C:
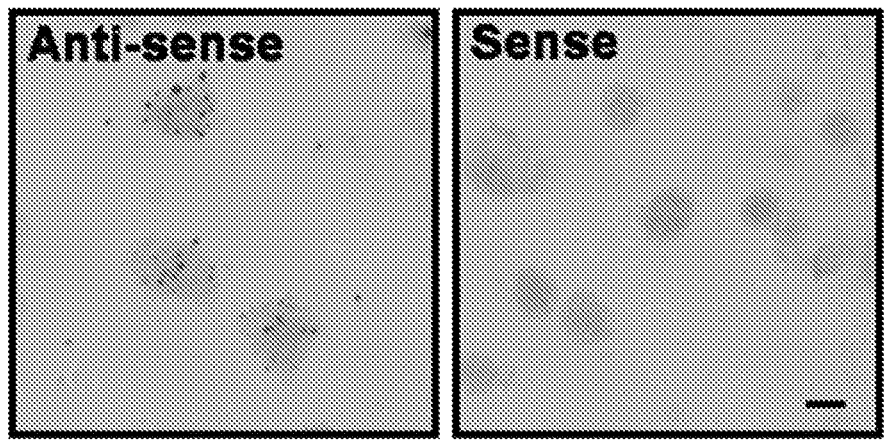
FIGS. 19C-19D illustrate RNA-in situ hybridization with sense and antisense jgISH probes on human tissue sections.
Figure 19D:
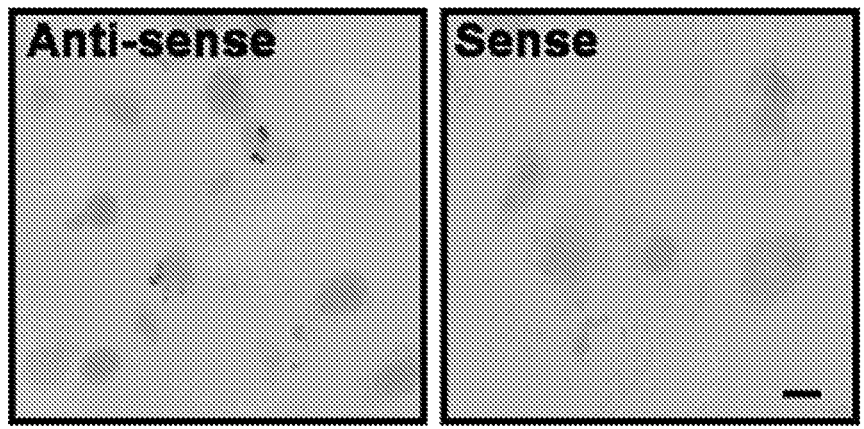
Figure 19E:
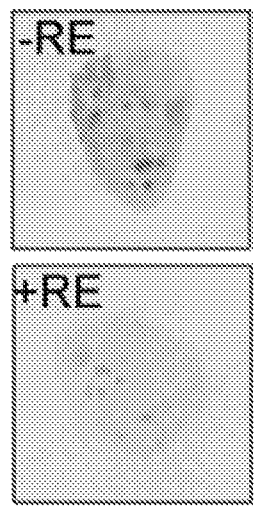
FIGS. 19E-19J illustrate restriction enzyme (RE) digestion. RE digestion was performed using MluCI (FIGS. 19E-19G) and PstI+MslI (FIGS. 19H-19J) to eliminate Ex 16/17 and IEJ 3/16 target sequences, respectively.
Figure 19F:
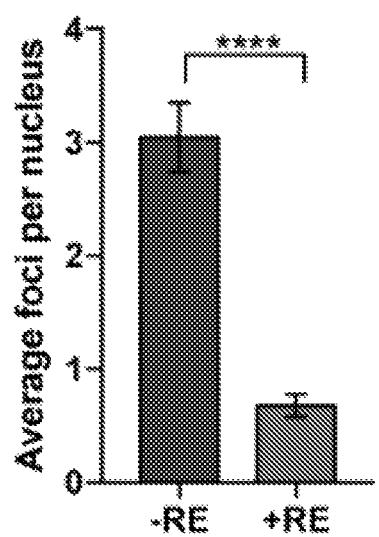
Figure 19G:
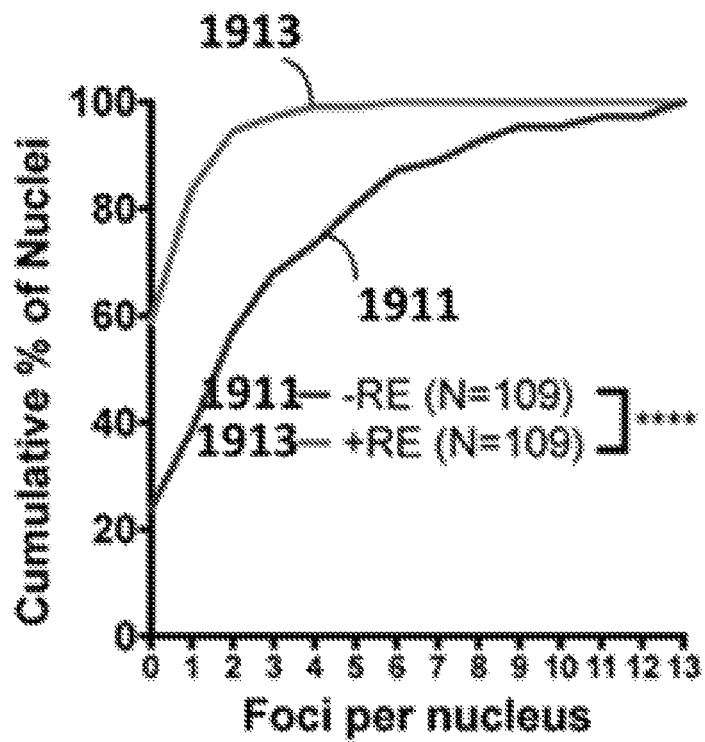
Figure 19H:
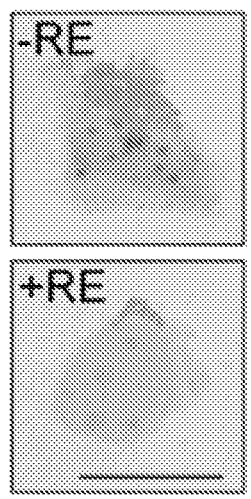
Figure 19I:
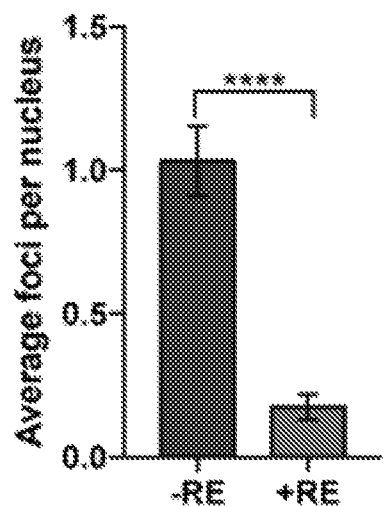
Figure 19J:
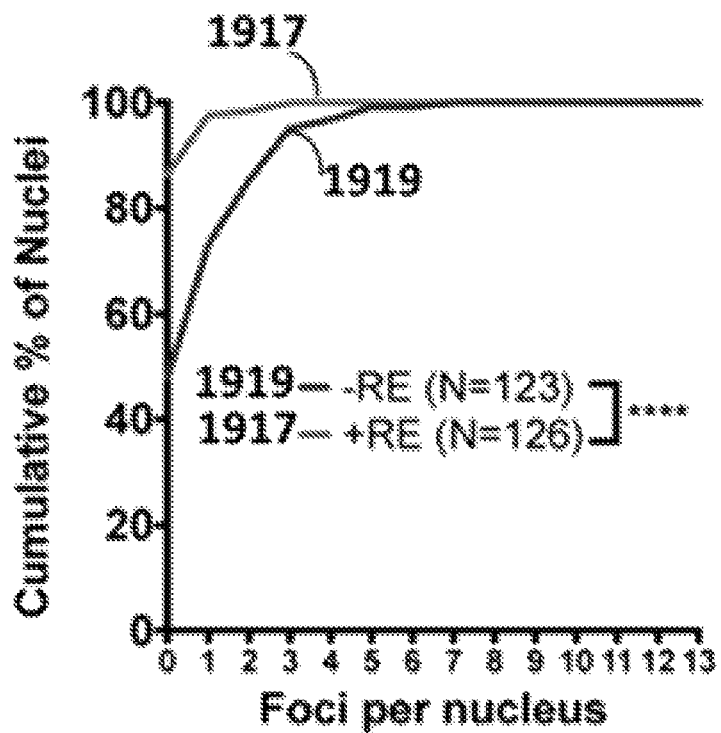

Briefly, sample preparation and hybridization protocols for RNA-ISH were used according to manufacturer's instruction (ACD, Newark, CA) to recognize genomic DNA sequences. Probes used passed multiple specificity requirements involving both positive and negative controls (Table 6). Two jgISH probes were used: one that recognized gencDNAs via the exon16::exon 17 junction (Ex 16/17), which spans the Ab coding region of APP; and one that recognized IEJ formed between exons 3 and 16 (IEJ 3/16), representing one APP variant. All bound probes were enzymatically visualized, appearing as red dots (as indicated by the arrows) of varied diameter. Both sense (1901, 1905) and anti-sense (1903, 1907) jgISH probes produced similar results in RNase treated SAD neuronal nuclei (FIGS. 19A-19B). By comparison, RNA signals were only detected using the anti-sense probes (FIGS. 19C-19D); therefore sense probes were exclusively used for genomic DNA detection. The jgISH sense probe signals were eliminated by specific restriction enzyme digestion of genomic DNA that eliminated the sequence recognition site (FIGS. 19E-19J).

TABLE 6

List of jgISH positive control, negative control, and experimental probes

| Junction | Target | Sample | Type | Probes |
|---|---|---|---|---|
| Ex 16/17 | DNA | Human nuclei +RNase | Exp | Sense |
| | | | Exp | Anti-sense |
| | | Human nuclei +RNase +/− restriction enzyme (MluCI) | Neg | Sense |
| | | | | Sense |
| | | WT mouse nuclei +RNase | Neg | Sense |
| | | Mouse nuclei +RNase + Ex 16/17 DNA concatamer | Pos | Sense |
| | RNA | Human tissue | Neg | Sense |
| | | | Pos | Anti-sense |
| IEJ 3/16 | DNA | Human nuclei +RNase | Exp | Sense |
| | | | Exp | Anti-sense |
| | | Human nuclei +RNase +/− restriction enzyme (PSTI & MslI) | Neg | Sense |
| | | | | Sense |
| | | WT Mouse nuclei +RNase | Neg | Sense |
| | RNA | Human tissue | Neg | Sense |
| | | | Pos | Anti-sense |

Exp = Experimental,
Neg = negative control,
Pos = positive control

This example shows that the jgISH protocol detected specific genomic junctions without polymerase dependent template amplification. Moreover, use of Ex16/17 and IEJ 3/16 probes identified the mosaic presence of these gencDNA sequences in neuronal nuclei.

Figure 20A:
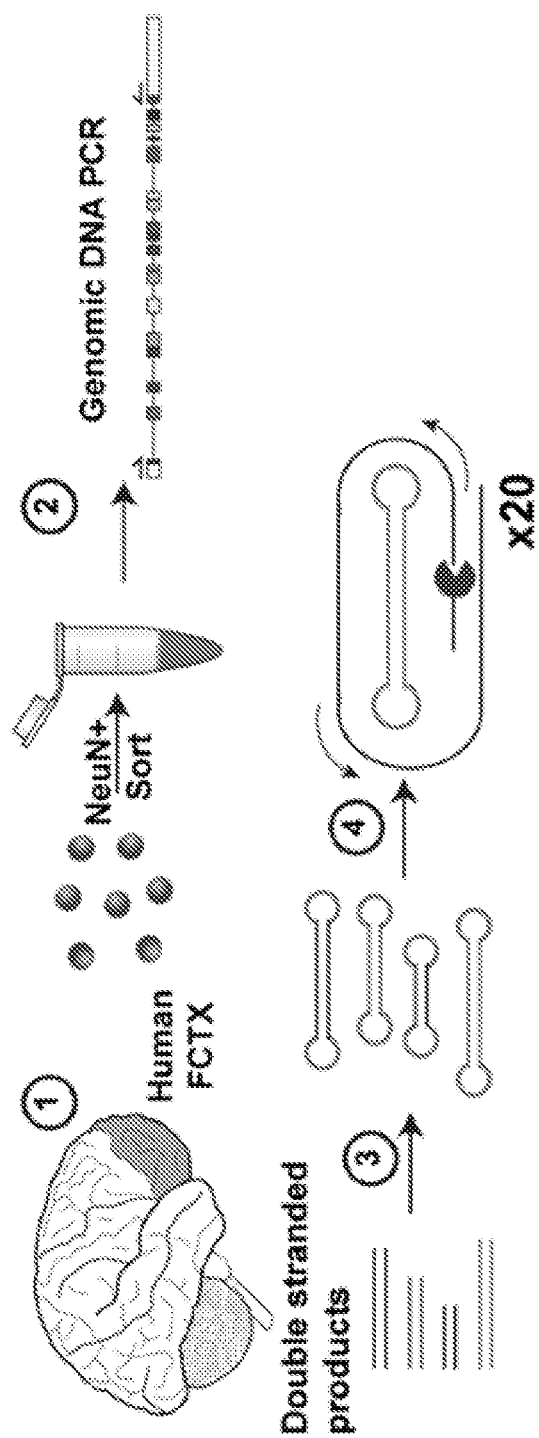
FIG. 20A illustrates a schema of non-classical gencDNAs variants of APP identified by SMRT sequencing from SAD brains. (1) Neuronal nuclei from SAD prefrontal cortex (FCTX) were sorted and used for (2) genomic DNA PCR. Multiple reactions were pooled for (3) library preparation to enable (4) high fidelity sequencing (SMRT 20×CCS calling).
Figure 20C:
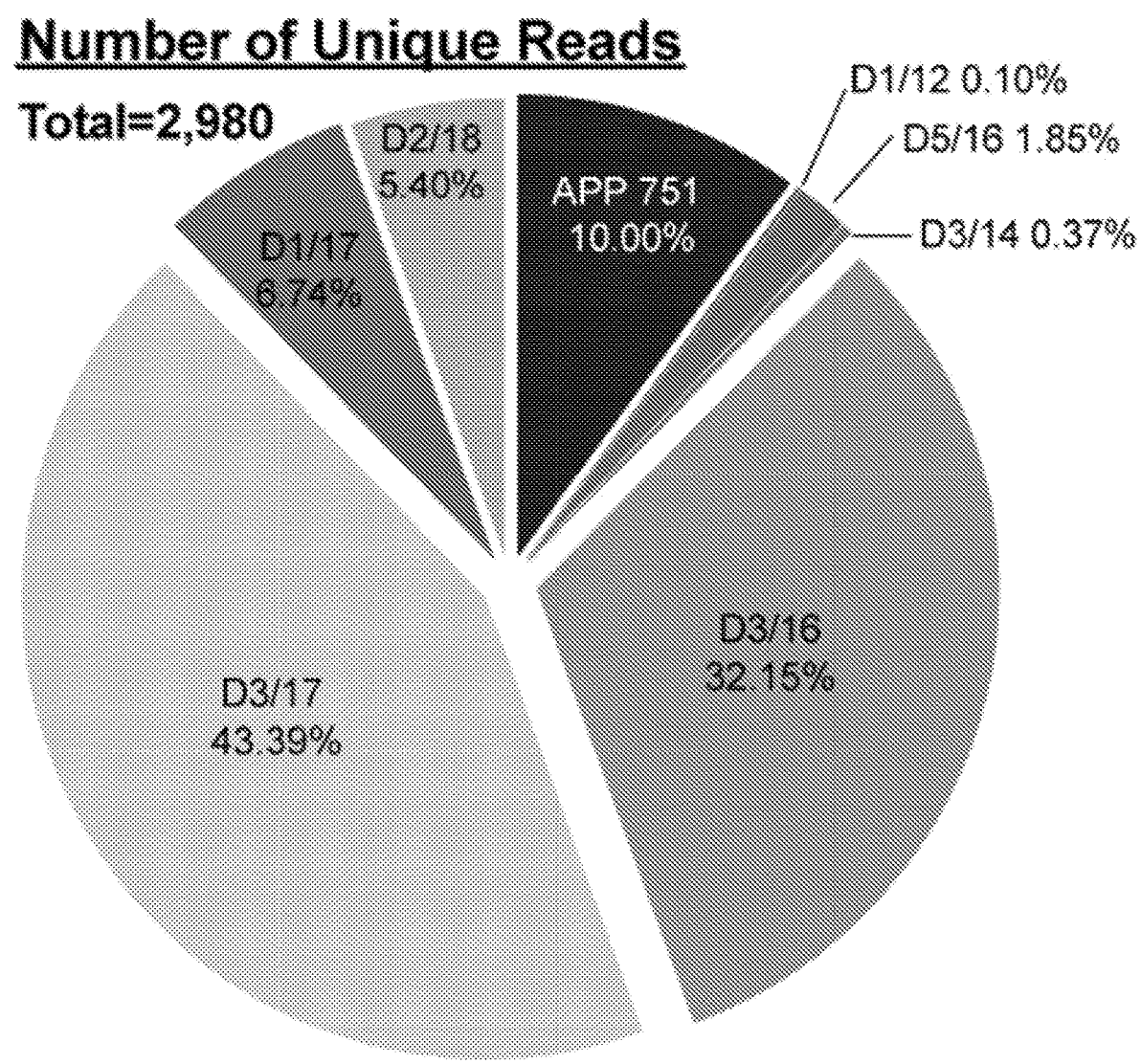
FIG. 20C illustrates a chart of total number and proportion of unique reads from each identified IEJ form.
Figure 20D:
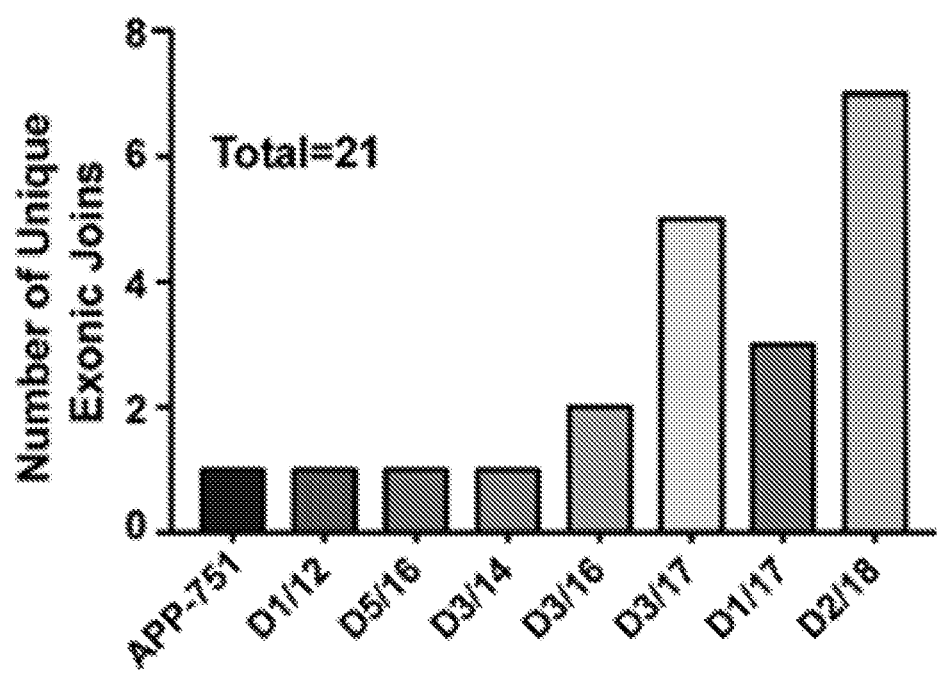
FIG. 20D illustrates a graph of number of unique IEJs forms.
Figure 20E:
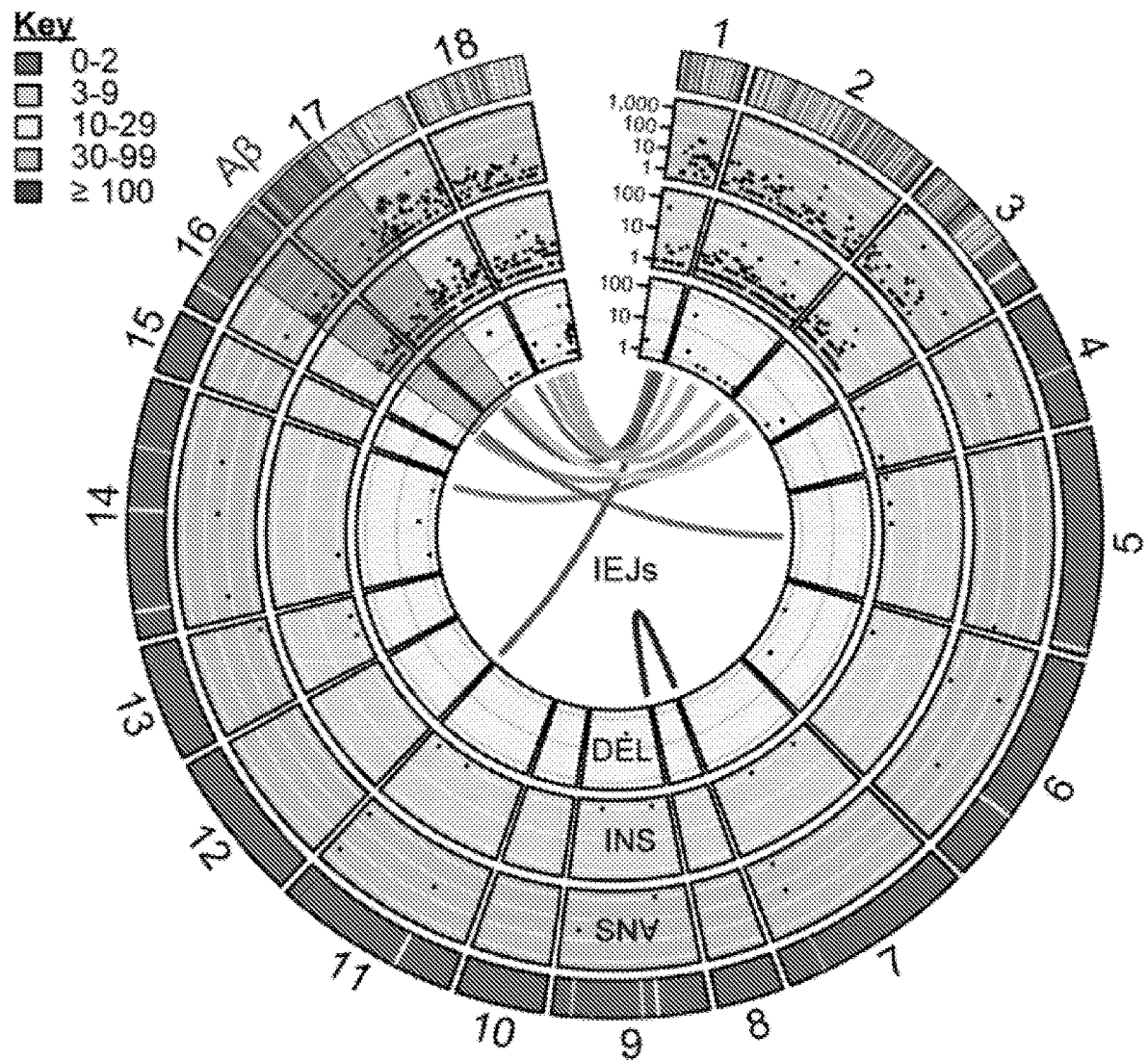
FIG. 20E illustrates a concentric circle plot of the APP locus (exon numbers along perimeter) illustrating IEJs (connecting lines inside the circles), deletions (DEL) (first inner circle), insertions (INS) (second inner circle), and single nucleotide variations (SNVs) (third inner circle) from sporadic Alzheimer's Disease (SAD) brains. Black dots indicate the abundance of DELs, INSs, and SNVs on a log (10) scale at the specified exon location. The outermost circle illustrates the sum count (key) of unique changes. Aβ region is highlighted, and known familial AD mutations are circled.
Figure 20F:
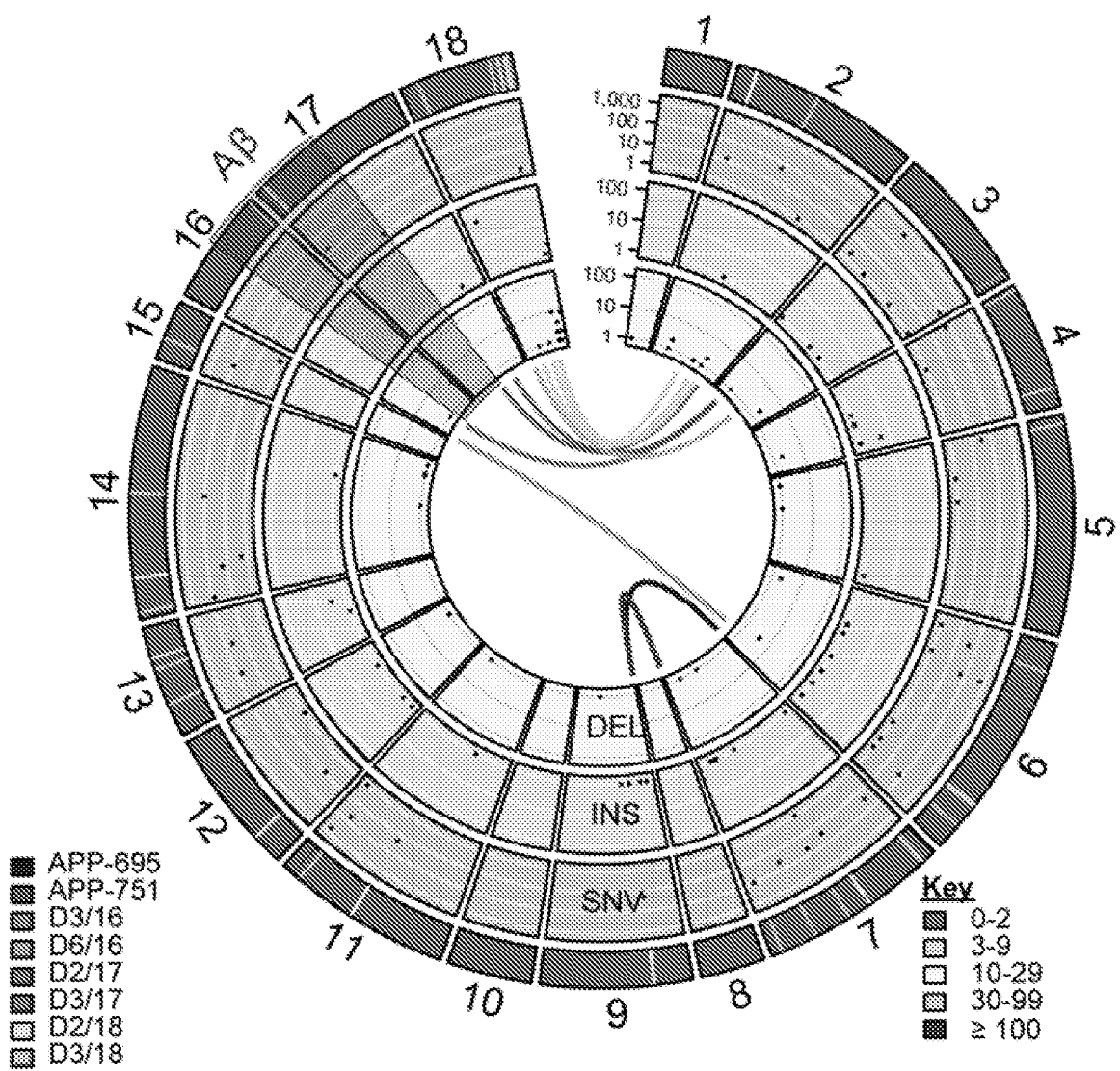
FIG. 20F illustrates a concentric circle plot of the APP locus (exon numbers along perimeter) illustrating IEJs (connecting lines inside the circles), deletions (DEL) (first inner circle), insertions (INS) (second inner circle), and single nucleotide variations (SNVs) (third inner circle) from non-diseased brains. Black dots indicate the abundance of DELs, INSs, and SNVs on a log (10) scale at the specified exon location. Outermost circle illustrates the sum count (key) of unique changes. Aβ region is highlighted.

Example 16. Thousands of Distinct APP GencDNAs from Populations of Neuronal Nuclei Non-classical gencDNA variants of APP were analyzed using multiple independent reactions on neuronal populations from brains (FIG. 20A), utilizing a DNA polymerase with 100× higher fidelity compared to native Taq (Invitrogen, Platinum SuperFi DNA Polymerase). The resulting samples were pooled for library preparation to enable SMRT CCS of single DNA molecules. SMRT libraries yielded high-certainty consensus calling (20 CCS subreads with 99.9999% accuracy, median Phred score of 93). The number of unique sequences included 2,980 sequences. These included 21 different IEJs identified in neuronal nuclei of 2 SAD brains (FIGS. 20B-20E) and 858 unique sequences including 11 IEJs in neuronal nuclei of 1 non-diseased brain. See FIG. 18C. GencDNAs of the canonical neuronal splice variant, APP 751, were also identified in both SAD and non-diseased datasets. SNVs, and insertions and deletions (INDELs) also occurred within APP gencDNAs of both SAD and non-diseased brain (FIGS. 20E-20F).

Example 17. Linkage Between GencDNAs and AD in Neurons

Figure 21A:
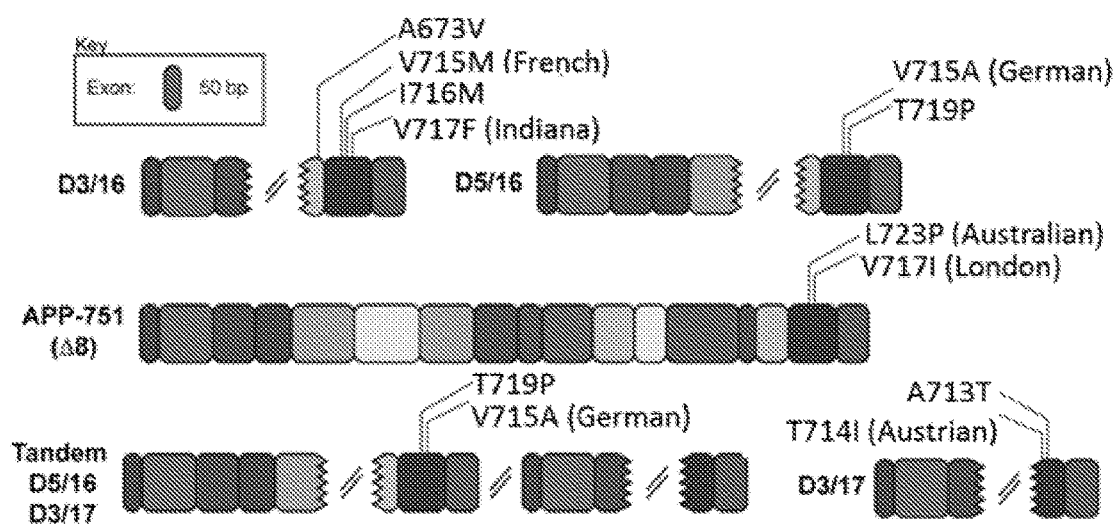
FIG. 21A illustrates 10 different familial AD mutations present in APP gencDNAs. In-frame mutations (A673V, V715M, I716M, V717F, L723P, and V717I) out-of-frame mutations (V715A, T719P, A713T, T714I) are indicated based on the known APP reading frame analysis.
Figure 21B:
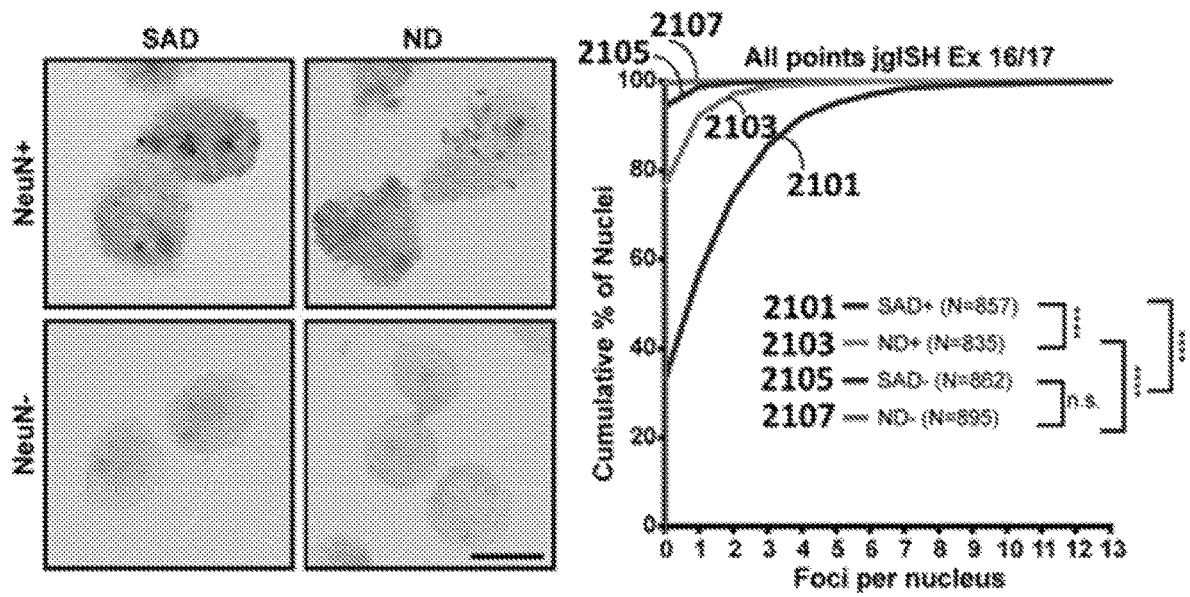
FIGS. 21B-21C illustrate nuclei sorted from 6 ND and 6 SAD cortices. Nuclei were analyzed by Ex 16/17 (FIG. 21B) and IEJ 3/16 jgISH (FIG. 21C). Cumulative frequency distribution plots of number of foci per nucleus showed statistical significance (nonparametric Kruskal-Wallis test with Dunn's multiple corrections). ****P<0.0001. n.s., not-significant. Error bars are ±SEM. Scale bars are 10 µm.
Figure 21C:
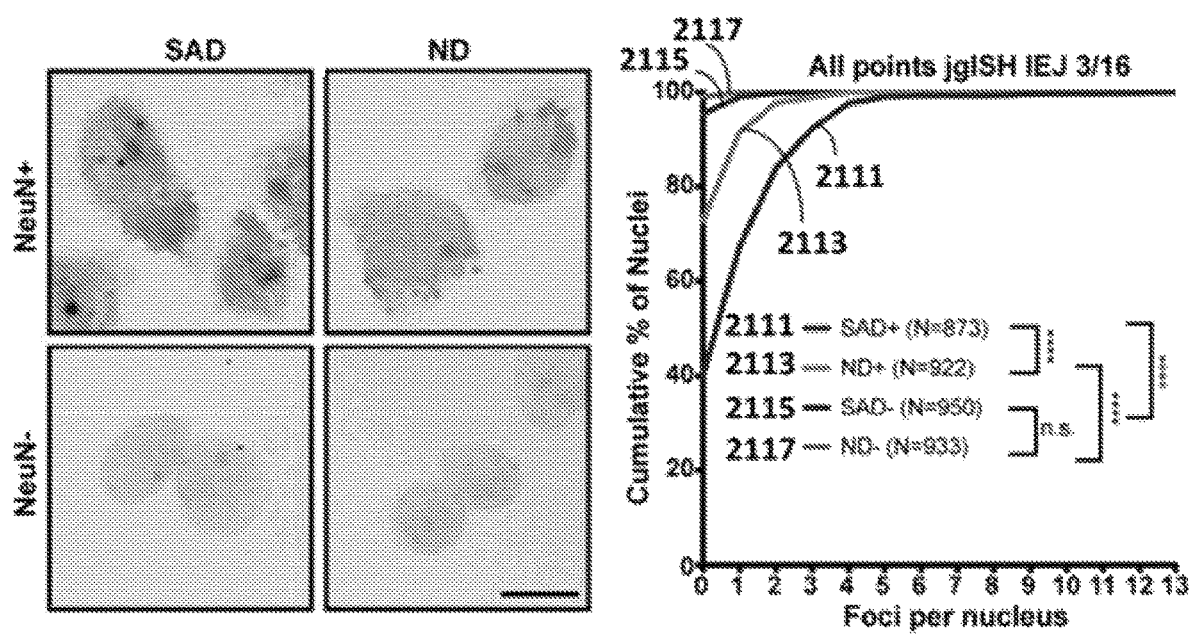
Figure 21D:
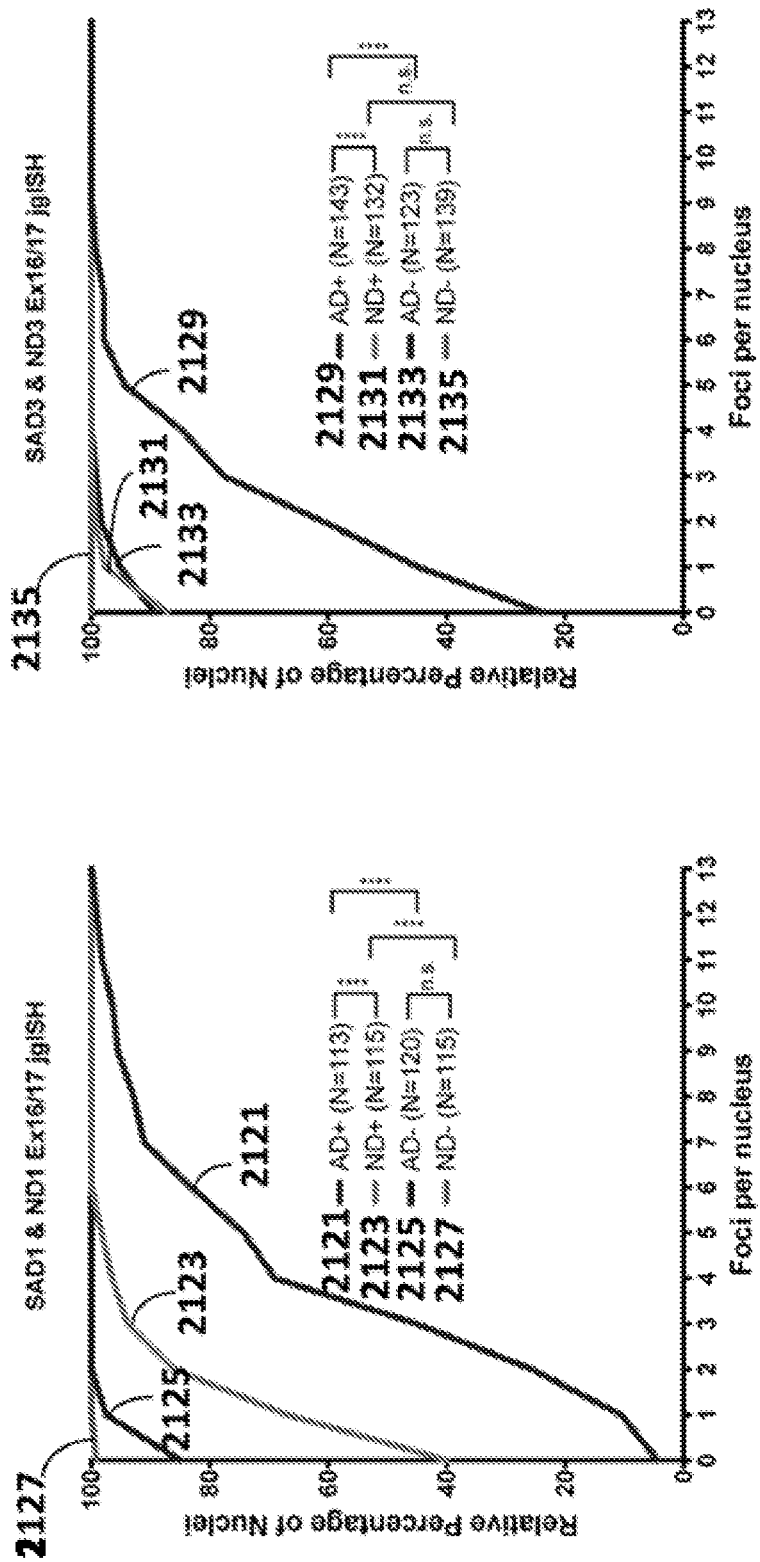
FIGS. 21D-21I illustrate plots of relative percentage of nuclei sorted from 6 ND and 6 SAD cortices. Nuclei were analyzed by Ex 16/17 (FIGS. 21D-21F) and IEJ 3/16 (FIGS. 21G-21I) jgISH. Cumulative frequency distribution plots of number of foci per nucleus showed statistical significance (nonparametric Kruskal-Wallis test with Dunn's multiple corrections). *p<0.05, p<0.01, *p<0.001, ****p<0.0001. n.s., not-significant. Error bars are ±SEM.
Figure 21E:
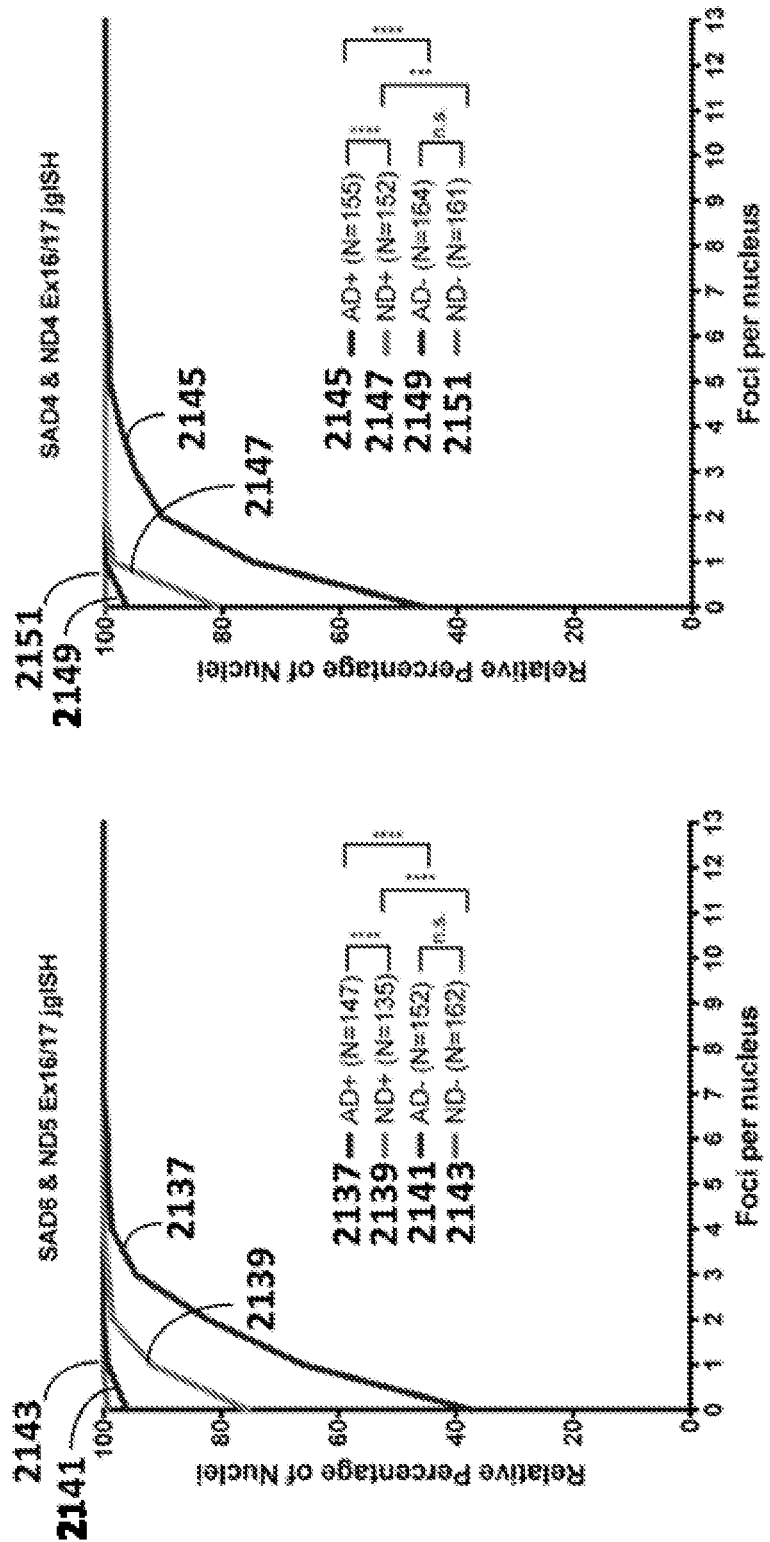
Figure 21F:
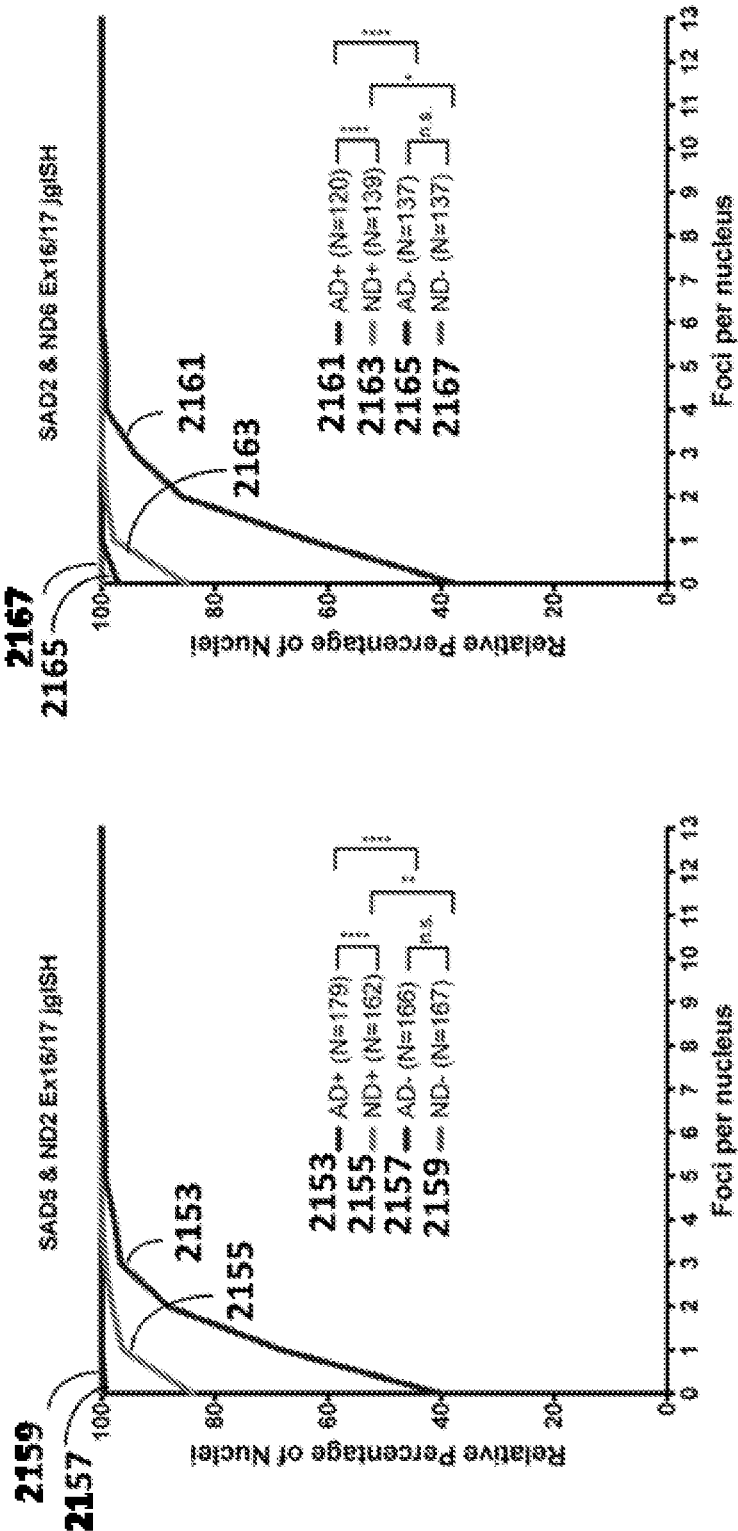
Figure 21G:
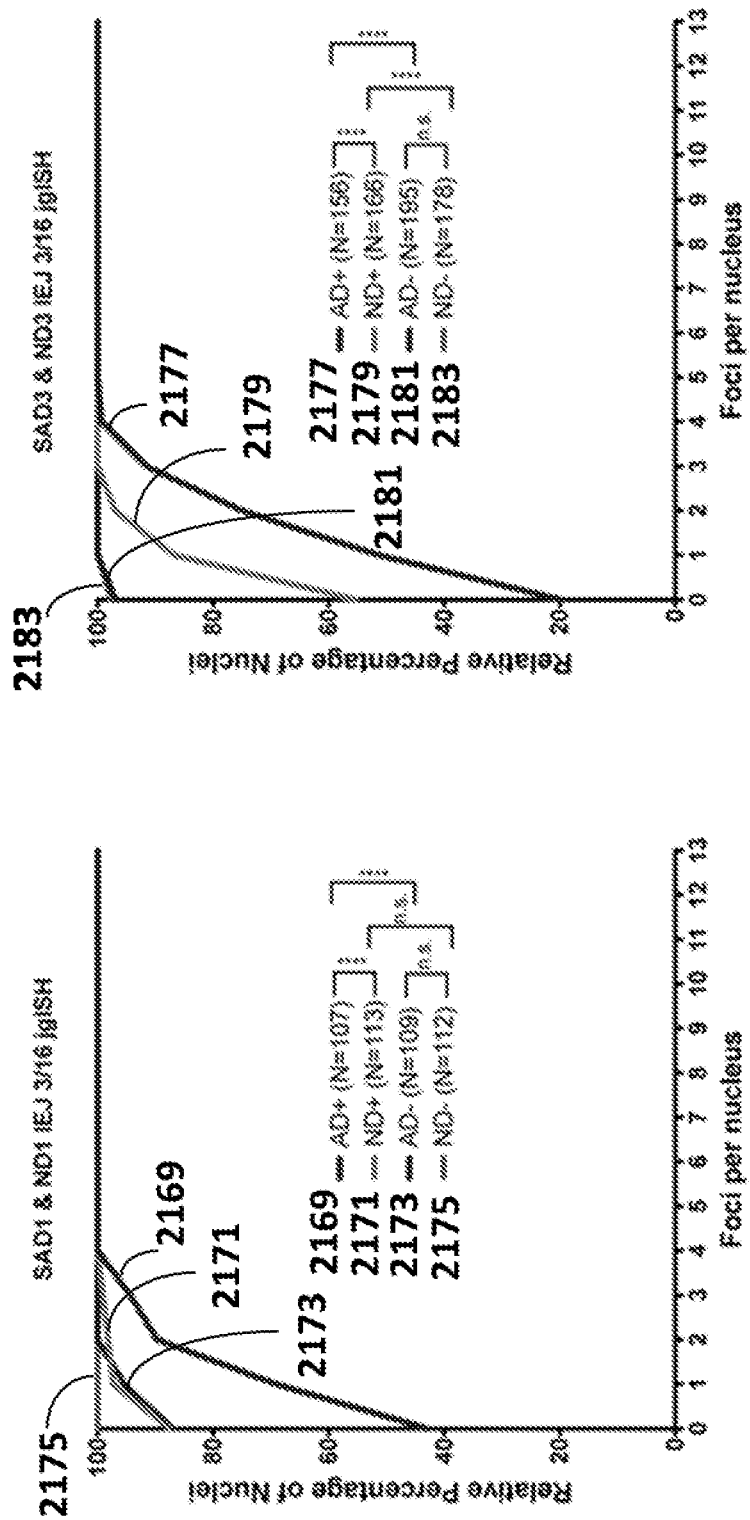
Figure 21H:
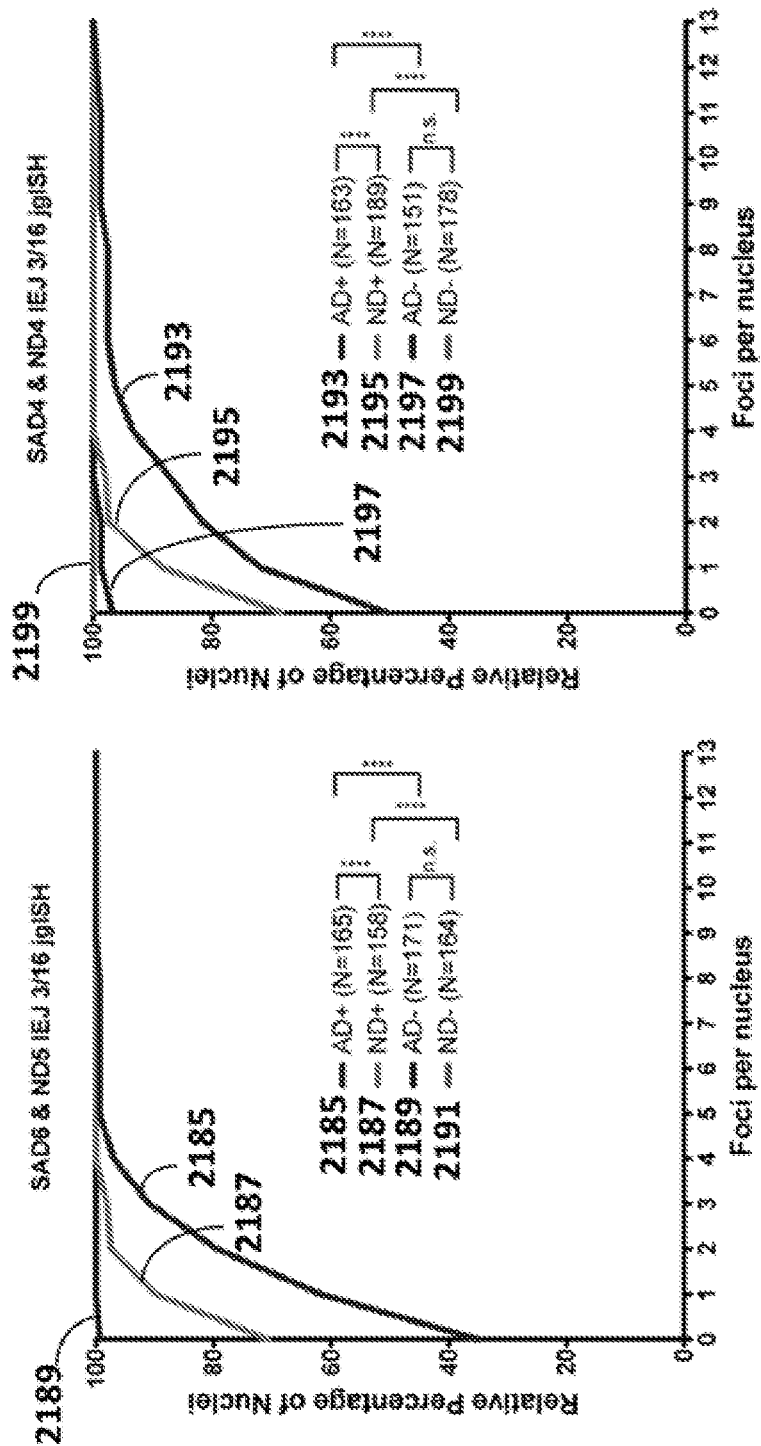
Figure 21I:
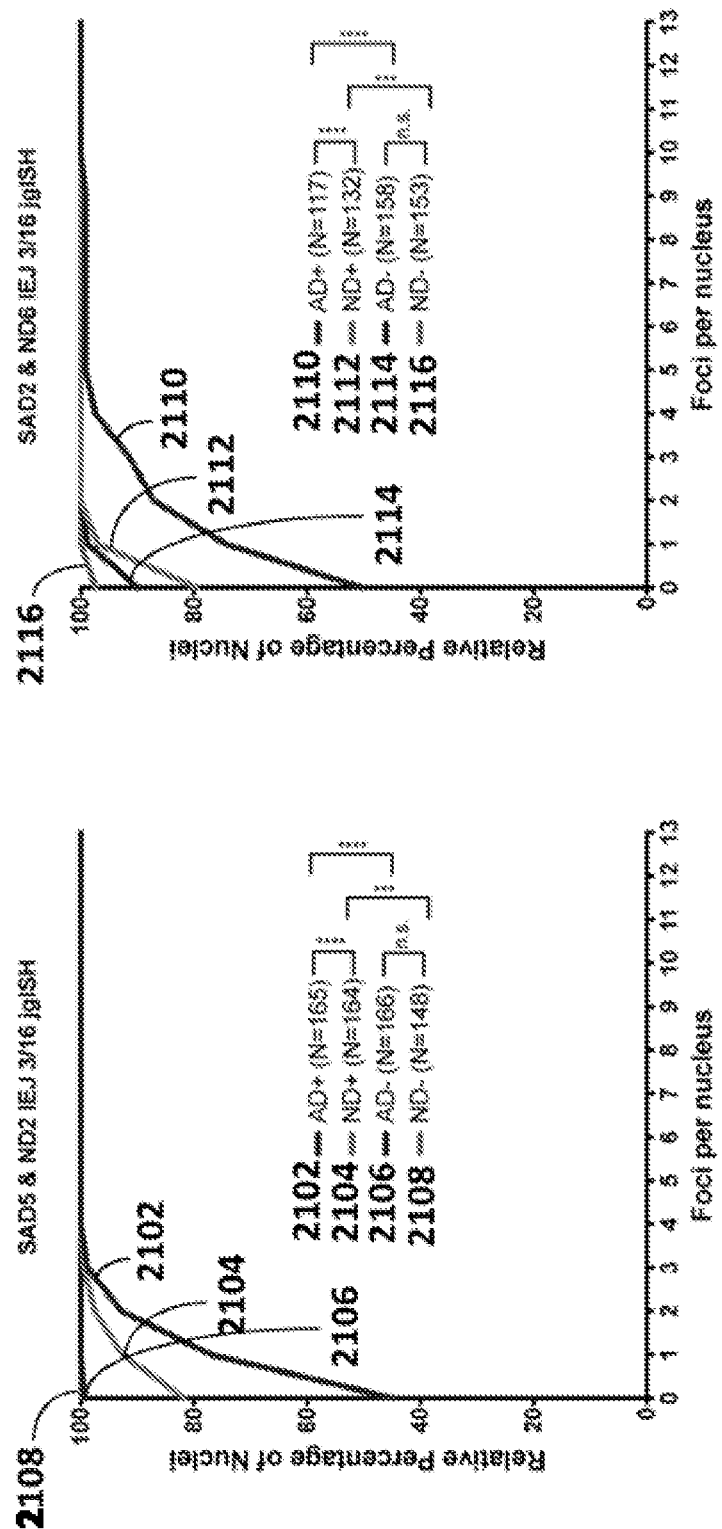
Figure 22A:
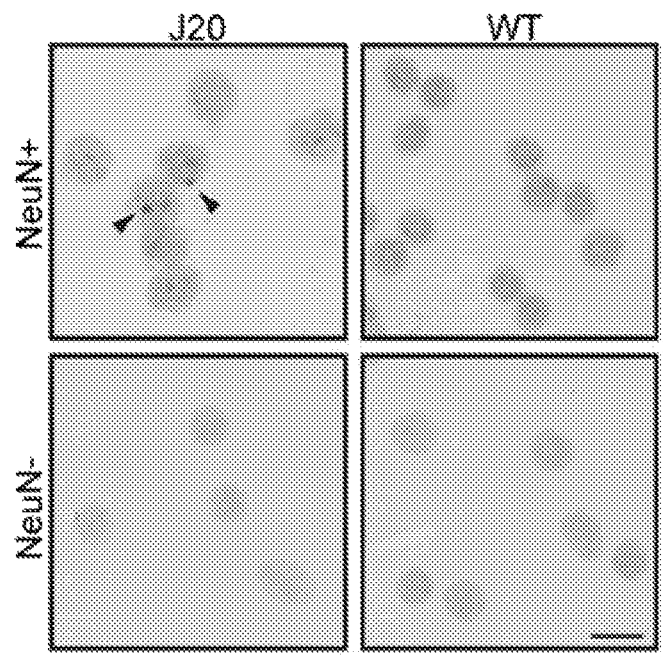
FIG. 22A illustrates images of IEJ 3/16 jgISH of nuclei isolated from the cortex of an AD mouse model (J20 transgenic, with neuron specific expression of human APP cDNA containing Swedish and Indiana mutations) versus WT littermates. Error bars are ±SEM. Scale bars are 10 µm.
Figure 22B:
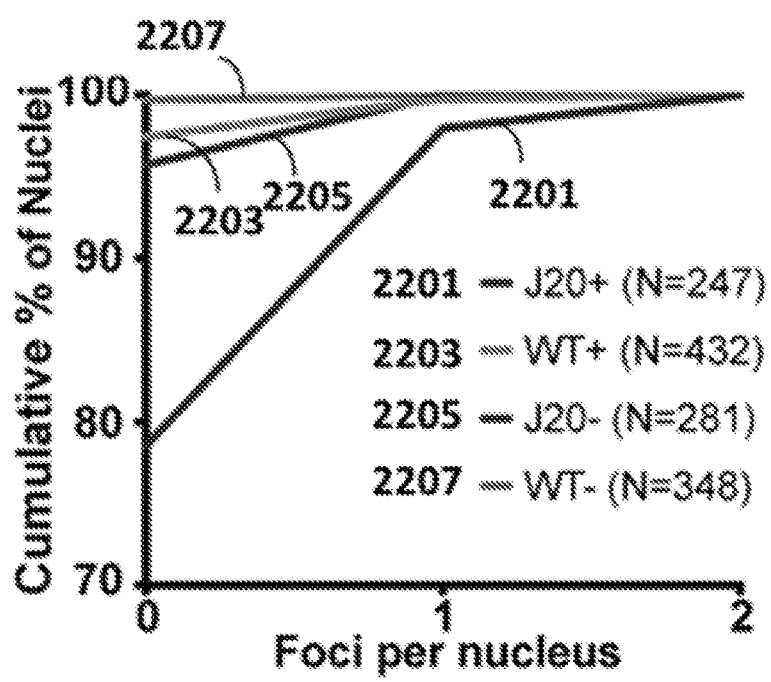
FIGS. 22B-22C illustrate quantification of nuclei from FIG. 22A.
Figure 22C:
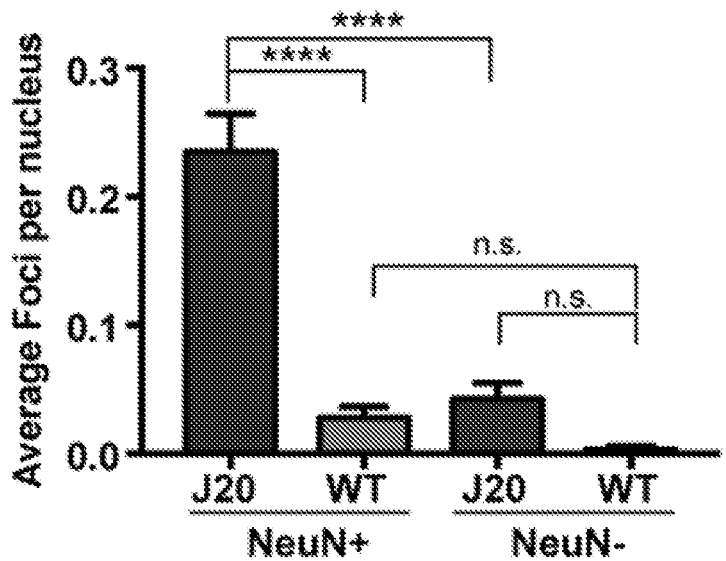
Figure 22D:
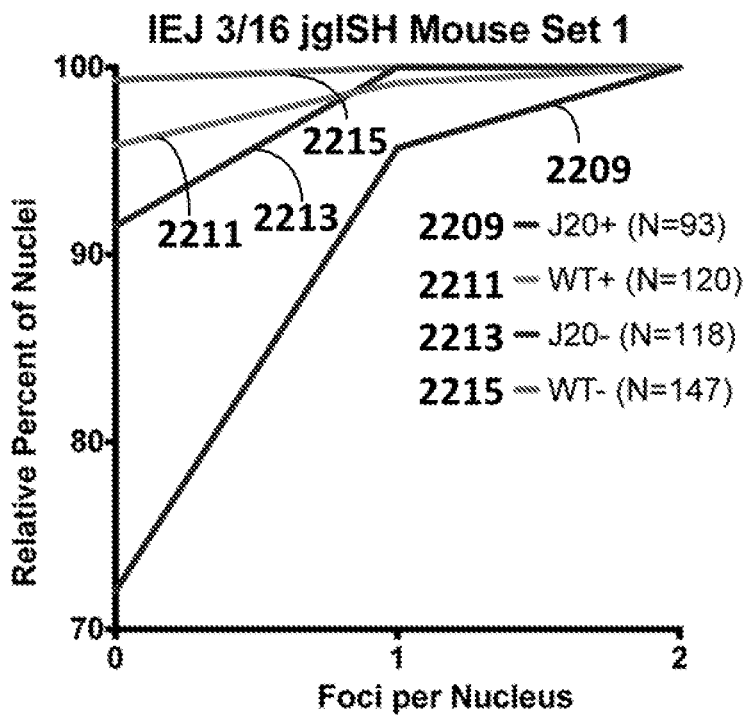
FIGS. 22D-22G illustrate IEJ 3/16 jgISH from two mouse experiments.
Figure 22E:
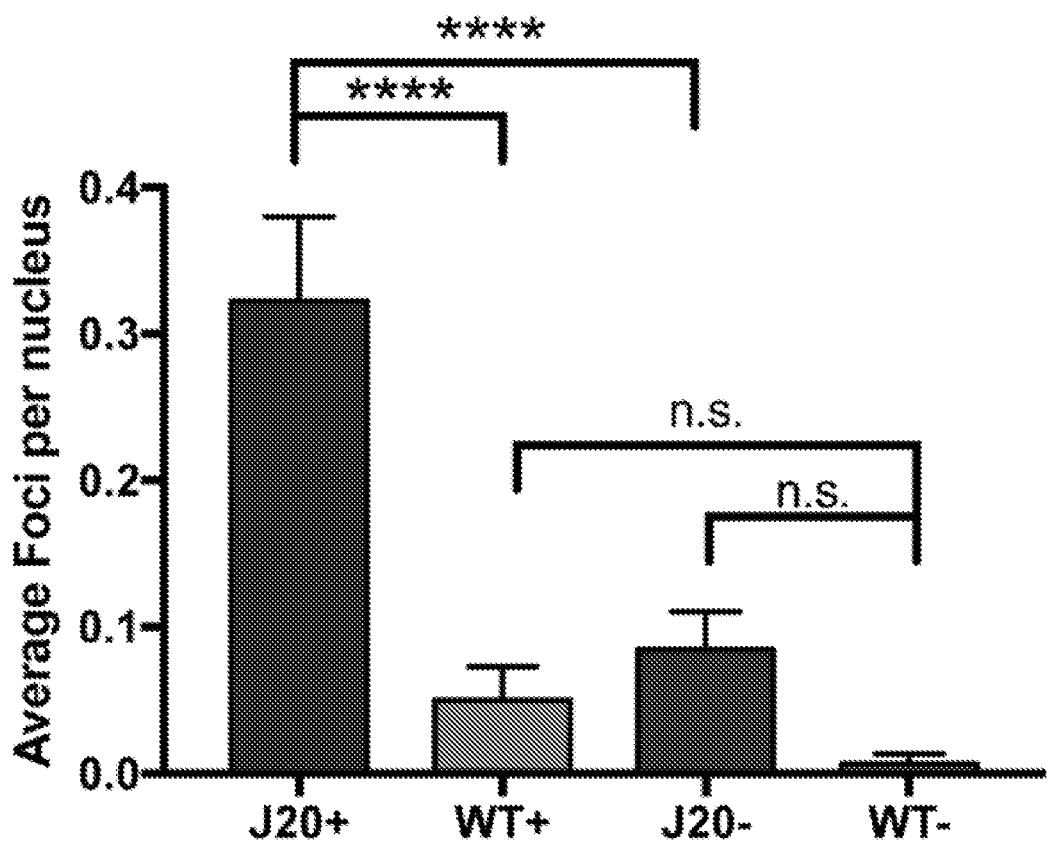
Figure 22F:
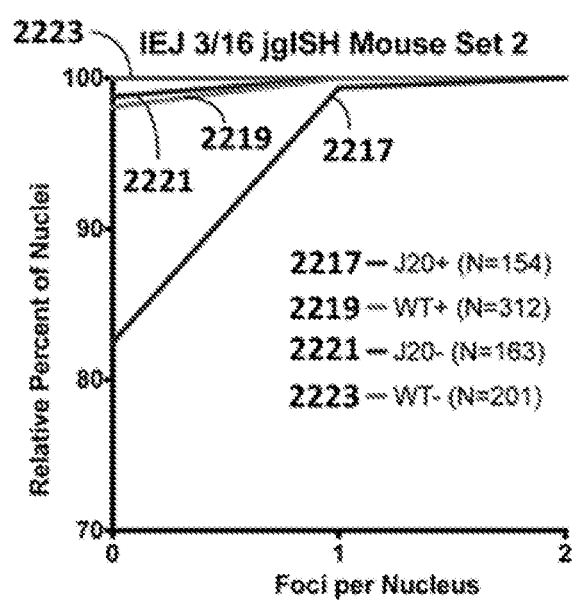
Figure 22G:
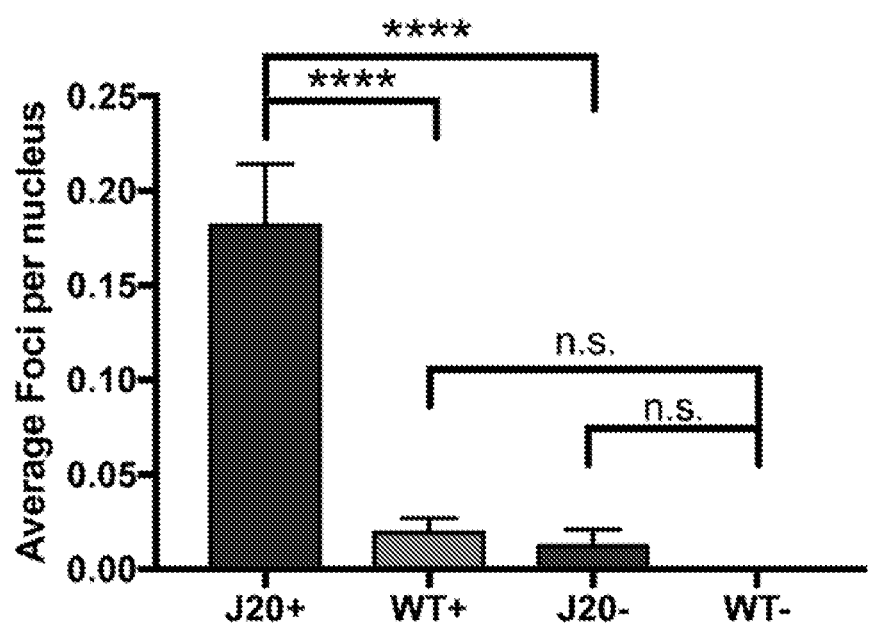

GencDNA forms of mosaic neuronal recombination for potential relevance to SAD were assessed. Ten different SNVs in gencDNA variants from SAD but not non-diseased neurons were identified that were identical to pathogenic FAD APP mutations, including the Indiana mutation (FIG. 20E and FIG. 21A). Relationships of identified gencDNA variants to SAD were analyzed by comparing non-diseased and SAD neurons using jgISH.

Two gencDNA junctions, Ex 16/17 and IEJ 3/16, were examined in neurons from clinically and neuropathologically verified SAD brains (See Table 5) and compared to 6 non-diseased brains (FIGS. 21B-21I). The number of red foci in AD neurons was 3-5 fold higher than in non-diseased neurons. Rare foci were observed in non-neuronal (NeuN-negative) nuclei that were not statistically significant between cells from SAD and non-diseased brain, despite being from the same brains that had revealed disease-related changes in neurons. Recombination of APP at both Ex 16/17 and IEJ 3/16 was present in the J20 neurons (FIGS. 22A-22G).

Example 18. GencDNA Production Increases with Age in J20 Neurons

Figure 23A:
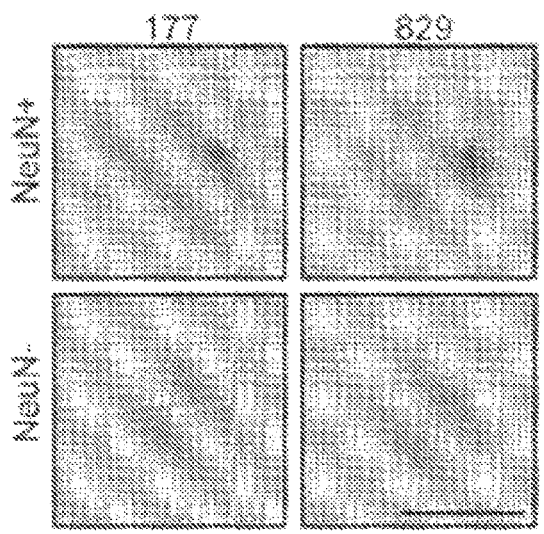
FIG. 23A illustrates images of representative nuclei isolated from 177 and 829-day J20 cortices. Scale bars are 10 µm.
Figure 23B:
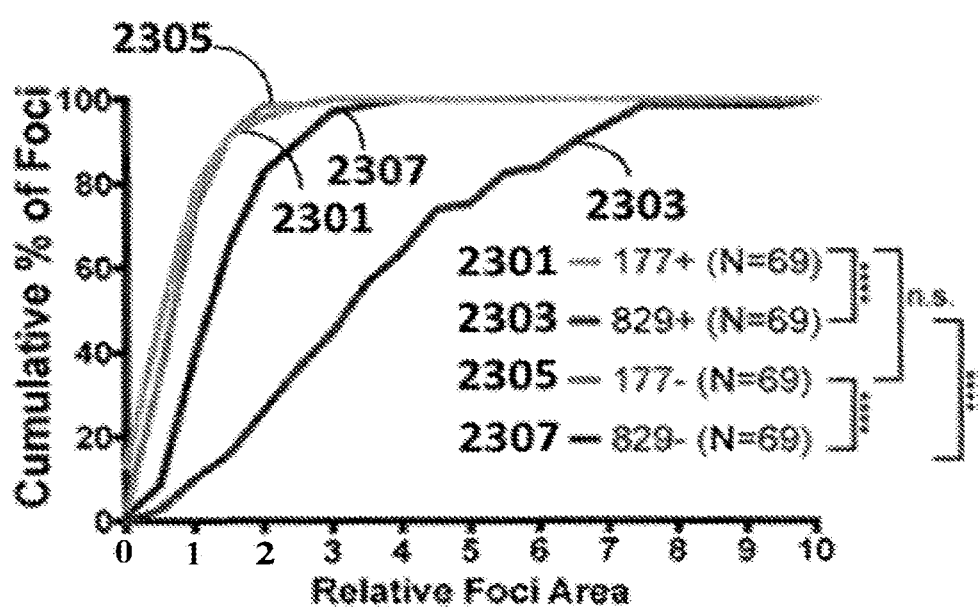
FIG. 23B illustrates a graph of cumulative percentage distribution of foci area (y-axis) as compared to relative foci area (x-axis) of nuclei from FIG. 23A.
Figure 23C:
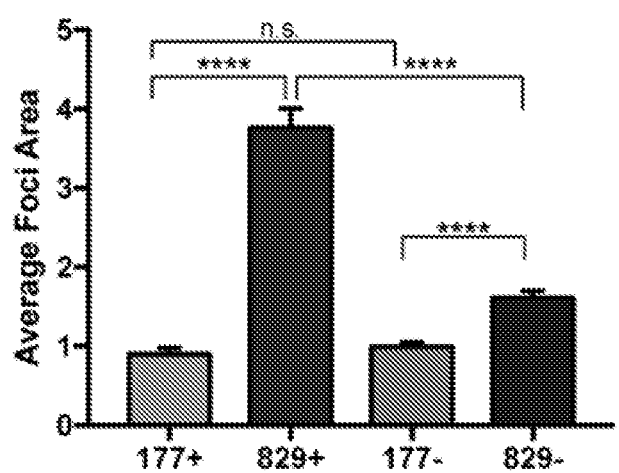
FIG. 23C illustrates a graph of average foci area (y-axis) of nuclei from FIG. 23A.
Figure 23D:
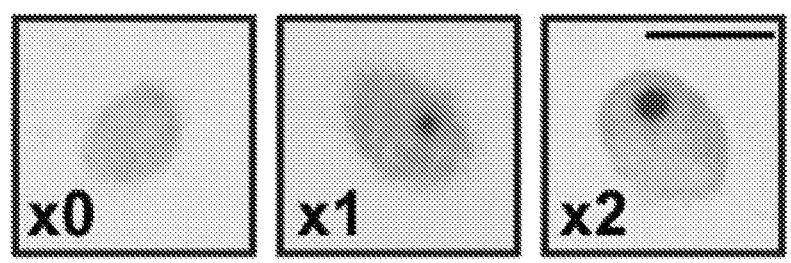
FIG. 23D illustrates synthetic DNA targets containing the Ex 16/17 junction sequence introduced by retroviral transduction in NIH-3T3 cells, and the target sequence (provirus) identified by Ex 16/17 jgISH.
Figure 23E:
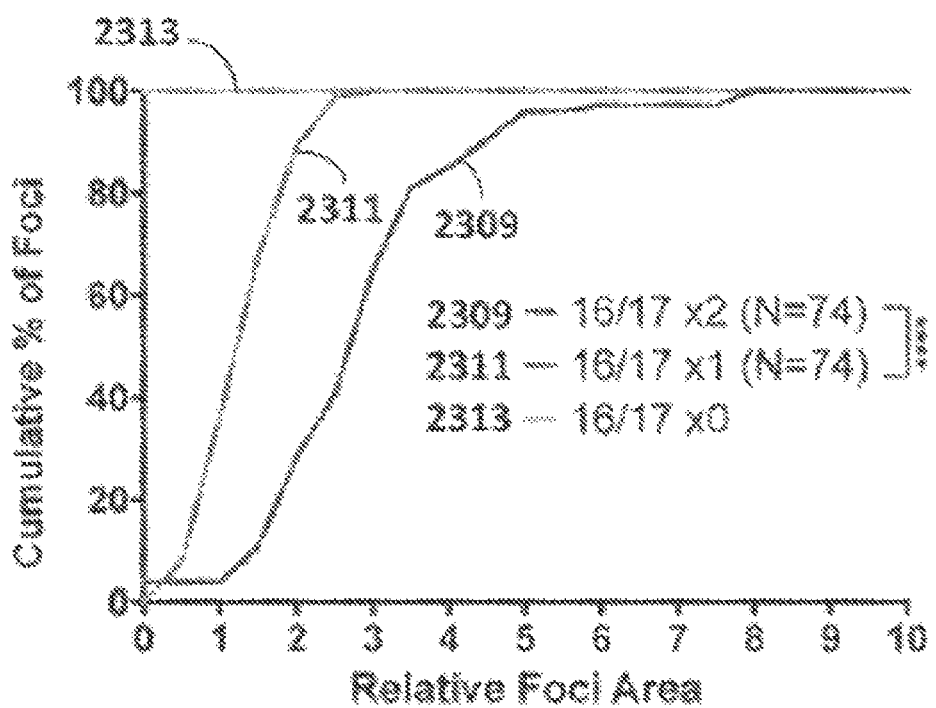
FIGS. 23E-23F illustrate graphs of foci size from concatamer (×2) from FIG. 23D.
Figure 23F:
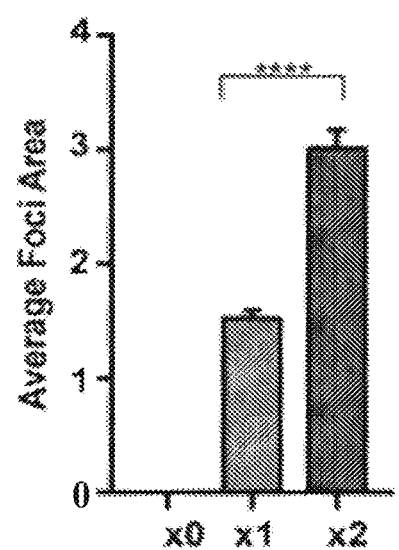

The human transgene and non-classical variants of APP were analyzed. Predominant signals within neuronal nuclei, contrasting with low levels in non-neuronal nuclei from the same animals as well as wild-type controls were observed. See FIGS. 22A-22G. jgISH analyses of J20 neurons aged 177 vs. 829 days identified age-related increases in Ex 16/17 foci sizes in neurons (FIGS. 23A-23C). The size of foci reflected increased DNA copy number, as demonstrated by control experiments in which retroviral-mediated insertion of DNA target sequences with increasing 16/17 copies allowed semi-quantitation of jgISH foci sizes relative to target copy number (FIGS. 23D-23F).

These results support neuronal gene transcription in generating gencDNAs.

Example 19. Co-Localization of APP and Aβ Plaques

Figure 24:
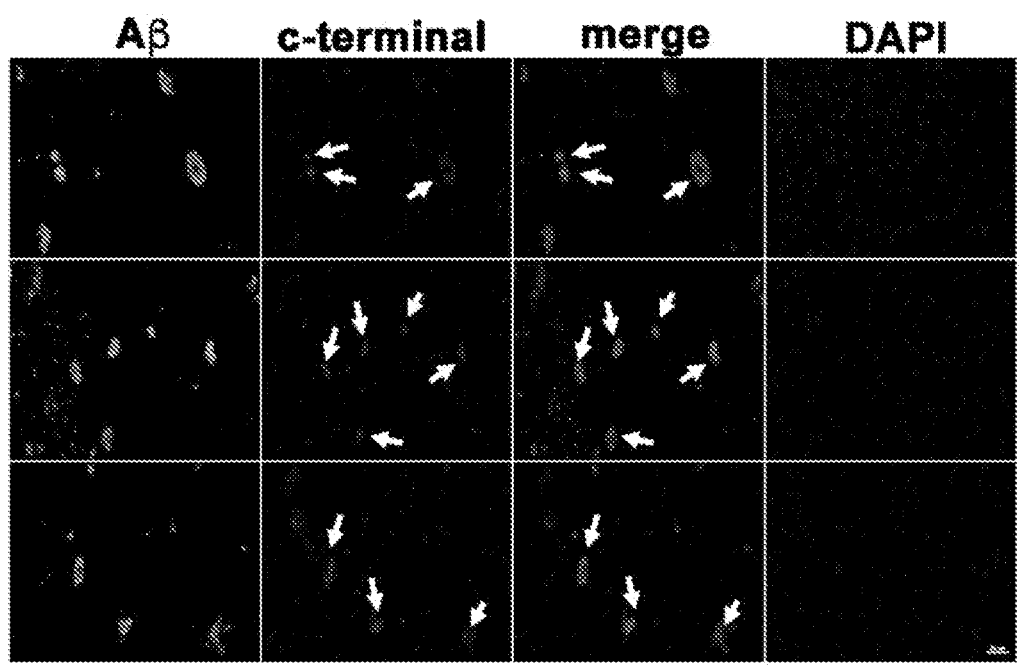
FIG. 24 illustrates cortical tissue sections from human Alzheimer's disease subjects stained with antibodies recognizing Aβ peptide ("Aβ") and APP c-terminal ("c-terminal"). "Merge" images illustrate co-localization of Aβ peptide with APP c-terminal. "DAPI" images illustrate nuclei staining.

Co-localization of APP c-terminal and Aβ plaques was determined in human tissue sections of subjects with Alzheimer's disease. Referring to FIG. 24, Aβ plaques ("Aβ") were stained using an antibody recognizing Aβ peptide as seen in green in the first panel from the left. APP c-terminal ("c-terminal") was stained using an antibody recognizing APP c-terminal as seen in red in arrows in the second panel from the left. DAPI ("DAPI") was used to stain the nuclei as seen in blue in the fourth panel from the left. When images of Aβ and APP c-terminal were merged ("merge") as seen in the arrows in the third panel from the left, Aβ and APP c-terminal were found to be co-localized.

The data shows that non-classical variants of APP identified are present in Aβ plaques and are involved in Aβ plaque formation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting one or more variants of an amyloid precursor protein (APP) gene in a human subject in need thereof, the method comprising:
   (a) detecting a presence of the one or more variants of the APP gene by binding of one or more probes to the one or more variants, wherein the one or more variants of the APP gene are from human neuronal cells of the human subject, wherein the one or more probes hybridize to an intraexonic junction between exon 1 and exon 11, exon 1 and exon 13, or exon 3 and exon 14;
   wherein the one or more variants comprise a single nucleotide variation (SNV) in the APP gene and wherein the one or more variants comprise a sequence as set forth in SEQ ID NO: 5, 7, 8, or 9, and
   wherein the SNV in the APP gene translates to amino acid positions in APP selected from the group consisting of: A673V, A713T, T714I, V715M, V715A, I716M, T719P, and L723P,
   wherein the detection indicates the human subject as being at risk of having or developing Alzheimer's disease; and
   (b) administering to the human subject a cholinesterase inhibitor, an NMDA receptor antagonist, or an anti-amyloid beta antibody.

* * * * *